United States Patent [19]
Dominguez et al.

[11] Patent Number: 5,668,735
[45] Date of Patent: Sep. 16, 1997

[54] METHOD AND APPARATUS FOR CONTINUOUS EMISSIONS MONITORING SYSTEM USING GAS CHROMATOGRAPHY

[75] Inventors: Luis Mayan Dominguez; Forrest Wendell Bowling; William Monroe Coleman, III; Bert Miller Gordon, all of Winston-Salem, N.C.

[73] Assignee: R. J. Reynolds Tobacco Company, Winston-Salem, N.C.

[21] Appl. No.: 657,922

[22] Filed: May 31, 1996

Related U.S. Application Data

[63] Continuation of Ser. No. 530,506, Sep. 19, 1995, Pat. No. 5,610,835, which is a continuation of Ser. No. 273,234, Jul. 15, 1994, abandoned, which is a continuation-in-part of Ser. No. 114,598, Aug. 31, 1993, abandoned.

[51] Int. Cl.$^6$ ........................................ G01N 30/02
[52] U.S. Cl. ............ 364/497; 73/19.02; 73/23.35; 73/23.42; 436/161
[58] Field of Search ............ 73/19.01, 19.02, 73/23.22, 23.35, 23.42; 364/497, 498, 571.01; 436/8, 161

[56] References Cited

U.S. PATENT DOCUMENTS

| | | | |
|---|---|---|---|
| 4,072,480 | 2/1978 | Wagner | 95/136 |
| 4,304,120 | 12/1981 | Myers et al. | 73/19.01 |
| 4,345,463 | 8/1982 | Wilson et al. | 73/23.35 X |
| 4,521,225 | 6/1985 | Jenkins et al. | 73/23.25 X |
| 4,556,547 | 12/1985 | Nishino et al. | 423/230 |
| 4,587,834 | 5/1986 | Fisher | 73/23.35 X |
| 4,731,732 | 3/1988 | Warchol et al. | 73/19.01 X |
| 4,758,408 | 7/1988 | Krawetz et al. | 73/19.01 X |
| 5,068,798 | 11/1991 | Heath et al. | 364/497 |
| 5,093,269 | 3/1992 | Leichnitz et al. | 73/23.42 X |
| 5,192,341 | 3/1993 | Eheler | 95/189 |
| 5,235,843 | 8/1993 | Langhorst | 73/19.02 |
| 5,387,564 | 2/1995 | Takeuchi et al. | 502/62 |

*Primary Examiner*—Edward R. Cosimano

[57] ABSTRACT

A method of and apparatus for automatically monitoring and reporting the exact concentrations of specific chemicals contained in one or more air streams is disclosed in which the system automatically calibrates one or a plurality of gas chromatographs using a plurality of calibration gases and then alternatingly samples and analyzes air streams containing volatile or semi-volatile organic or inorganic compounds. When a plurality of gas chromatographs are utilized, the system of the present invention is capable of simultaneously analyzing one or more air streams for a plurality of compounds. Apparatus for ensuring sample line and measurement system integrity is also disclosed. The results of the analysis are recorded and are stored in computer files which include the exact chemical concentrations of a sample taken from an air stream.

28 Claims, 36 Drawing Sheets

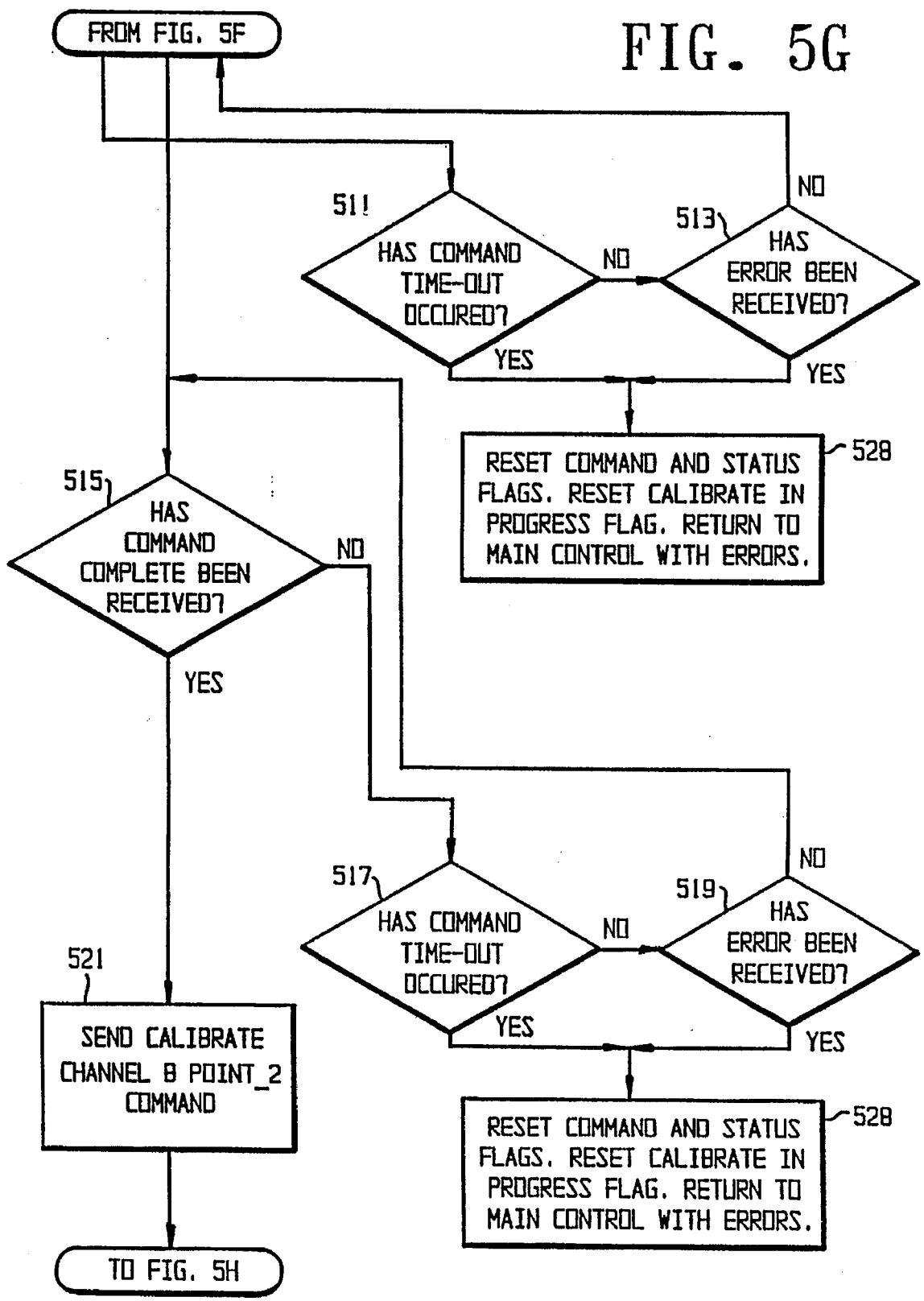

METHOD AND APPARATUS FOR CONTINUOUS EMISSIONS MONITORING SYSTEM USING GAS CHROMATOGRAPHY

CROSS-REFERENCE TO RELATED APPLICATION

This application is a continuation of U.S. patent application Ser. No. 08/530,506, filed Sep. 19, 1995, now U.S. Pat. No. 5,610,835 which is a continuation of U.S. patent application Ser. No. 08/273,234, filed Jul. 15, 1994, now abandoned, which is a continuation-in-part of U.S. patent application Ser. No. 08/114,598, filed Aug. 31, 1993 and entitled Method and Apparatus for Emissions Monitoring System Using Gas Chromatography, now abandoned.

FIELD OF THE INVENTION

The present invention relates to a method of and an apparatus for a continuous emissions monitoring system using a gas chromatograph and, more particularly, to a method of and apparatus for monitoring compounds emitted by certain industrial users.

BACKGROUND OF THE INVENTION

As the public and private sectors have become more aware of the potential damage caused by waste products produced by industry which are discharged into the atmosphere, there has been an increased recognition and demand for monitoring and minimizing, to the extent possible, the discharge of such materials into the atmosphere. In that regard, the United States government, through the Environmental Protection Agency, has established certain regulations for the level of different types of emissions which may be discharged into the atmosphere.

The EPA monitors compliance with its regulations essentially by requiring those individual companies whom it has licensed to discharge emissions at a certain rate to monitor such discharges and to maintain records of such discharges for reporting to and review by the EPA. Typically, the subject company monitors the output of the air stream being evacuated from equipment which uses substances monitored by the EPA. The company also is required to monitor the discharge stream from the device used to remove the licensed substances from the air stream before it is discharged into the atmosphere. Such a device can be a carbon bed. Monitoring of both the air stream input to and discharged from a carbon bed may be required to document both the level of monitored substance use as well as the level of discharge of that substance into the atmosphere. In that manner, the EPA ensures that companies stay within compliance of their license for that particular monitored substance.

At the present time, while there are instruments available for performing such monitoring functions, accurate instruments are very expensive. Although inexpensive instruments are available, they are very inaccurate. The limitations of those instruments have been recognized by the EPA in the appendices to the proposed enhanced monitoring regulations. Prior to the present invention disclosed herein, the EPA was limited to the standards as currently written because no instruments could provide the level of accuracy of the present invention at a cost which is economical such that the affected industries could afford the equipment. Applicants have invented a system which can perform the measuring, monitoring and reporting of exact concentrations of specific chemicals contained in one or more air streams in a manner which is more accurate than the expensive instruments, at a cost which is cost effective for the affected industries.

In light of the shortcomings of the presently available systems for monitoring and reporting emissions data as discussed above, it would be desirable to provide a reliable and cost-effective method and apparatus which could automatically monitor both the inlet and outlet air streams of, for example, a carbon bed with an accuracy superior to the accuracy obtainable at the present time by existing systems.

In addition, it would be desirable to provide a system for monitoring and reporting emissions data as discussed above which provides for the use of a plurality of parallel processing systems such that the air streams under test can be simultaneously analyzed for a number of different components contained in those air streams. It is also desirable that such a system ensure that the process stream sample or samples analyzed by the emissions monitoring system not be chemically or physically altered by the measurement hardware used by such a system. That is, the integrity of the measurement system and the sample lines should be maintained.

SUMMARY OF THE INVENTION

The present invention is directed to a method of and apparatus for automatically monitoring and reporting the exact concentrations of specific chemicals contained in one or more air streams, such as the inlet and outlet air streams, of a carbon bed. The method and apparatus of the present invention automatically select the individual air stream to be sampled using automatic valves. It automatically recalibrates the gas chromatograph which is the heart of the system by switching the sample line of the gas chromatograph to a reference gas mixture and then causing the gas chromatograph to sample and employ the data collected from this sampling run as a basis for subsequent analytical computations.

The present invention is also directed to a method of and apparatus for automatically simultaneously monitoring and reporting the exact concentrations of one or more specific organic and/or inorganic compounds contained in one or more air streams. The method and apparatus of the present invention provide for the parallel processing of one or more air streams using a number of gas chromatograph systems which process an air stream in parallel for different compounds. In that manner, up to 50 sample streams and 10 calibration streams can be analyzed and utilized by the present invention.

The present invention also provides a method of and apparatus for ensuring that the one or more process stream samples being analyzed by the gas chromatograph system are not chemically or physically altered from the time the samples leave the process streams until they reach the measurement system. In that manner, the integrity of both the measurement system and the sample line is maintained.

The present invention generates an historical record of all monitored measurements. The historical record is stored in computer files which may be made available to the Management Information Computer System (MICS) of the facility utilizing the present method and apparatus for emissions monitoring. The contents of the records or reports generated include for example, the exact chemical concentrations of a sample taken from an air stream, the mass airflow in the duct that the sample was taken from, the identity of the air stream from which the sample was taken and the time at which the measurement was taken and the weight, in pounds, of each compound before and after the carbon bed. In addition the method and apparatus of the present invention perform self-diagnostics and report any out-of-limit conditions to personnel and/or control systems such that the out-of-limit information can be utilized to effect corrective action as well as recording the out-of-limit information to a database.

With the foregoing and other objects, advantages and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

FIGS. 5A–5H are a flow chart illustrating the Gas Chromatograph Calibrate Routine software used with the system of the present invention;

DETAILED DESCRIPTION OF THE INVENTION

Figure 1:
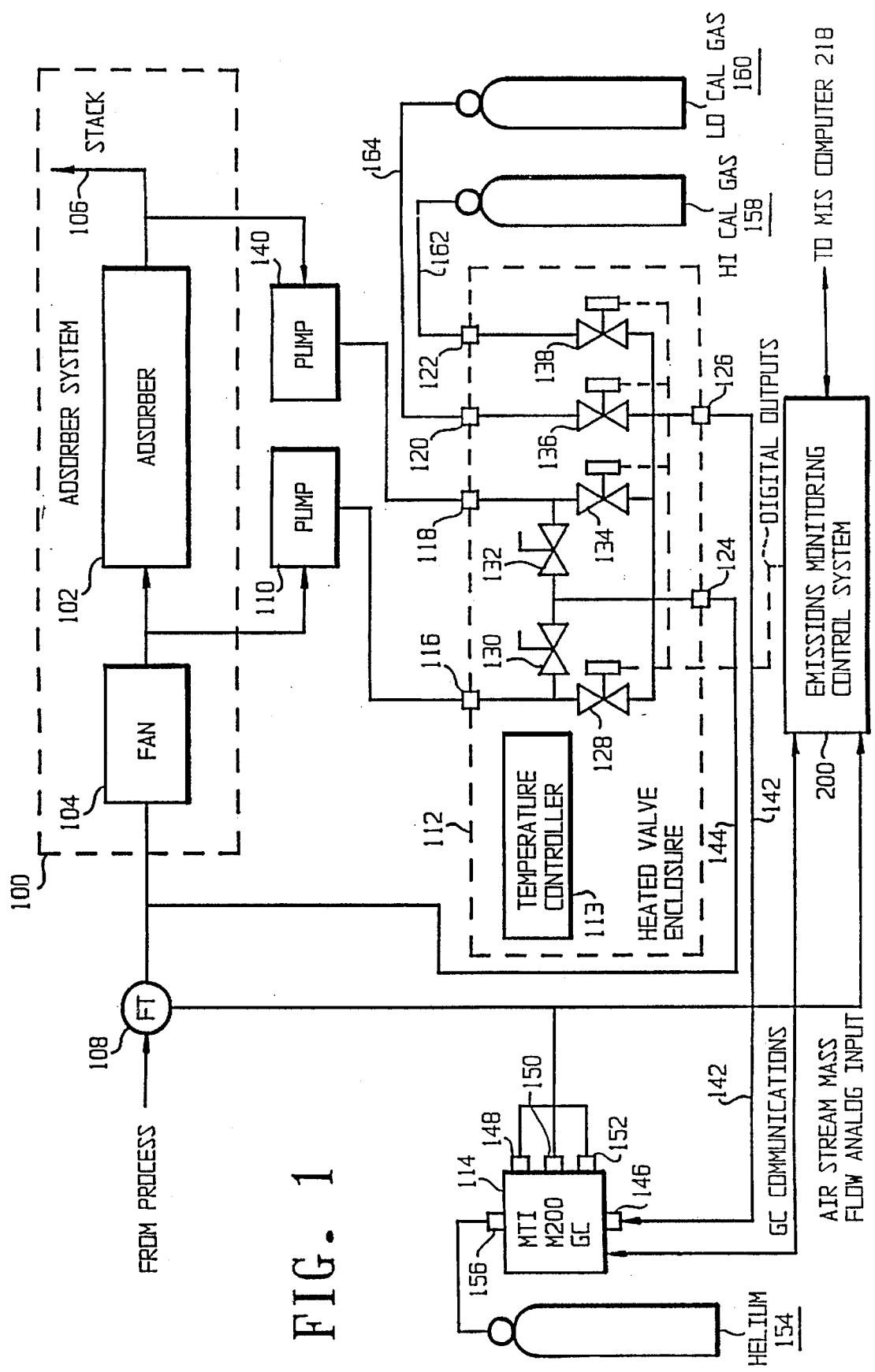
FIG. 1 is a schematic block diagram illustrating the emissions monitoring and reporting system showing the physical interconnections of tubing, pumps, valves and other devices utilized with the system of the present invention.

Referring now to the drawings wherein like parts are designated by like reference numerals throughout, there is illustrated in FIG. 1 a schematic block diagram of the emissions monitoring system utilized with the present invention, showing the physical connections between the various components. The system illustrated is designed to monitor the input and output air stream to and from an existing absorber system 100, such as a carbon bed. Such existing absorber system 100 includes the absorber or carbon bed itself 102, a fan 104 which is used to create an air stream through the absorber 102 and an exhaust stack 106 by which the output or discharge air stream from the absorber 102 is discharged into the atmosphere. The substance laden air stream is collected by means of a duct system (not shown) and the fan 104 from the area in which the monitored substance, such as a solvent, is utilized. The substance laden air stream passes through a mass air flow meter 108 prior to reaching the fan 104 which forms part of the existing absorber system 100 of a plant or manufacturing facility.

The emissions monitoring system of the present invention monitors both the inlet and the discharge air streams of the absorber 102 on an alternate basis. In addition to being input into the absorber 102, the substance laden air gathered from the plant area in which the regulated substance is used is fed to an inlet air pump 110 and from there into a heated valve enclosure 112 whose temperature is controlled by the temperature controller 113. The valve system, which will be described hereafter, is electrically controlled and enables the emissions monitoring system of the present invention to both monitor the inlet and discharge air streams of the absorber 102 as well as to automatically calibrate the gas chromatograph or GC 114. Under programmable control, the electrically controlled valve system enables selection of the proper inlet to the gas chromatograph 114 to accomplish the appropriate monitoring or calibration function.

Because the electrically controlled valves of the valve system all share a common manifold (not shown) and because the valves themselves may contain materials which adsorb some of the components of the sample air streams, the valves themselves are contained in an insulated enclosure 112 which is heated to a temperature in excess of 100 degrees Celsius, under control of the temperature controller 113, in order to minimize adsorption.

The output from the inlet sample air stream pump 110 is fed to the valve enclosure 112 through a sample inlet port 116. A valve 128 and a by-pass restrictor 130 are directly connected to the output of the sample inlet port 116. In a like manner, a second and identical pump 140 is connected to receive the discharge air stream output by the absorber 102 and is directly connected to a discharge inlet port 118 of the valve enclosure 112. The discharge inlet port 118 of the valve enclosure 112 is connected to a valve 134 and a by-pass restrictor 132. The output of the valves 128 and 134 is connected to the sample output port 126, which is connected by means of a sample line 142 to an inlet port 146 of the GC 114. The output sides of the by-pass restrictors 130 and 132 are connected by means of a discharge outlet port 124 and a discharge line 144 to the air stream input to the fan 104. A plurality of GC outlet ports 148, 150 and 152 connect the discharge outlet (not shown) of the GC 114 to the discharge line 144. A source of helium 154 is connected by means of an input port 156 to the GC 114.

The gases used to calibrate the GC 114 are contained in two gas cylinders, for example, elements 158 and 160, respectively. The gas used for the "hi" calibration of the GC 114 is connected from its container 158 by means a first gas line 162 through a high cal gas input port 122 and then to the inlet side of a valve 138. The gas used for the "lo" calibration of the GC 114 is connected from its container 160 to the low cal gas input port 120 by means of a pipe or second gas line 164. The inlet side of a valve 136 is connected to output of the low cal gas input port 120. The outlet of both of the valves 136 and 138 is connected to the sample outlet port 126, in the same manner as the outlet side of the first and second sample valves 128 and 134.

Figure 2A:
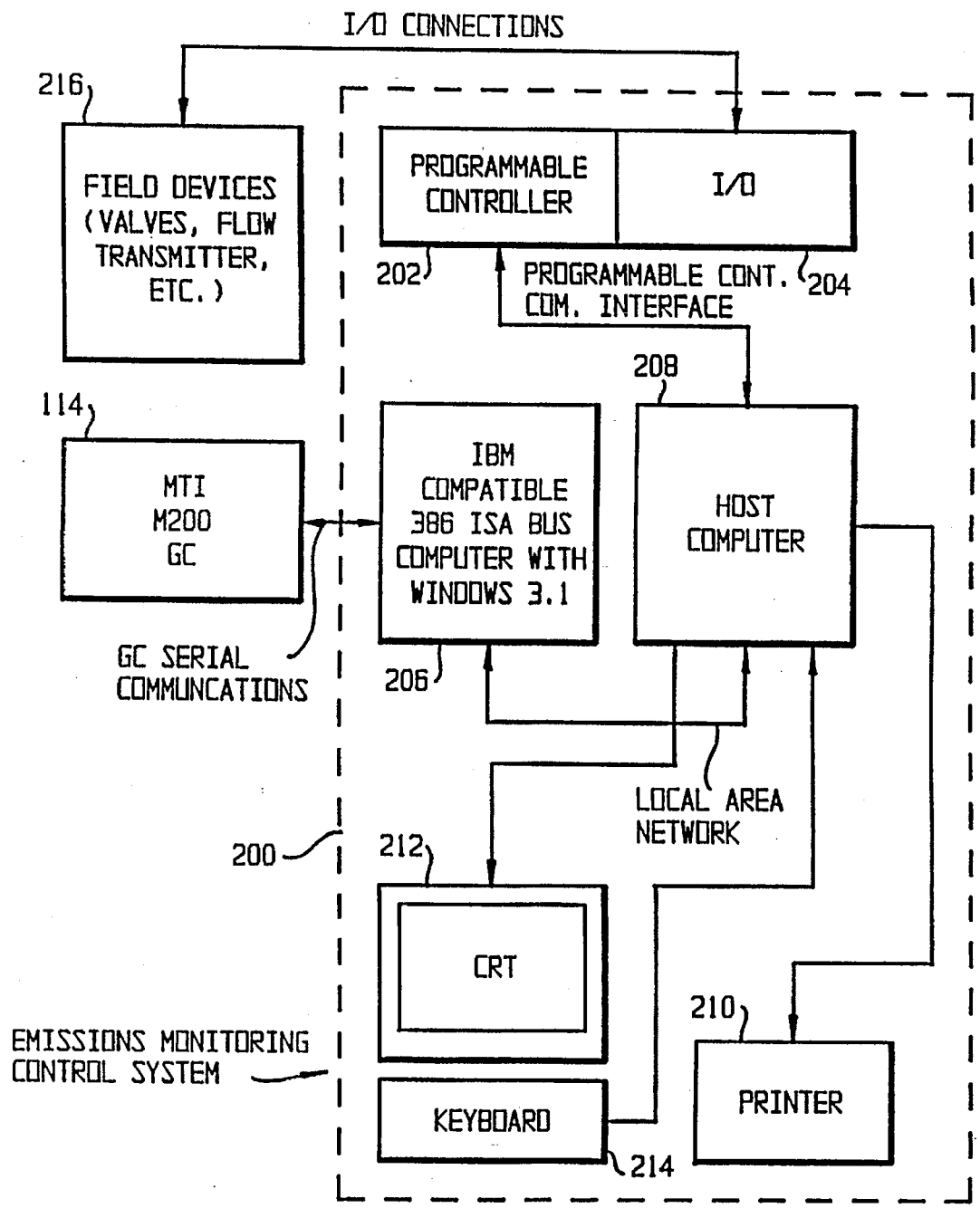
FIG. 2A is a schematic block diagram of the emissions monitoring control system of the present invention showing the components and interconnections of electrical and computer control systems.

The GC 114 may preferably be a model M200 gas chromatograph available from Microsensor Technology, Inc. (MTI) of Fremont, Calif. Also included with the GC 114 is EZChrom software, which is executed on the computer 206. The computer 206, together with the EZChrom software, functions to directly control the operation of the GC 114. The GC 114 is also controlled under command of the PLC 202, which additionally controls the valves 128, 134, 136 and 138, and by-pass restrictors 130 and 132, as appropriate. The emissions monitoring control system 200 is connected to the mass air flow transmitter 108 such that it receives an analog input from the flow transmitter 108 which corresponds to the air stream mass flow through the flow transmitter 108. The flow transmitter 108 may preferably be a Model EVA-4000 mass air flow meter available from Kurz Instruments, Inc. of Monterey, Calif. The emissions monitoring control system 200 also includes the host computer 208. As shown in FIG. 2A, the host computer 208 is connected to a printer 210, a CRT 212 and a keyboard 214 in a standard manner. The host computer functions to provide an interface between the PLC 202 and the computer 206 which operates the GC 114.

The calibration gases stored in the gas tanks 158 and 160 are preferably 400 ppm and 50 ppm, respectively and are available, for example, from Scott Specialty Gases, Inc., Durham, N.C. The composition of such gases can readily be determined by a skilled artisan, depending on the regulated emission being monitored. Solely as an example of the use of the system of the present invention, such invention can be used to monitor regulated VOCs present in connection with printing processes. Thus, for example, the present invention would be utilized to monitor for the following compounds: toluene, n-propyl acetate, isopropyl acetate, n-propyl alcohol, isopropyl alcohol, methyl ethyl ketone, ethanol, heptane, ethyl acetate and methane. The calibration gases would contain those same compounds. The heated valve enclosure 112 is an RJR stream selector. The sample air pumps 110 and 140 may be model no. M01310V available from Dimensions, Inc., of Deerfield Beach, Fla.

Referring now to FIG. 2A, the emissions monitoring control system 200 is shown in more detail and is formed by a programmable logic controller (PLC) 202 and its associated input/output controllers as well as a computer 206, which may be an IBM compatible 386 ISA bus computer operating with the Microsoft Windows 3.1 operating system. The PLC 202 may preferably be a Model No. PLC-5/20 or 984-685, available respectively from the Allen Bradley Company of Milwaukee, Wis. or AEG Modicon, of North Andover, Mass..

The input/output controller 204 is connected to the flow transmitter 108 and valves 128–138, (shown in FIG. 2A as element 216) as previously described, in order to receive electrical inputs or provide electrical inputs to those devices, as necessary. The programmable controller 202 is connected directly to the host computer 208 such that the operation of the programmable controller 202 may be controlled by use of the keyboard 214 and the CRT 212 of the host computer 208. The host computer 208 may be an IBM compatible 386 ISA bus computer operating with Microsoft Windows 3.1.

The computer 206, as previously described, is directly connected to the GC 114 such that it directly controls the operation of the GC 114. The computer 206 may also be connected by means of, for example, a local area network, to the host computer 208. In that manner, the host computer 208 can be utilized to extract the historical monitoring and operation data received by the computer 206 from the GC 114. The printer 210 can be used to print out such historical data, as well as to perform other obvious functions.

The programmable controller 202 includes a real time clock, which provides the basis for all scheduled events for the emissions monitoring system of the present invention. As will be described hereafter, the occurrence of any event is fully programmable through the programmable logic controller 202 code, or from the operator interface formed by the host computer 208 and the peripherals 212 and 214 connected thereto.

Figure 2B:
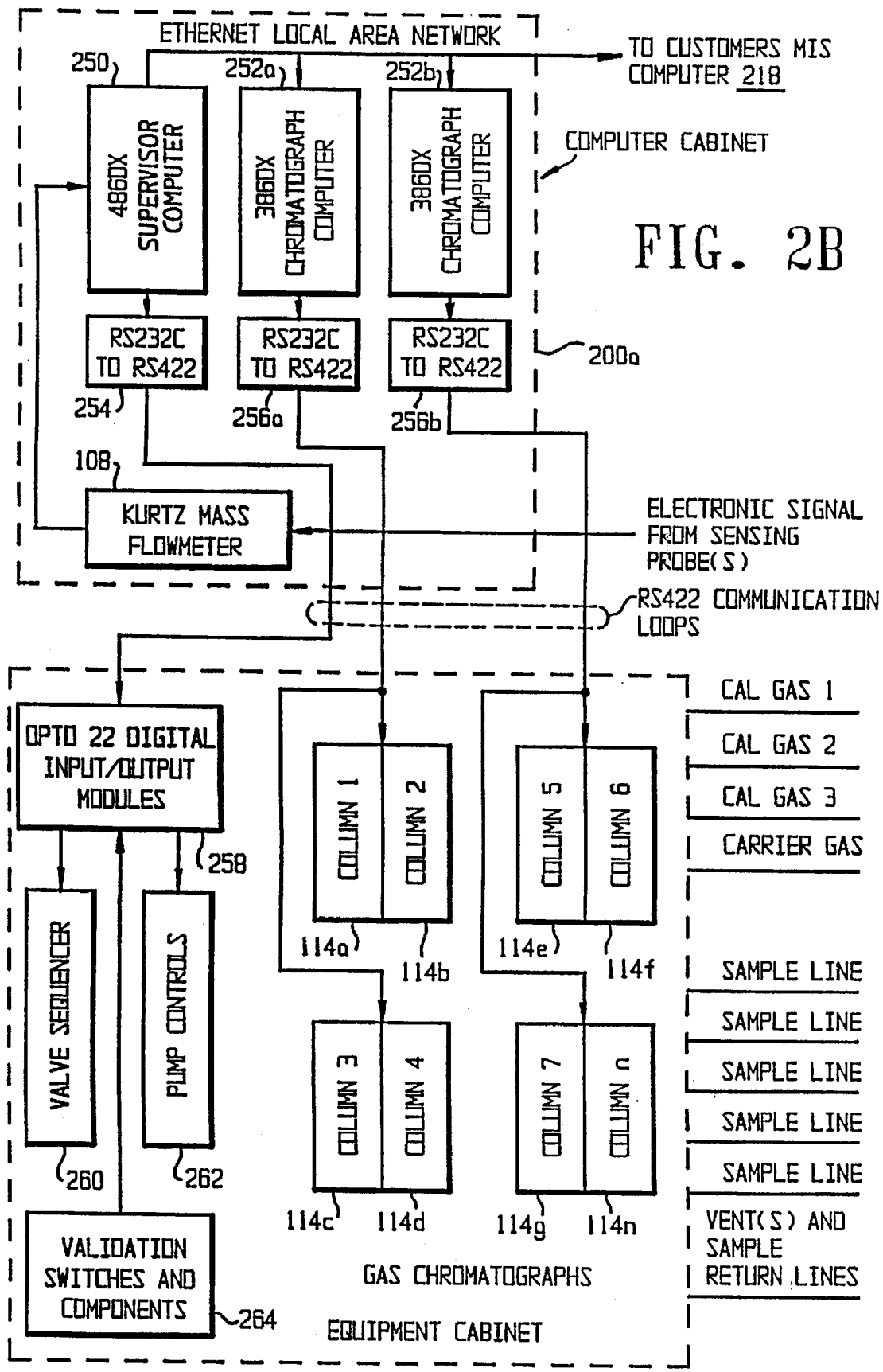
FIG. 2B is a schematic block diagram of a preferred embodiment of a continuous emissions monitoring control system of the present invention for use with the embodiment of the emissions monitoring and reporting system shown in FIG. 9.
Figure 9A:
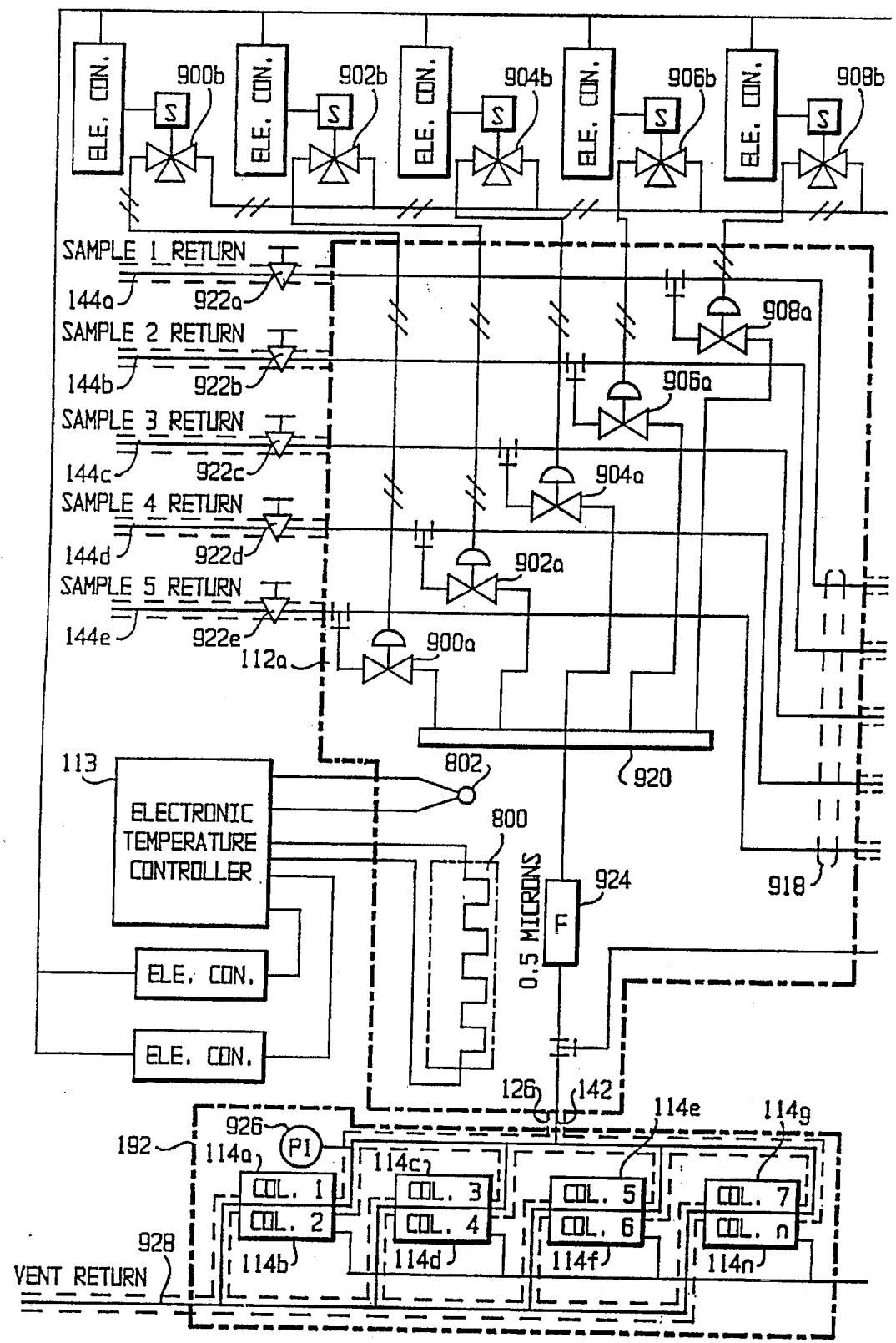
FIGS. 9A–9B is schematic block diagram illustrating an alternate embodiment of the emissions monitoring and reporting system shown in FIG. 1 which uses a plurality of gas chromatograph systems.
Figure 9B:
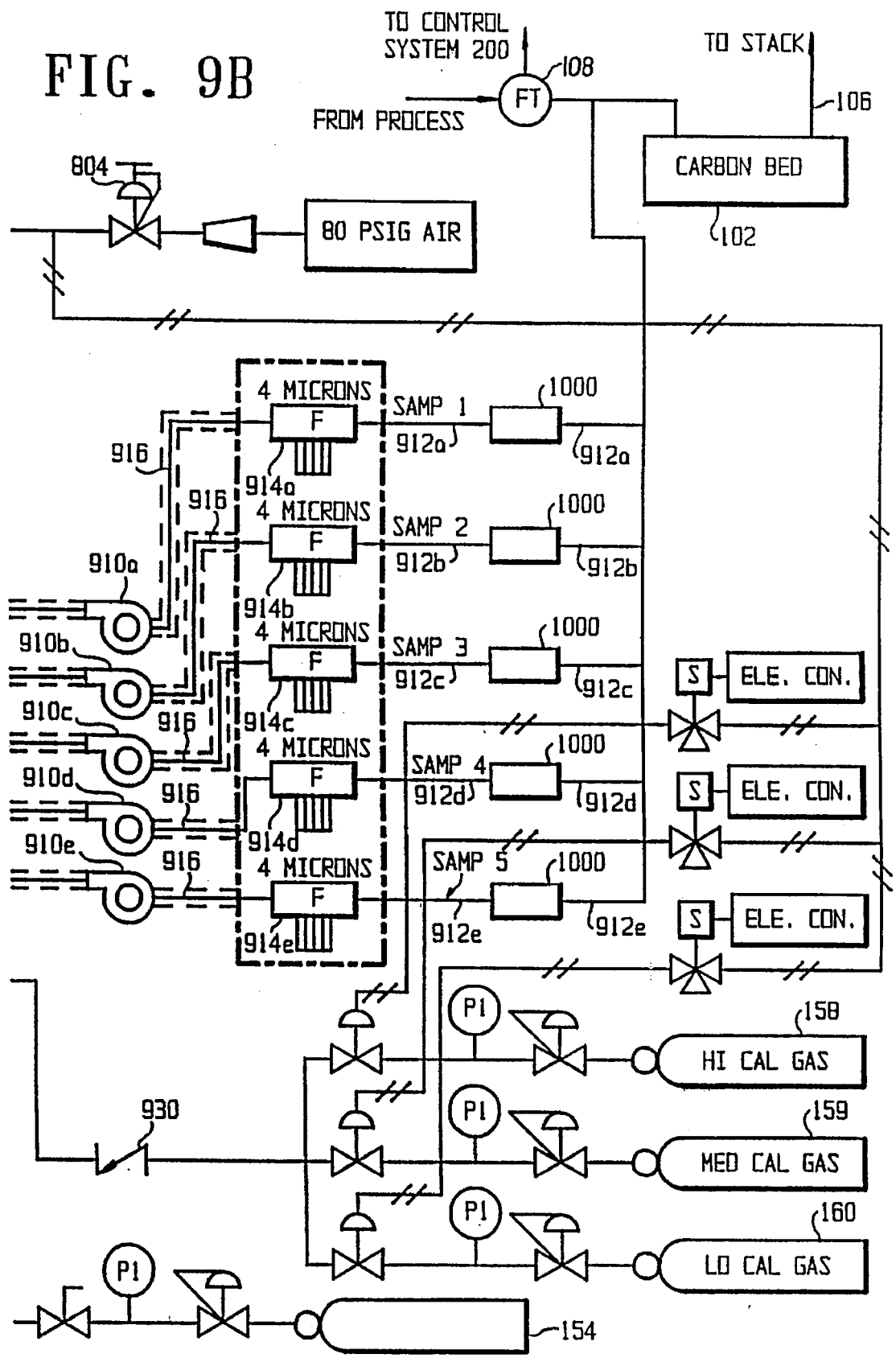
Figure 10:
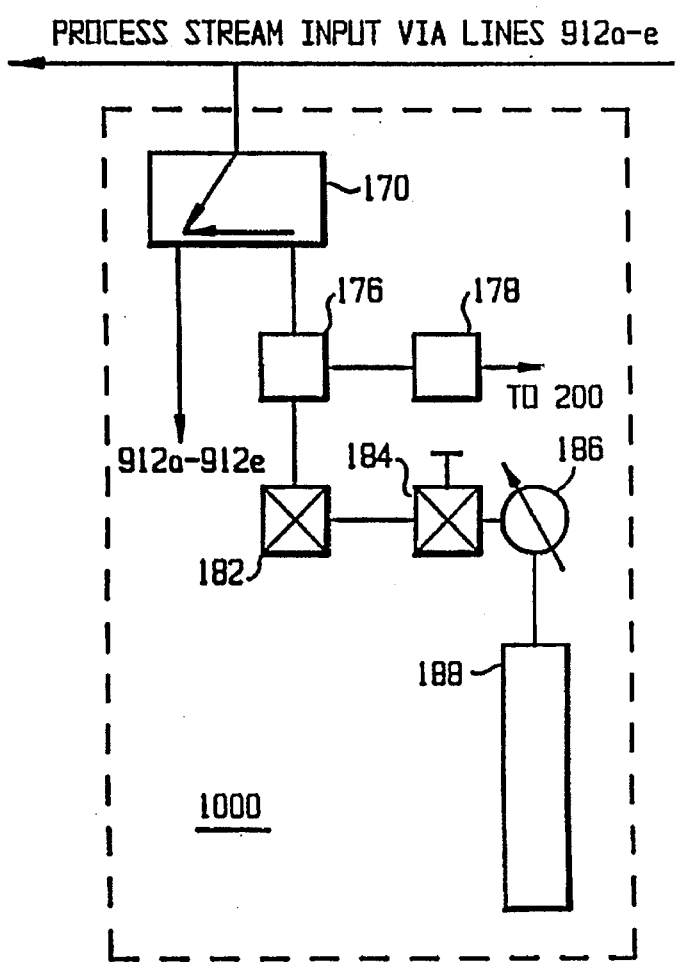
FIG. 10 is a schematic block diagram illustrating the physical interconnections of tubing, pumps, valves and other devices utilized to ensure the measurement system and sample line integrity of the emissions monitoring and reporting system of the present invention.
Figure 14:
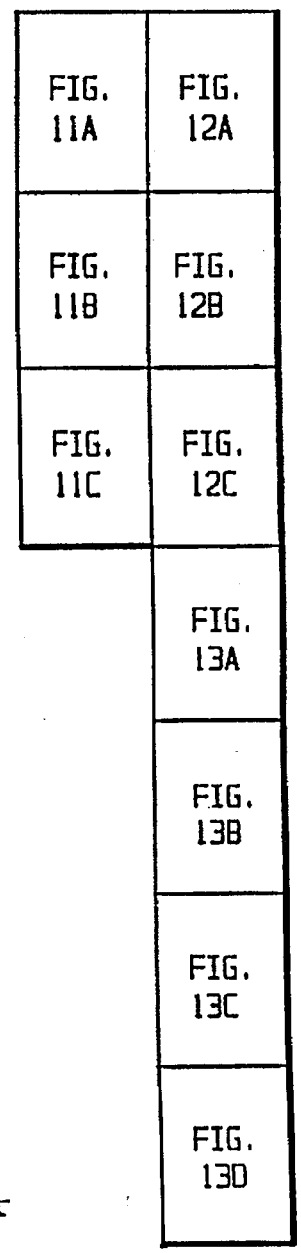
FIG. 14 is a diagram illustrating the relationship of the flow charts shown in FIGS. 11A–11C, 12A–12C and 13A–13D.

FIG. 2B shows, in diagrammatic form, the Continuous Emissions Monitoring Control System 200a which is utilized with the preferred embodiment of the invention, the hardware diagram of which is shown in schematic form in FIGS. 9A–9B and 10 and the software routines of which are shown in flow chart form in FIGS. 11A–11C, 12A–12C and 13A–13D.

The control system utilizes a supervisor computer 250 which is connected by means of an EISA bus to each of the EZChrom or GC chromatograph computers 252a–252b. Preferably, the supervisor computer 250 is configured as an 80486 DX, 50 megahertz IBM compatible computer while each of the chromatograph computers 252a–252b is configured as an 80386 DX, 33 megahertz IBM compatible computer. The supervisor computer 250 is connected by means of an RS232C loop to receive the output from the mass flow meter 108.

In addition to being connected to each of the chromatograph computers 252a–252b and to the customer's MIS computer 218 by means of, for example, an Ethernet local area network, the supervisor computer 250 is also connected, by means of a signal converter 254 (RS232C to RS422) to one or more digital input/output modules 258, through which the supervisor computer 250 controls the valve sequencer 260, the pump controls 262 and the validation switches and other components 264.

Each of the chromatograph computers 252a–252b is connected, by means of a respective signal converter 256a–256n similar to the signal converter 254 used with the supervisor computer 250, to one or more of the gas chromatograph columns 114a–114n. Preferably, a single chromatograph computer 252a running the EZChrom software, is capable of operating up to four gas chromatograph columns 114a–114d. Each of the signal converters 254 and 256a–256n are connected by means of RS422 communication loops to the digital input/output modules 258 and gas chromatograph columns 114a–114n, respectively.

Figure 8:
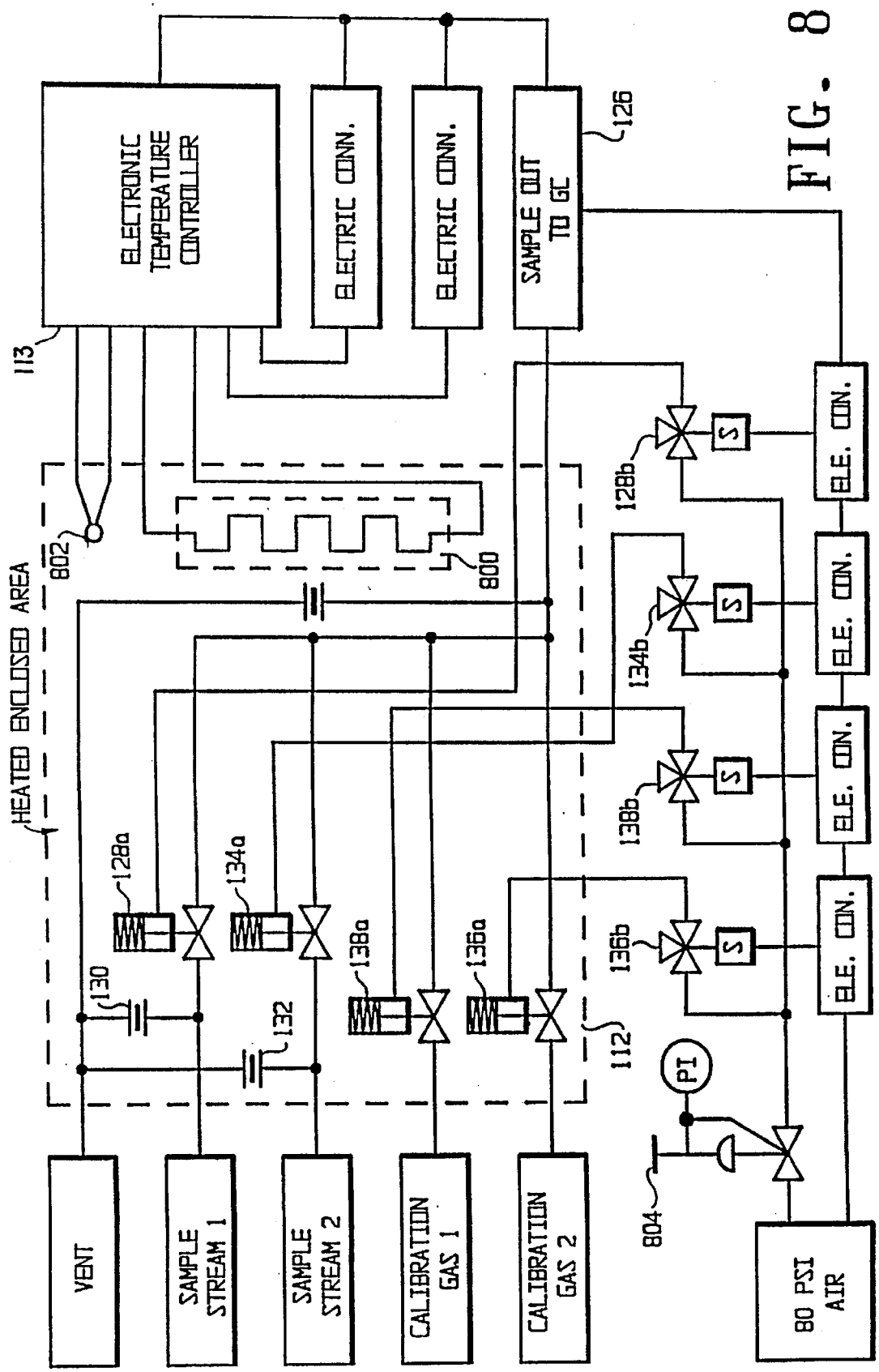
FIG. 8 is a schematic diagram of the RJR stream selector used with the system of the present invention.

FIG. 8 shows a schematic drawing of a stream selector which includes the heated valve enclosure 112 and electronic temperature controller 113. The heated valve enclosure 112 includes an electrical heating element 800, available from Chromalox Industrial Heating Products of Pittsburgh, Pa., part no. CIR-1020, which is connected to the electronic temperature controller 113. The temperature controller 113 may preferably be a model no. E5CS-R1KJX-F, available from Omron Electronics, of Schaumburg, Ill. The electronic temperature controller 113 is also connected to a thermocouple 802 which is located within the heated enclosed area of the heated valve enclosure 112 in order to provide feedback to the temperature controller 113. The thermocouple 802 may preferably be a standard Type J thermocouple, also available from Chromalox.

The heated valve enclosure includes a plurality of valves 128, 134, 136 and 138, as well as a plurality of by-pass restrictors 130 and 132. Such valves and by-pass restrictors are connected as previously described.

The valves 128, 134, 136 and 138 are formed from two components. The first component is a micro valve assembly, indicated as elements 128a, 134a, 136a and 138a, in FIG. 8. Those micro valve assemblies may preferably be part no. 1236091 or 1236103, available from SGE Incorporated, of Austin, Tex. Each of those micro valve assemblies is operated by a respective pneumatic solenoid valve 128b, 134b, 136b and 138b, each of which is connected to a pneumatic pressure regulator 804 which in turn is connected to a source of compressed air at, for example, 80 PSI. Each of the pneumatic solenoid valves 128b, 134b, 136b and 138b is connected to be controlled by the emissions monitoring control system 200 as previously described. The pneumatic solenoid valves may be part no. ETO-3-12 VDC, available from Clippard Instrument Laboratory of Cincinnati, Ohio. The pneumatic pressure regulator 608 may preferably be part no. 8386 available from Porter Instrument Company of Hatfield, Pa.

Figure 3A:
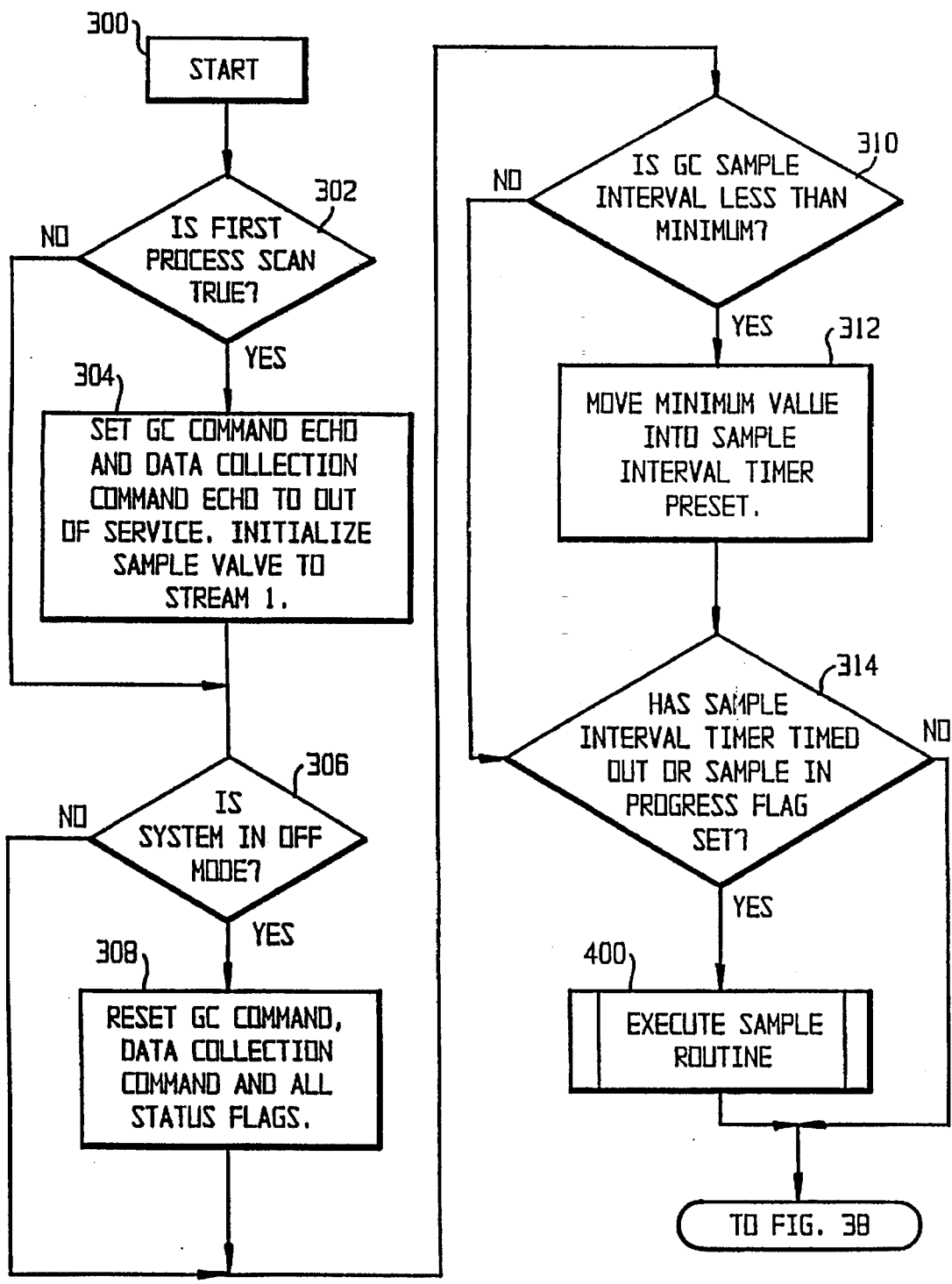
FIGS. 3A and 3B are a flow chart illustrating the Main Gas Chromatograph Control program used with the system of the present invention.
Figure 3B:
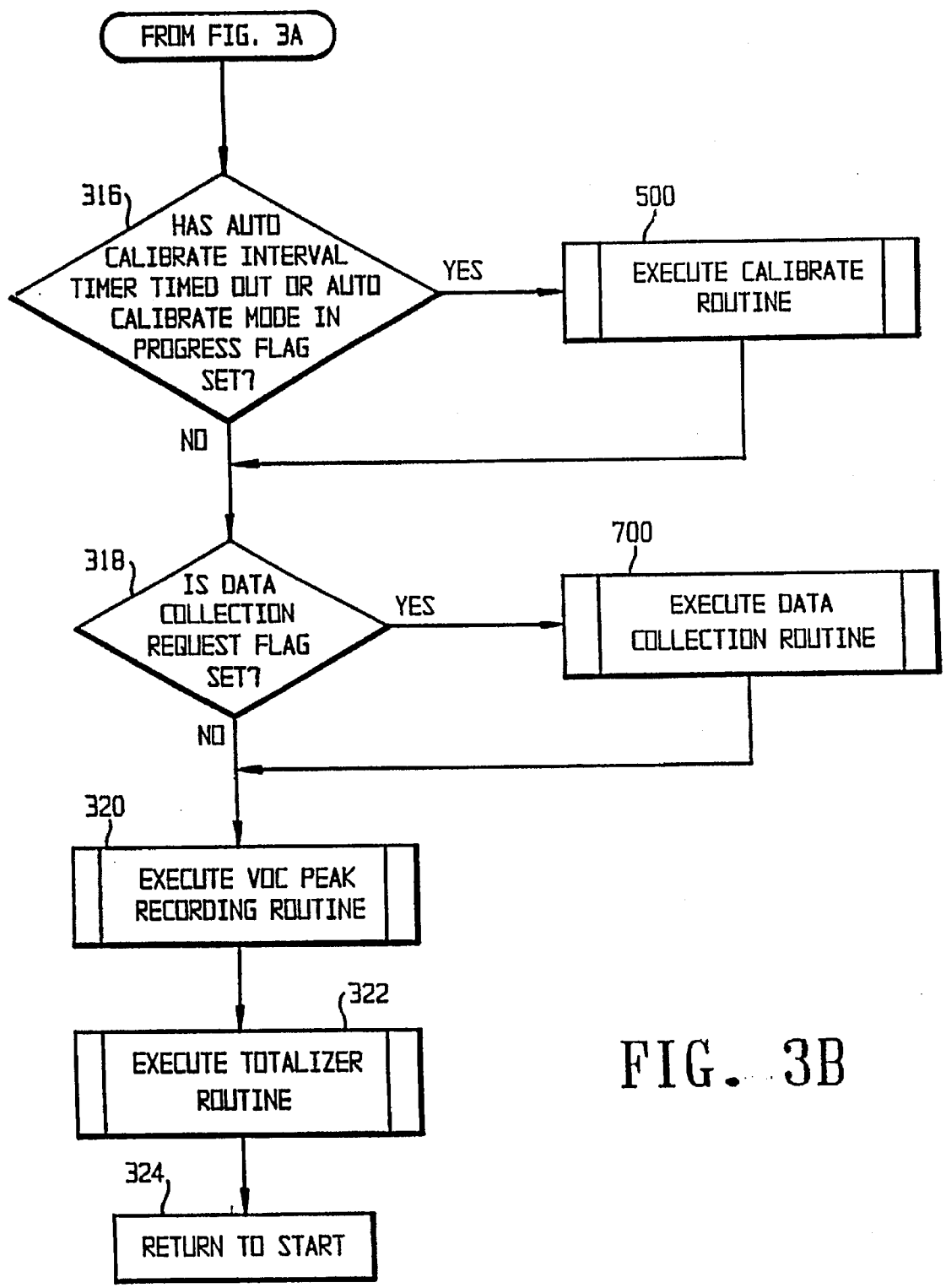

When the emissions monitoring system of the present invention is started-up, PC computer interface software contained in the host computer 208 interrogates the control software module (The EZChrom software) resident in the computer 206 to determine the status of the GC 114. The function of the PC computer interface software will be apparent to those of ordinary skill in the art and is also described herein. If the computer 206 determines that the GC 114 is functional, the host computer 208 interface software module writes a command to the response buffer of the PLC 202, informing it that the GC 114 is functional. The PLC 202 then prepares a calibration run, a flow chart of the software for which is set forth and described in connection with FIGS. 5A–5H. Once the GC Calibrate Routine is called, a first determination is made of whether a sample in progress flag has been set at step 502. If a positive determination is made at step 502, then control of the GC 114 is returned to the main control program at step 504. The main GC control program is resident in the PLC 202. A flow chart of the main GC control program is shown in FIGS. 3A–3B. All of the software represented by the flow charts shown in FIGS. 3A–3B, 4A–4C, 5A–5H, 6A–6C and 7A–7D is preferably resident in and executed by the PLC 202.

If it is determined at step 502 that a sample in progress flag has not been set, then a determination is made at step 506 of whether a calibrate in progress flag has been set. If no calibrate in progress flag has been set, then a determination is made of whether the calibrate interval timer has timed-out at step 508. If it is determined that the calibrate interval timer has not timed-out at step 508, then an error message is generated at step 510 and control is returned to the main GC control program. If an affirmative determination is made at step 508, then the calibrate in progress flag is set and the calibrate interval timer is reset at step 512.

If an affirmative determination is made at step 506 or after step 512, then the low calibration gas valve is selected and opened at step 514. Then at step 516, a determination is made of whether the low calibration gas valve has been open for a predetermined minimum period of time. If a negative determination is made at Step 516, then a determination is again made at Step 516 of whether the low calibration gas valve has been opened for a predetermined minimum period of time. Once a positive determination has been made at step 516, then a determination is made at step 518 of whether a Sample command has been sent. If a negative determination is made at step 518, then a command is sent to the GC 114 to sample the low calibration gas at step 520. After step 520, or if an affirmative determination is made at step 518, a determination is then made of whether the Sample command echo has been received at step 522. If a negative determination is made at step 522, then a determination is made at step 524 whether the time within which the command could have been sent has expired. If a negative determination is made at step 524, then a determination is made at step 526 of whether an error has been received. If a negative determination is made at step 526, then the GC Calibrate Routine returns and repeats step 522.

In the event of an affirmative determination at steps 524 or 526, then the command, status and calibrate in progress flags are reset and the GC Calibrate Routine returns to the main control program with errors at step 528.

If it is determined at step 522 that a Sample command echo has been received, then a determination is made at step 530 of whether a Sample Complete signal has been received in the command echo. If such a signal is determined to have been received at step 530, then the Sample Data Computations Routine is executed at step 601 and a determination is then made at step 540 of whether the low calibrate gas measurements are within expected limits. The flow chart of the Sample Data Computations Routine is shown and described in connection with FIGS. 6A–6C. If the low calibrate gas measurements are determined at step 540 to be within their expected limits, then a Calibrate Channel A command is generated and sent at step 544, indicating that the first monitoring channel for the GC 114 is to be calibrated.

If a negative determination is made at step 530, then a determination is made at step 532 of whether the sample timeout has occurred. If a negative determination is made at step 532, then a determination of whether an error has been received is made at step 534. If it is determined that an error has not been received at 534 then step 530 is repeated again. If an affirmative determination is made at steps 532 or 534, then the command, status and calibrate in progress flags are reset and the GC Calibrate Routine returns with errors to the main control program at step 528. Similarly, if it is determined at step 540 that the low calibration gas measurements are not within their expected limits, step 528 is also executed.

After step 544, a determination is then made of whether a command echo has been received at step 546. If a negative determination is made at step 546, then a determination is made at step 548 of whether a command timeout has occurred. If the command timeout has not occurred at step 548, then a determination is made at step 550 of whether an error has been received. If no error has been received, then step 546 is repeated. In the event that an affirmative determination is made at steps 548 or 550, then the command, status and calibrate in progress flags are reset and the GC Calibrate Routine returns to the main control program with errors at step 528.

If it is determined at step 546 that a command echo has been received, then a determination is made at step 554 whether the Complete command has been received. If the Complete command has not been received at step 554, then a determination is made at step 556 of whether the command timeout has occurred. If a negative determination is made at step 556, then a determination is made at step 558 of whether an error has been received. If no error has been received at step 558, then step 554 is repeated. If an affirmative determination is made at steps 556 or 558 then the command, status and calibrate in progress flags are reset and the GC Calibrate Routine returns to the main control program with errors at step 528.

If an affirmative determination is made at step 554, meaning that a Command Complete signal has been received, then the Calibrate Channel B Point 1 command is sent to the computer 206 at step 562 and then steps 564–568 and 572–576 are executed, in the same manner as steps 546–550 and 554–558, as have been previously described.

Next, the high calibration gas valve 138 is selected at step 580 and then steps 582–599 and 505–533 are executed, in the same manner as steps 516–576 and 601, discussed above in connection with calibrating the first point for channels A and B with the low calibration gas. After step 580, at step 582, a determination is made of whether the high calibration gas valve has been open for a predetermined minimum period of time. Once a positive determination has been made at step 582, then a determination is made at step 584 of whether a Sample command has been sent. If a negative determination is made at step 584, then a command is sent to the GC 114 to sample the low calibration gas at step 586. After step 586, or if an affirmative determination is made at step 584, a determination is then made of whether the Sample command echo has been received at step 588. If a negative determination is made at step 588, then a determination is made at step 590 of whether the time within which the command could have been sent has expired. If a negative determination is made at step 590, then a determination is made at step 592 of whether an error has been received. If a negative determination is made at step 592, then the GC calibrate routine returns and repeats step 588.

In the event of an affirmative determination at steps 590 or 592, then the command, status and calibrate in progress flags are reset and the GC calibrate routine returns to the main control program with errors at step 528.

If it is determined at step 588 that a Sample command echo has been received, then a determination is made at step 594 of whether a Sample Complete signal has been received in the command echo. If such a signal is determined to have been received at step 594, then the sample data computations routine is executed at step 599 and a determination is then made at step 505 of whether the high calibrate gas measurements are within expected limits. The flow chart of the sample data computations routine is shown and described in connection with FIGS. 6A–6C.

If the high calibrate gas measurements are determined at step 505 to be within their expected limits, then a Calibrate Channel A Point 2 command is generated and sent at step 507, indicating that the first monitoring channel for the GC 114 is to be calibrated.

If a negative determination is made at step 594, then a determination is made at step 596 of whether the sample timeout has occurred. If a negative determination is made at step 596, then a determination of whether an error has been received is made at step 598. If it is determined that an error has not been received at step 598, then step 594 is repeated again. If an affirmative determination is made at steps 596 or 598, then the command, status and calibrate in progress flags are reset and the GC calibrate routine return with errors to the main control program at step 528. Similarly, if it is determined at step 505 that the high calibration gas measurements are not within their expected limits, step 528 is also executed.

After step 507, a determination is then made of whether a command echo has been received at step 509. If a negative determination is made at step 509, then a determination is made at step 511 of whether a command timeout has occurred. If the command timeout has not occurred at step 511, then a determination is made at step 513 of whether an error has been received. If no error has been received, then step 509 is repeated. In the event that an affirmative determination is made at steps 511 or 513, then the command, status and calibrate in progress flags are reset and the GC calibrate routine returns to the main control program with errors at step 528.

If it is determined at step 509 that a command echo has been received, then a determination is made at step 515 of whether the Complete command has been received. If the Complete command has not been received at step 515, then a determination is made at step 517 of whether the command timeout has occurred. If a negative determination is made at step 517, then a determination is made at step 519 of whether an error has been received. If no error has been received at step 519, then step 515 is repeated. If an affirmative determination is made at steps 517 or 519 then the command, status and calibrate in progress flags are reset and the GC calibrate routine returns to the main control program with errors at step 528.

If an affirmative determination is made at step 515, meaning that a Command Complete signal has been received, then the Calibrate Channel B Point 2 command is sent to the computer 206 at step 521 and then steps 523–527 and 529–533 are executed, in the same manner as steps 509–513 and 515–519, as have been previously described. After the Command Complete signal has been received at step 529, the GC Calibrate Routine resets the command, status and calibrate in progress flags and returns to the main control program at step 535. The GC 114 has thus been calibrated.

The calibration run is started by the PLC 202, which writes a command into its command buffer telling the PC interface software module, which resides in the host computer 208, to execute a calibration run. Since the PC interface software module is constantly reading the command buffer of the PLC 202, it sees the Calibrate command and sends its own Calibrate command to the GC control software module (EZChrom software) resident in the computer 206 and then waits for an Acknowledgement signal. Upon receiving the Acknowledgement signal, the PC interface software module writes the Acknowledgement status to the PLC's response buffer. The Acknowledgement signal indicates that the calibration routine, as described above, has been completed.

Upon receiving the Acknowledgement status, the PLC768 closes the high calibration gas valve 138 (it previously closed the low calibration gas valve 136, at the end of the low calibration subroutine portion of the GC Calibrate Routine) and then opens the inlet air stream sample valve 130 to prepare for the beginning of a normal sample sequencing. Opening the inlet air stream sample valve 130 at this time tends to purge the inlet air stream line to the vent while the previous GC command is being processed. When the GC 114 finishes its calibration run, the main GC control program sends the results of the calibration to the PC interface software module running on the host computer 208. The PC software interface module then logs the time and results of the calibration runs to its historical database files and writes the status to the PLC 202 response buffer. If the results of the calibration run were outside of the predetermined limits, then the PLC 202 will turn on an alarm enunciator in order to notify maintenance personnel of the problem. If the results of the calibration run were within normal predetermined limits, then the normal measuring sequencing begins. Prior to discussing the normal measuring sequence, the main GC control program, the flow chart of which is shown in FIGS. 3A–3B, will be described.

Referring now to FIG. 3A, once the main GC control program is started at step 300, a determination is made at step 302 of whether the first process scan is true, meaning that the PLC 202 program has begun to run. If an affirmative determination is made at step 302, meaning that some variable may need to be initiated, then the GC command and Data Collection command echoes are set to out of service and the inlet air stream sample valve 130 is initialized at step 304. After step 304 or after a negative determination at step 302, a determination is then made of whether the main GC control program is in the off mode at step 306. If an affirmative determination is made at step 306, then the GC command, Data Collection command and all status flags are reset at step 308. After step 308 and after a negative determination at step 306, a determination is made at step 310 of whether the GC sample interval is less than the minimum interval at step 310. If an affirmative determination is made at step 310, then the minimum value is moved into the sample interval timer preset at step 312. After step 312 and if a negative determination is made at step 310, then a determination is made at step 314 of whether the sample interval timer has timed-out or whether the sample in progress flag has been set. If an affirmative determination is made at step 314, then the sample routine 400 is executed. A flow chart of the GC Sample Routine is shown and described in connection with FIGS. 4A–4C.

After the execution of the sample routine at step 400 and in the event of a negative determination at step 314, a determination is then made at step 316 of whether the automatic calibration interval timer has timed-out or whether the auto calibration mode in progress flag has been set. If an affirmative determination is made at step 316, then the calibration routine 500 is executed. A flow chart of the GC Calibration Routine is shown and described in connection with FIGS. 5A–5H, as has already been discussed.

After the execution of the calibration routine at step 500 or in the event of a negative determination at step 316, then a determination is made at step 318 of whether the data collection request flag has been set. If the data collection request flag is determined to have been set at step 318, then the Data Collection Routine 700 is executed. A flow chart of the Data Collection Routine is shown and described in connection with FIGS. 7A–7D.

After the execution of the Data Collection Routine 700 and in the event of a negative determination at step 318, then the VOC Peak Recording Routine is executed at step 320, the totalizer routine is executed at step 322 and then the main GC control program returns to start again at step 324. The VOC peak recording and totalizer routines are described hereinafter.

As discussed above, if the results of the calibration run, the flow chart of which is shown and described in connection with FIGS. 5A–5H, are within the expected limits, the normal measuring sequence begins. The normal measuring sequence alternately samples and measures from the two sample lines, the inlet air stream line to the absorber 102 and the discharge line from the adsorber 102. When the normal sequencing begins, the PLC 202 ensures that the inlet air stream sample valve 130 has been open long enough to purge the sample lines. The PLC 202 then writes a Measure Sample 1 command into its command buffer. The PC interface software module reads that command as well as the real time and mass air flow data from the PLC and sends a Measure command to the GC control software module running on the computer 206. The GC GC control software module then commands the GC 114 to execute a sample run. In that event, the valve 128 is opened such that the inlet air stream to the scrubber system 102 is sampled and passes through the outlet port 124 and into the inlet port 146 of the GC 114.

When the GC 114 acknowledges the command to execute a sample run, the GC control software module sends the Acknowledgement status to the PC interface software module which writes the Acknowledgement status to the PLC 202 response buffer. The PLC 202 then causes the inlet air stream sample valve 130 to close and opens the discharge air stream sample valve 132 in preparation for collecting the next sample.

Figure 4A:
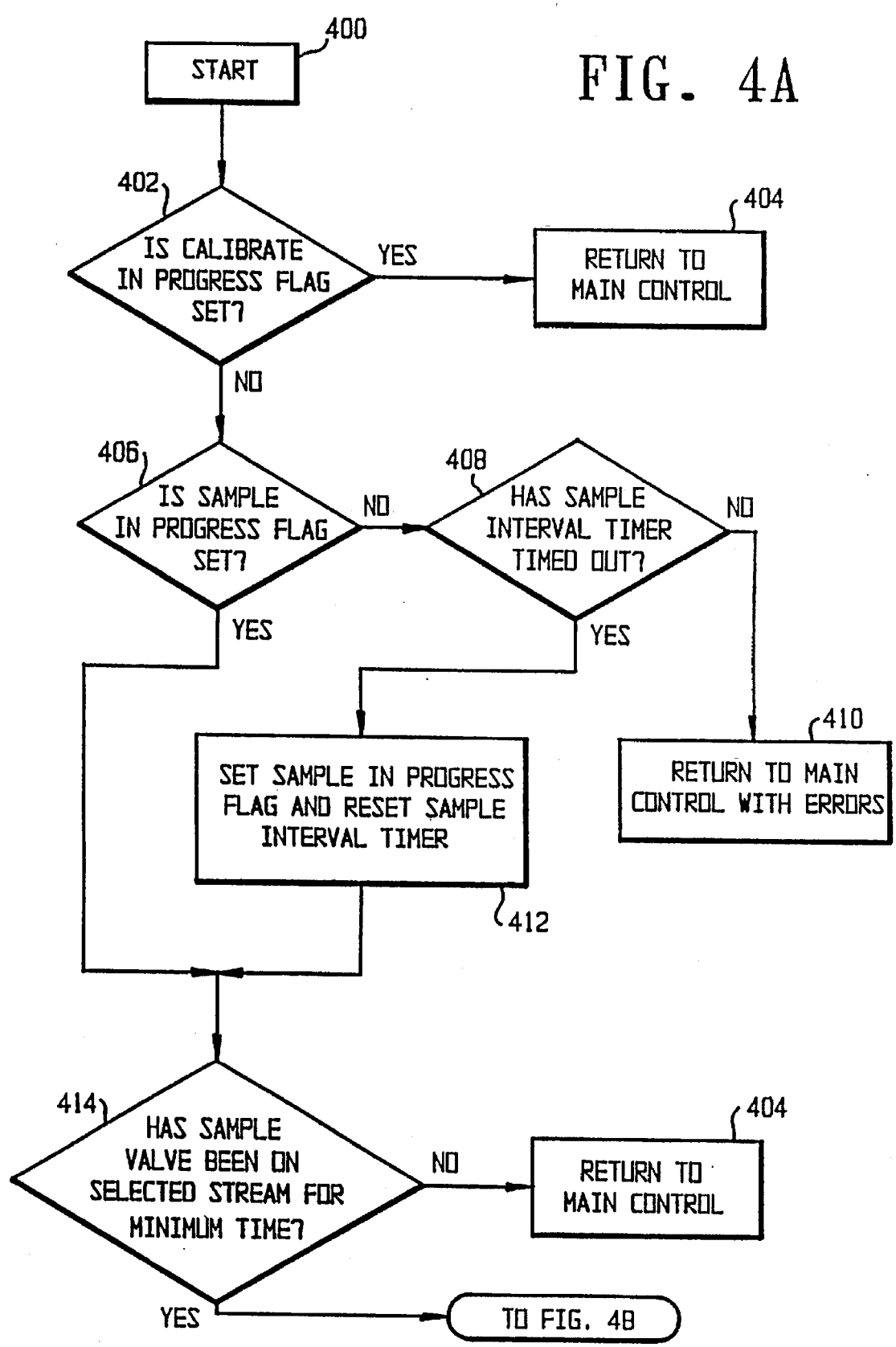
FIGS. 4A–4C are a flow chart illustrating the Gas Chromatograph Sample Routine program used with the system of the present invention.
Figure 4B:
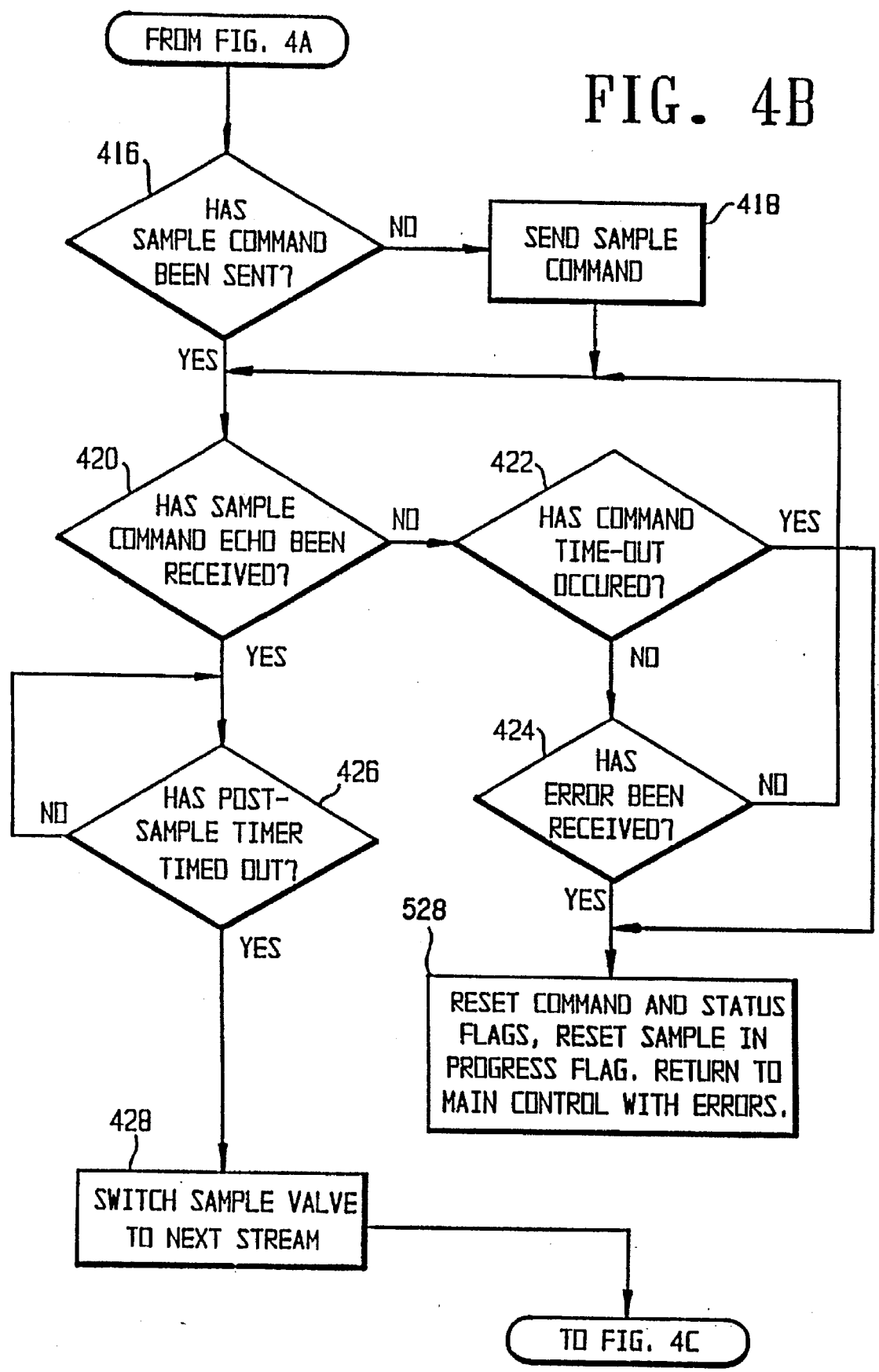
Figure 4C:
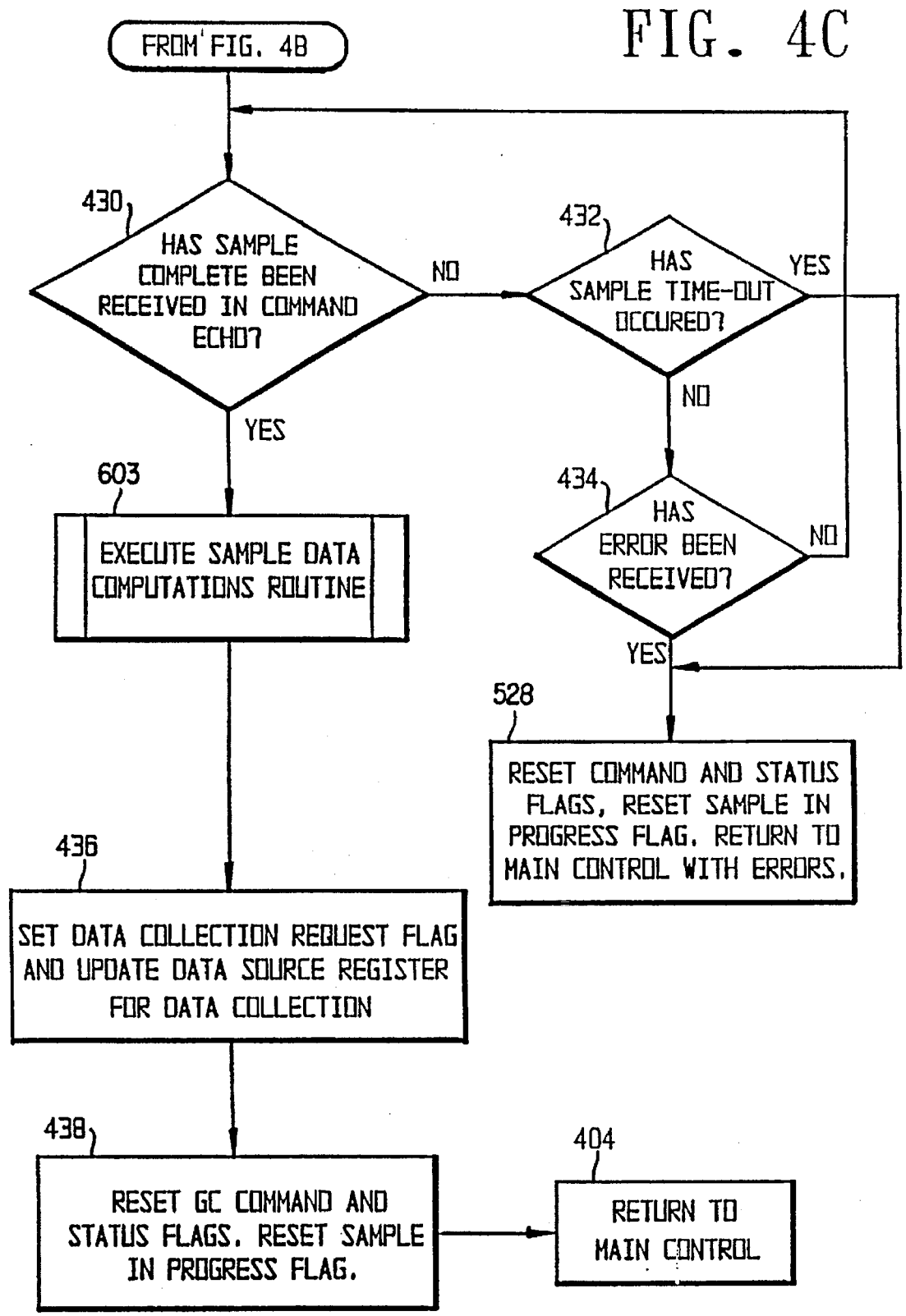
Figure 5A:
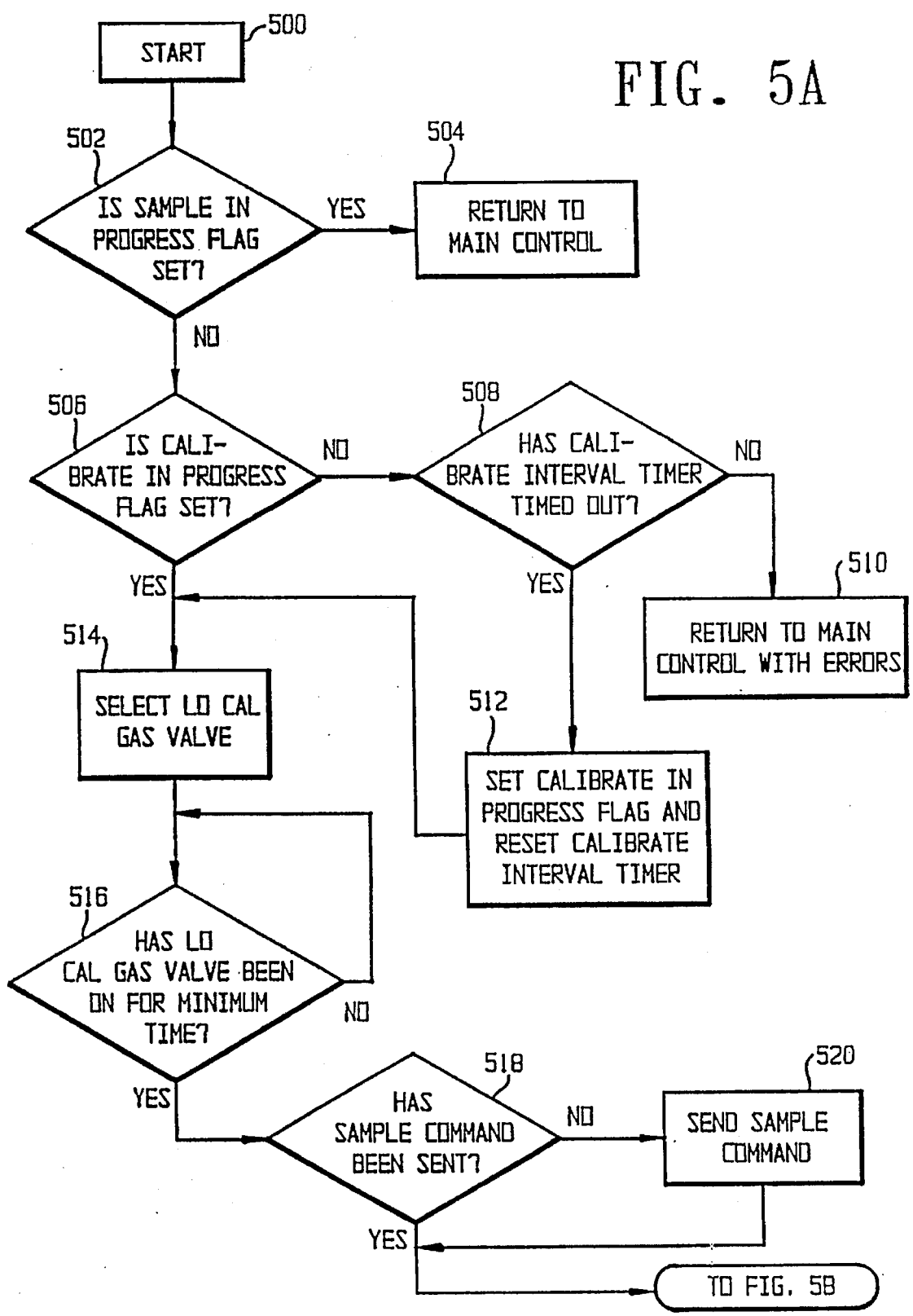
Figure 5B:
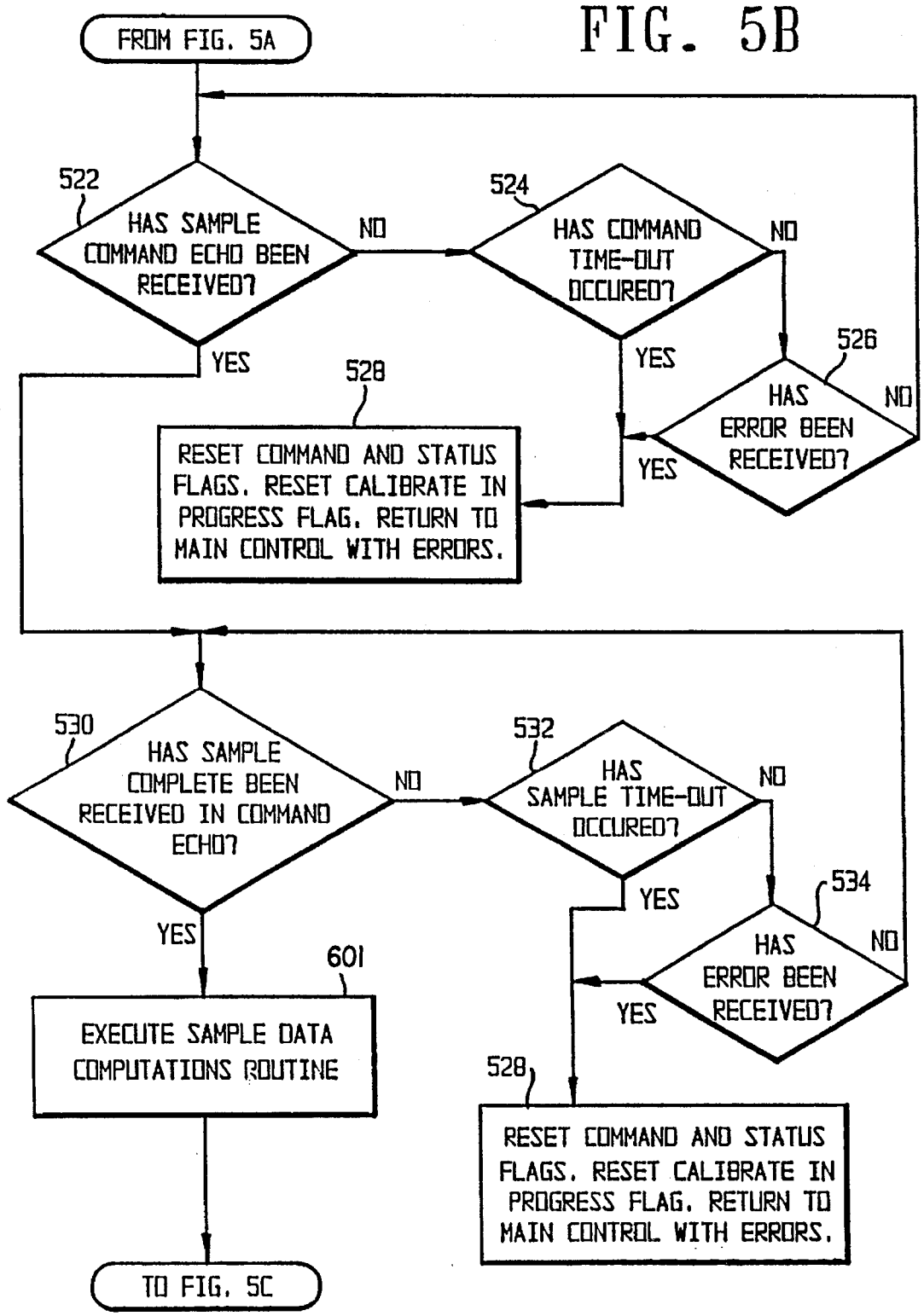
Figure 5C:
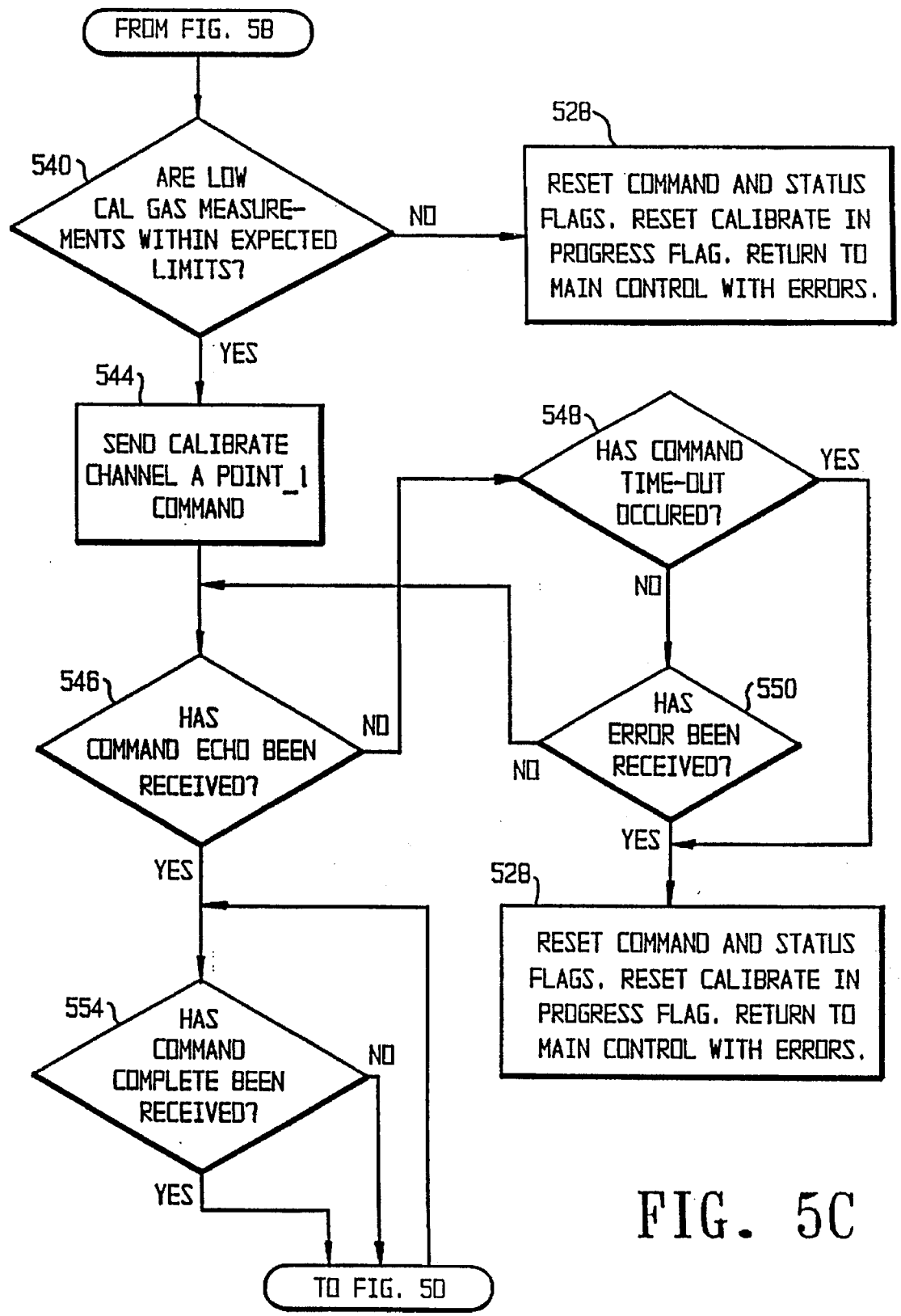
Figure 5D:
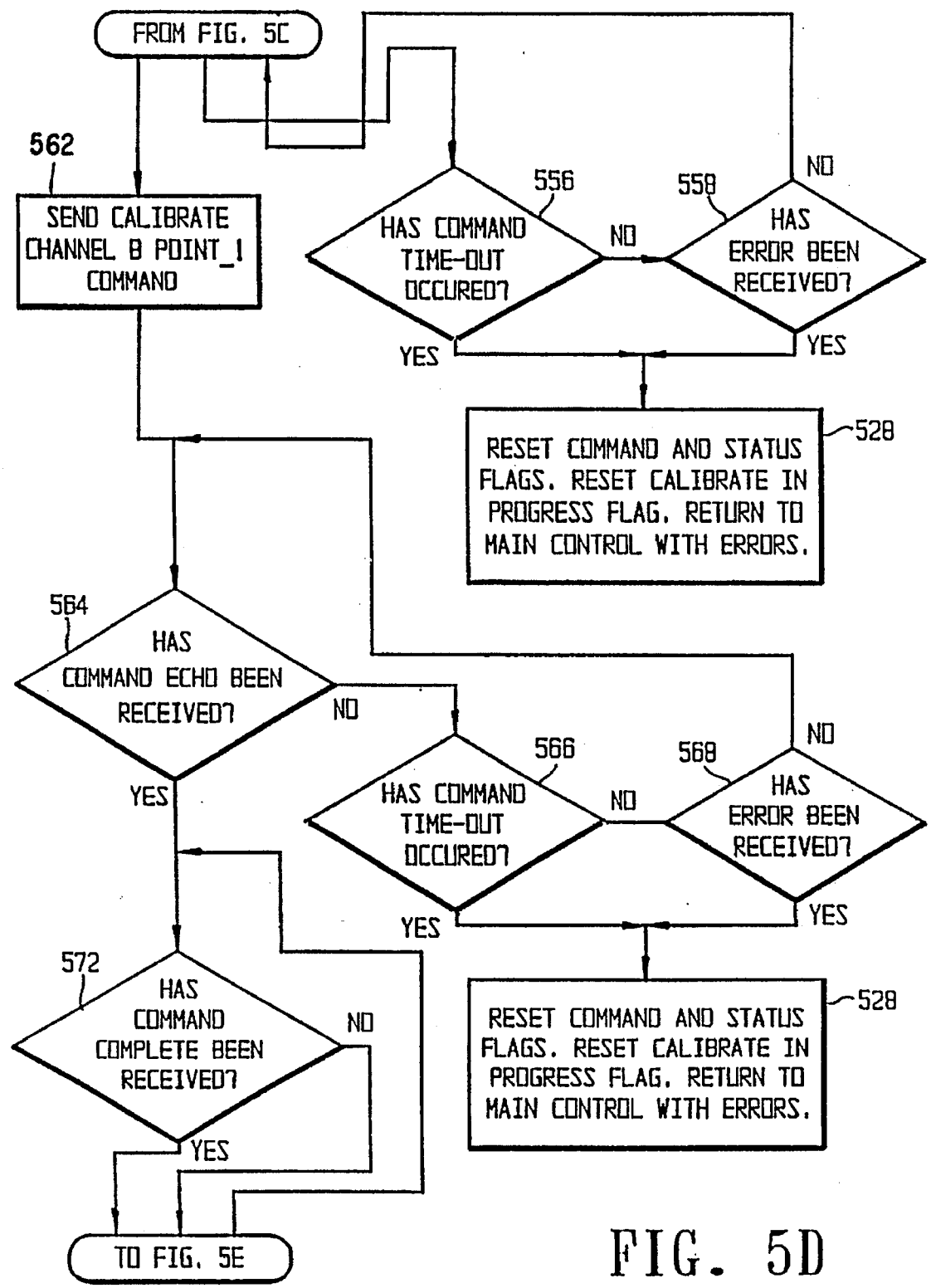
Figure 5E:
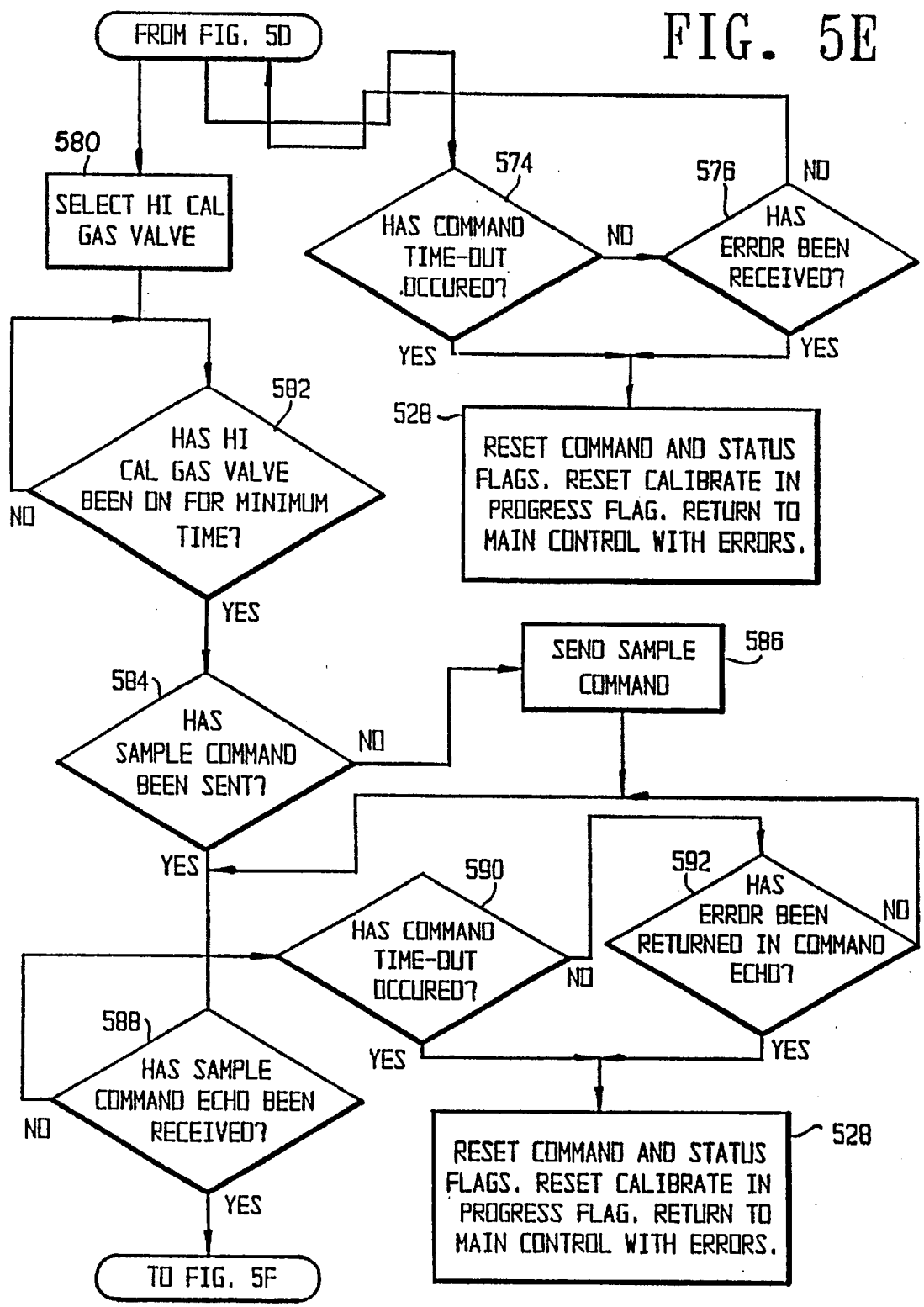
Figure 5F:
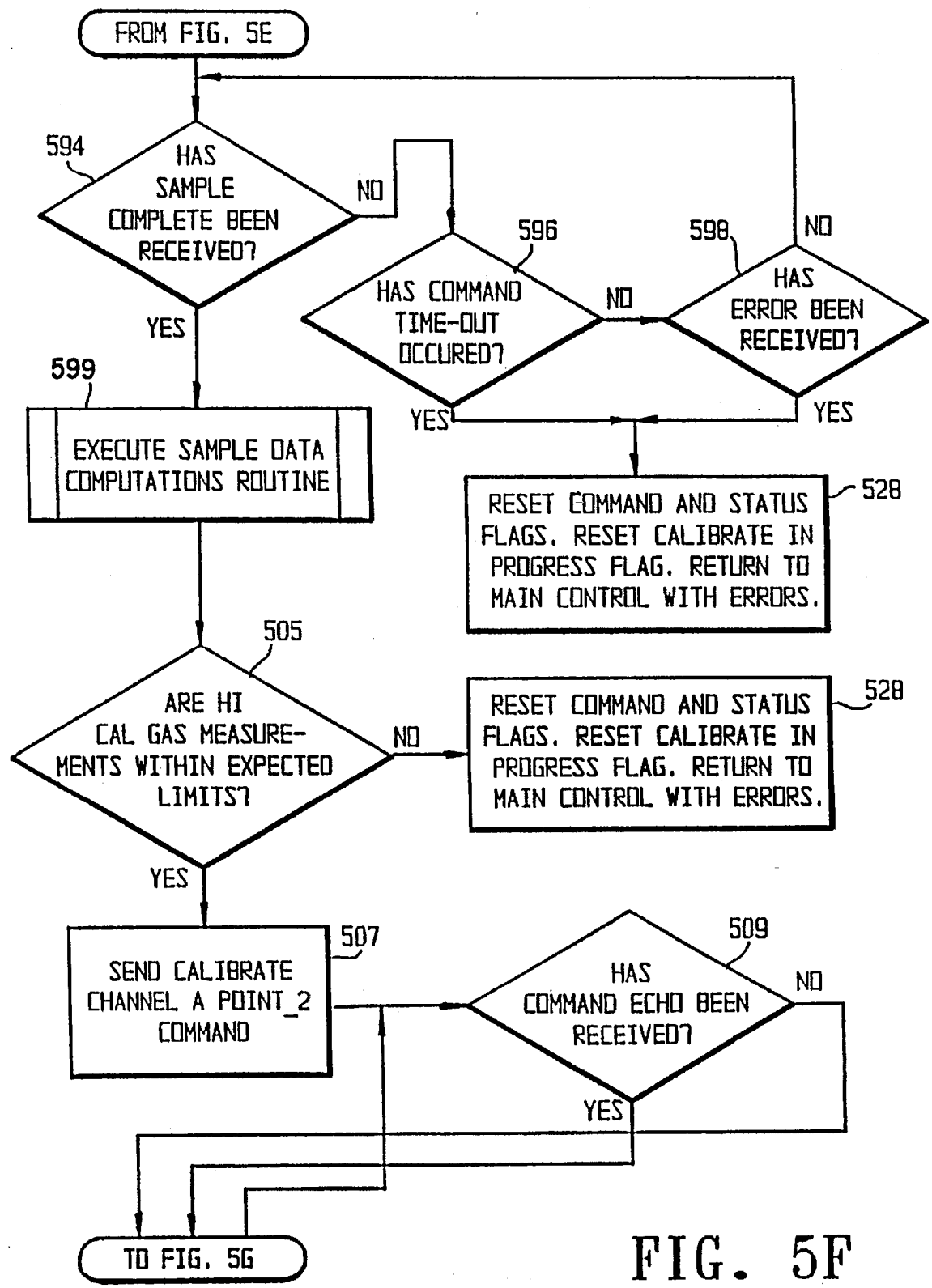
Figure 5H:
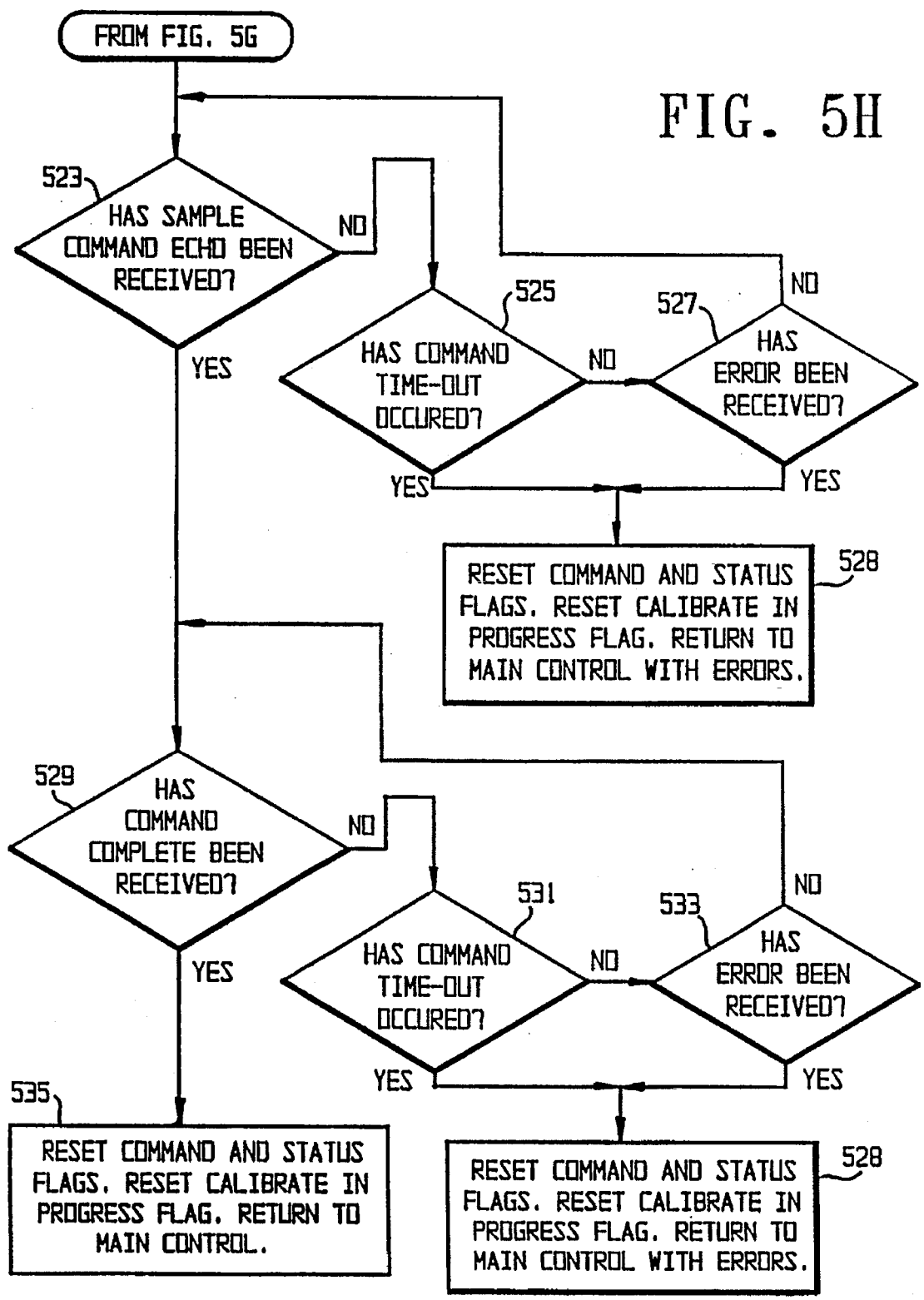

The GC Sample Routine, the flow chart of which is shown in FIGS. 4A–4C, will now be described.

When the GC Sample Routine is called from the main GC control program, it starts at step 400 and then determines whether a calibrate in progress flag is set at step 402. If an affirmative determination is made at step 402, meaning that the GC 114 is currently performing a calibration operation, then the GC Sample Routine returns to the main control program at step 404.

If it is determined at step 402 that a calibrate in progress flag is not set, then a determination is made of whether a sample in progress flag is set at step 406. If a negative determination is made at step 406, then a determination is made at step 408 of whether the sample interval timer has timed-out. If it is determined at step 408 that the sample interval timer has not timed-out, then the GC Sample Routine returns to the main GC control program with errors at step 410.

If it is determined at step 408 that the sample interval timer has timed-out, then a sample in progress flag is set and the sample interval timer is reset at step 412. After step 412 or in the event that an affirmative determination is made at step 406 that the sample in progress flag is set, then a determination is made at step 414 of whether the sample valve for the selected air stream has been on for a minimum period of time. If a negative determination is made at step 414, then the GC Sample Routine returns to the main GC control program at step 404.

If it is determined that the sample valve for the selected air stream has been on for a minimum period of time at step 414, then a determination is made at step 416 of whether a Sample command has been sent. If no Sample command is determined to have been sent at step 416, then a Sample command is sent at step 418. After an affirmative determination at step 416 and after step 418, a determination is then made of whether a Sample command echo has been received at step 420. If no Sample command echo is determined to have been received at step 420, then a determination is made at step 422 of whether the command timeout has occurred. If it is determined at step 422 that the command timeout has not occurred, then a determination is made at step 424 of whether an error has been received. If no error is determined to have been received at step 424, then step 420 is repeated again. If an affirmative determination is made at steps 422 or 424, then the command, status and sample in progress flags are reset and the GC Sample Routine returns to the main GC control program at step 528.

If an affirmative determination is made at step 420, indicating the confirmation of the receipt of the Sample command, then a determination is made at step 426 of whether the post-sample timer has timed-out. Step 426 is repeated until an affirmative determination that the post-sample timer has timed-out is obtained. Next, at step 428, the sample valve for the next air stream to be sampled is switched on. A determination is then made at step 430 of whether the Sample Complete signal has been received in the command echo. If a negative determination is made at step 430, then a determination is made at step 432 of whether the sample timeout has occurred. In the event that it is determined that the sample timeout has not yet occurred, then a determination is made at step 434 of whether an error has been received. If a determination is made at step 434 that an error has not been received, then step 430 is repeated. In the event that the sample timeout is determined to have occurred or it is determined that an error has been received, then the command, status and sample in progress flags are reset and the GC Sample Routine returns to the main GC control program with errors at step 528.

If an affirmative determination is made at step 430, then the sample data computations subroutine is executed at step 603. The data collection request flag is then set and the data source register is then updated for data collection at step 436. Next, the GC command, status and sample in progress flags are reset at step 438 and then the GC Sample Routine returns to the main GC control program at step 404.

Figure 6A:
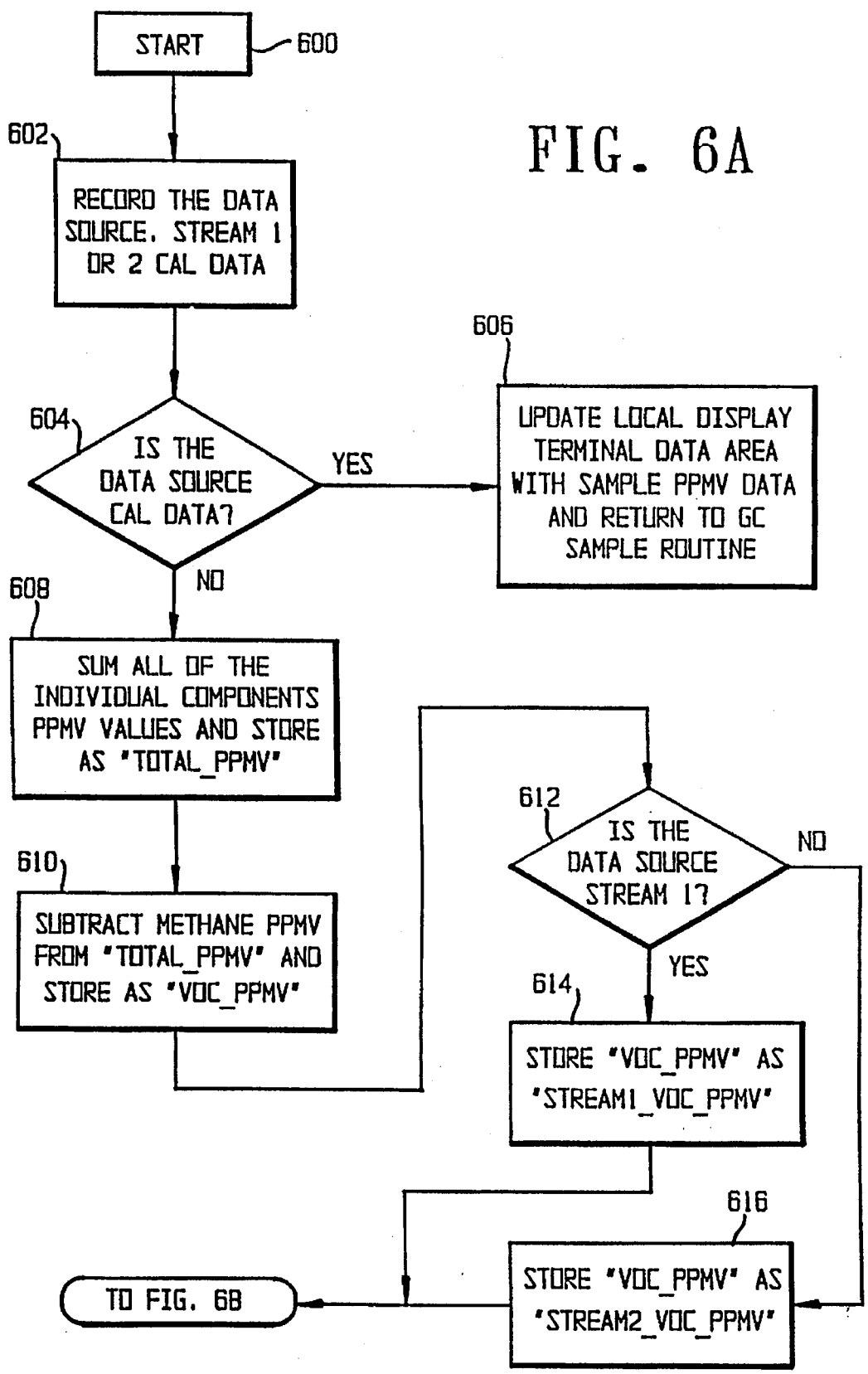
FIGS. 6A–6C are a flow chart illustrating the Sample Data Computations Routine software used with the system of the present invention.
Figure 6B:
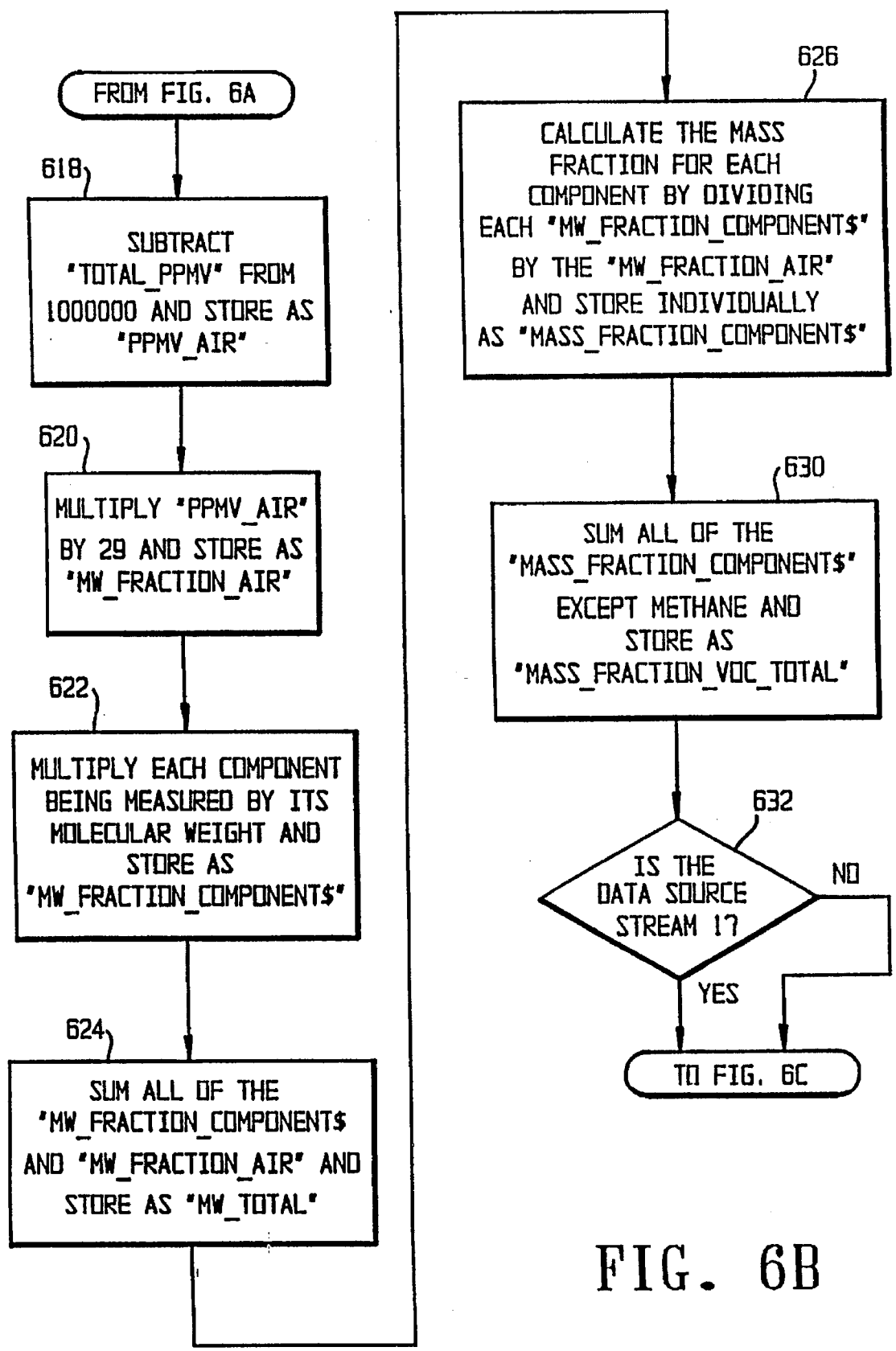
Figure 6C:
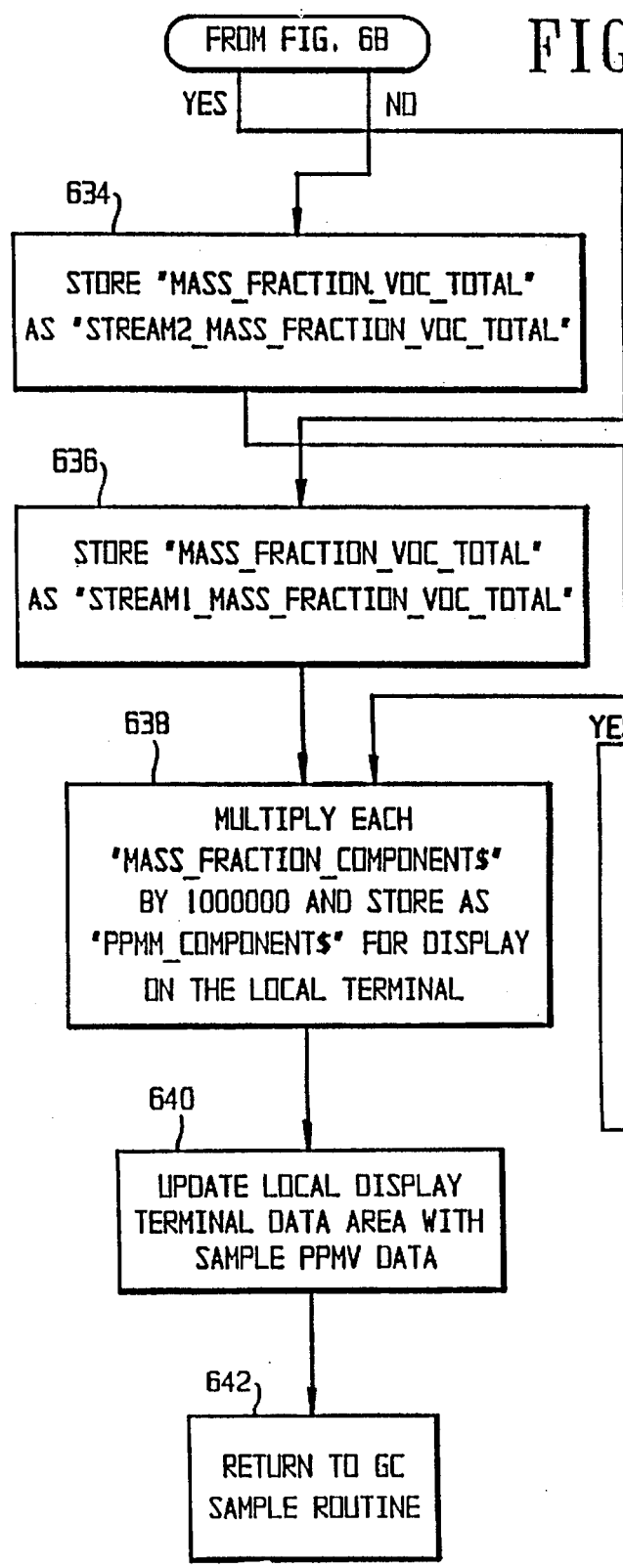
Figure 7A:
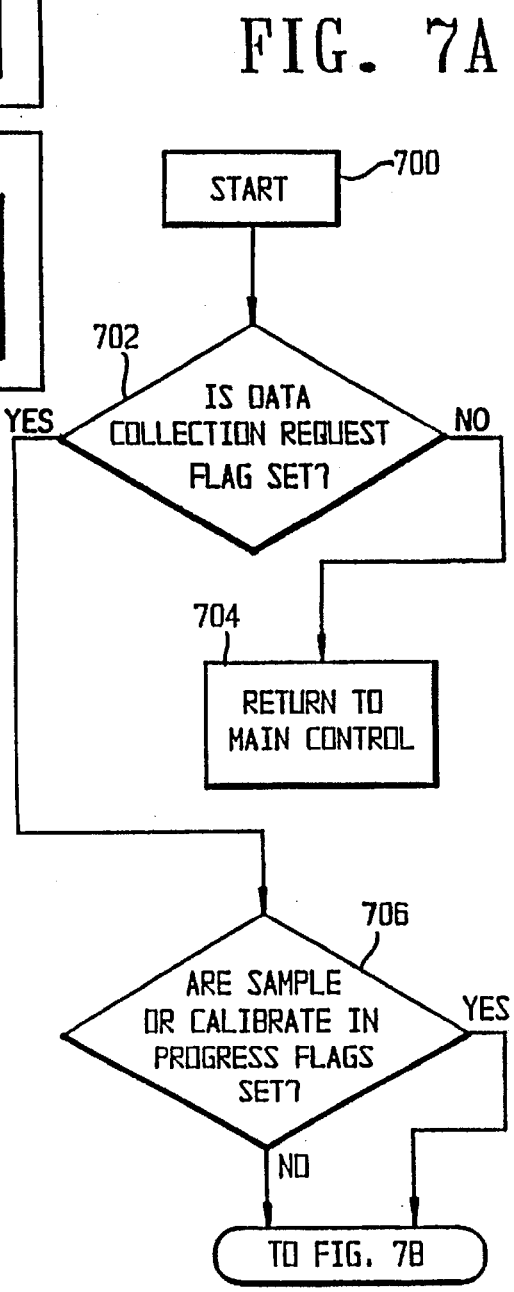
FIGS. 7A–7D are a flow chart illustrating the Data Collection Routine software used with the system of the present invention.
Figure 7B:
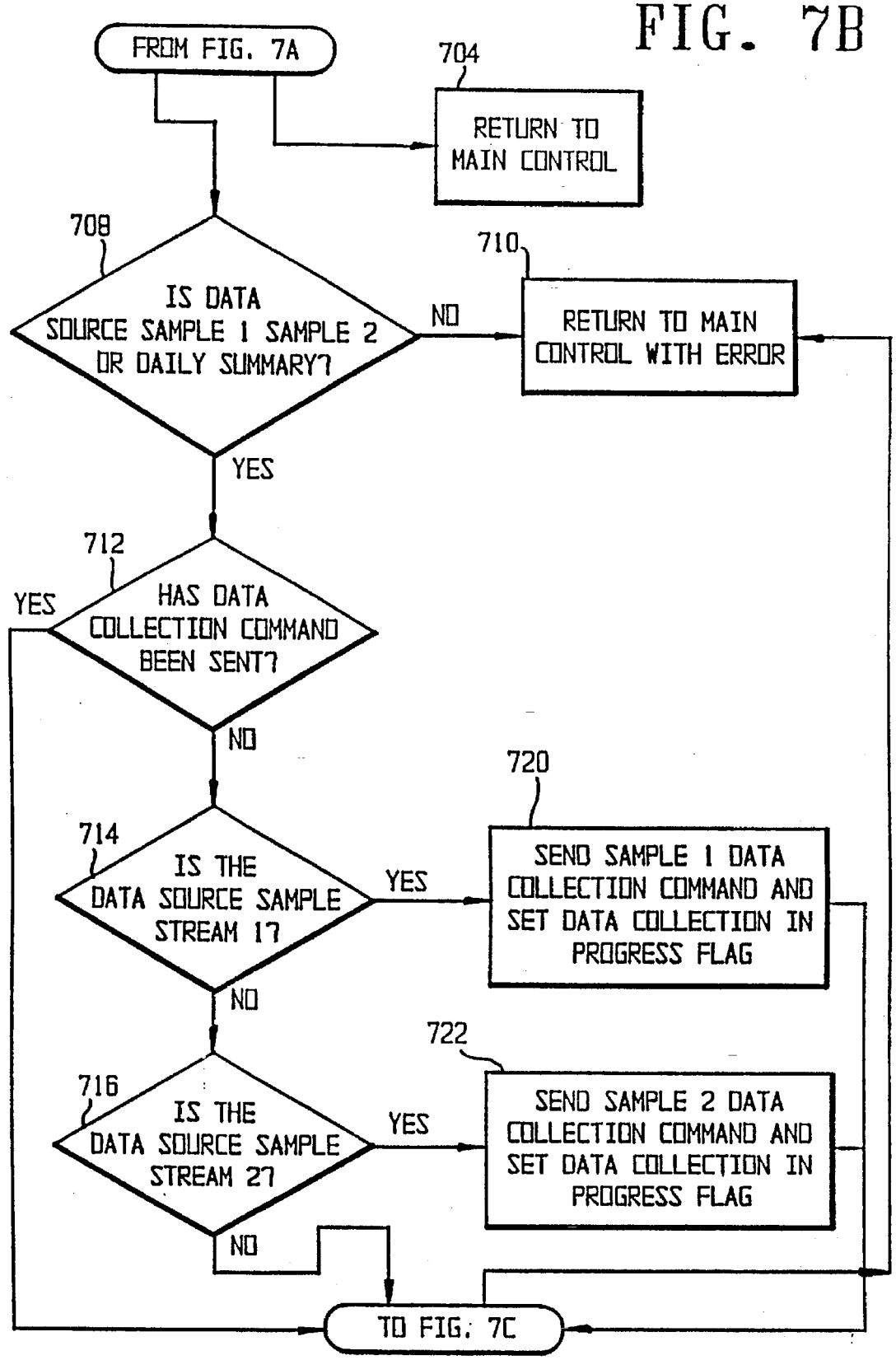
Figure 7C:
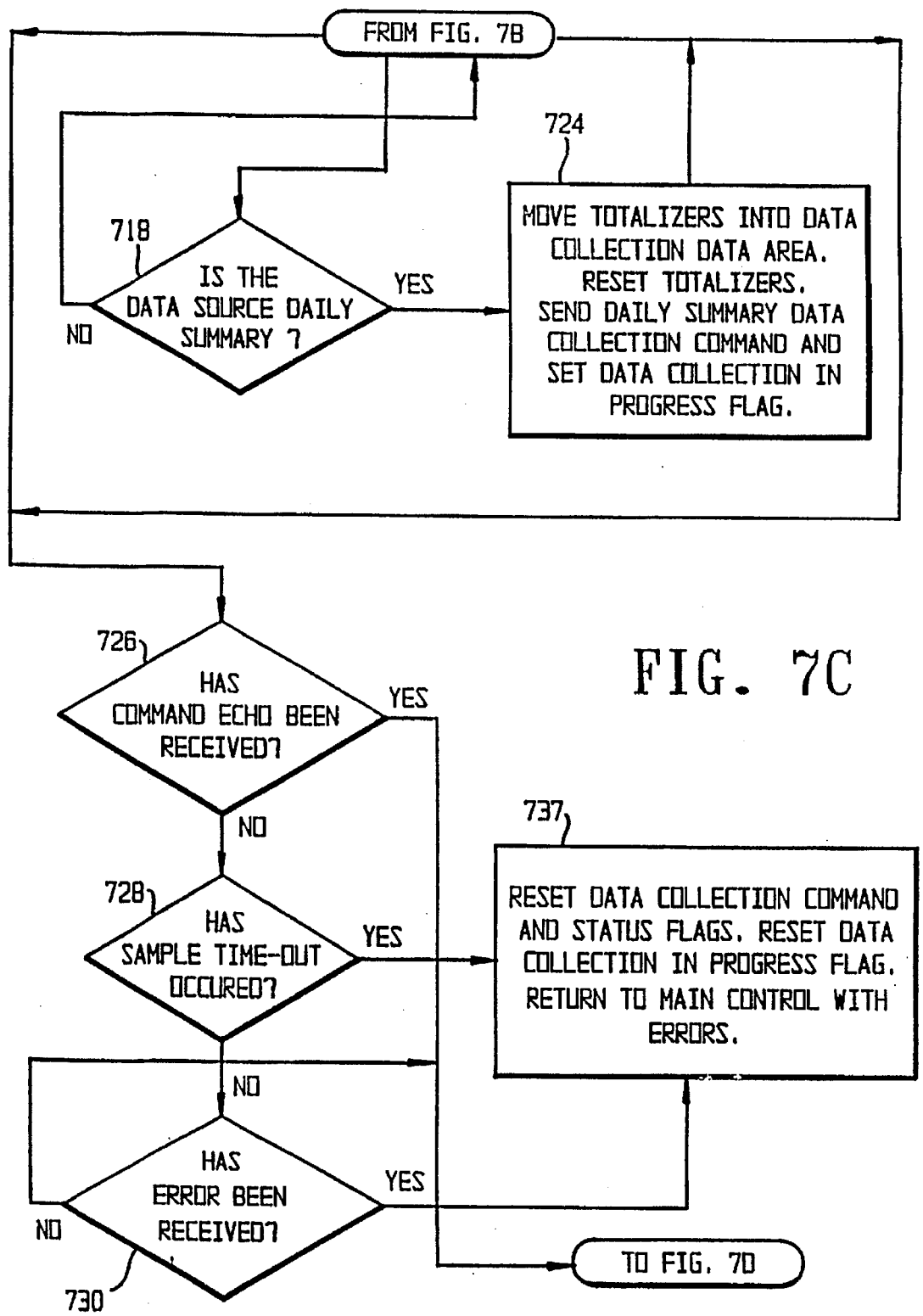
Figure 7D:
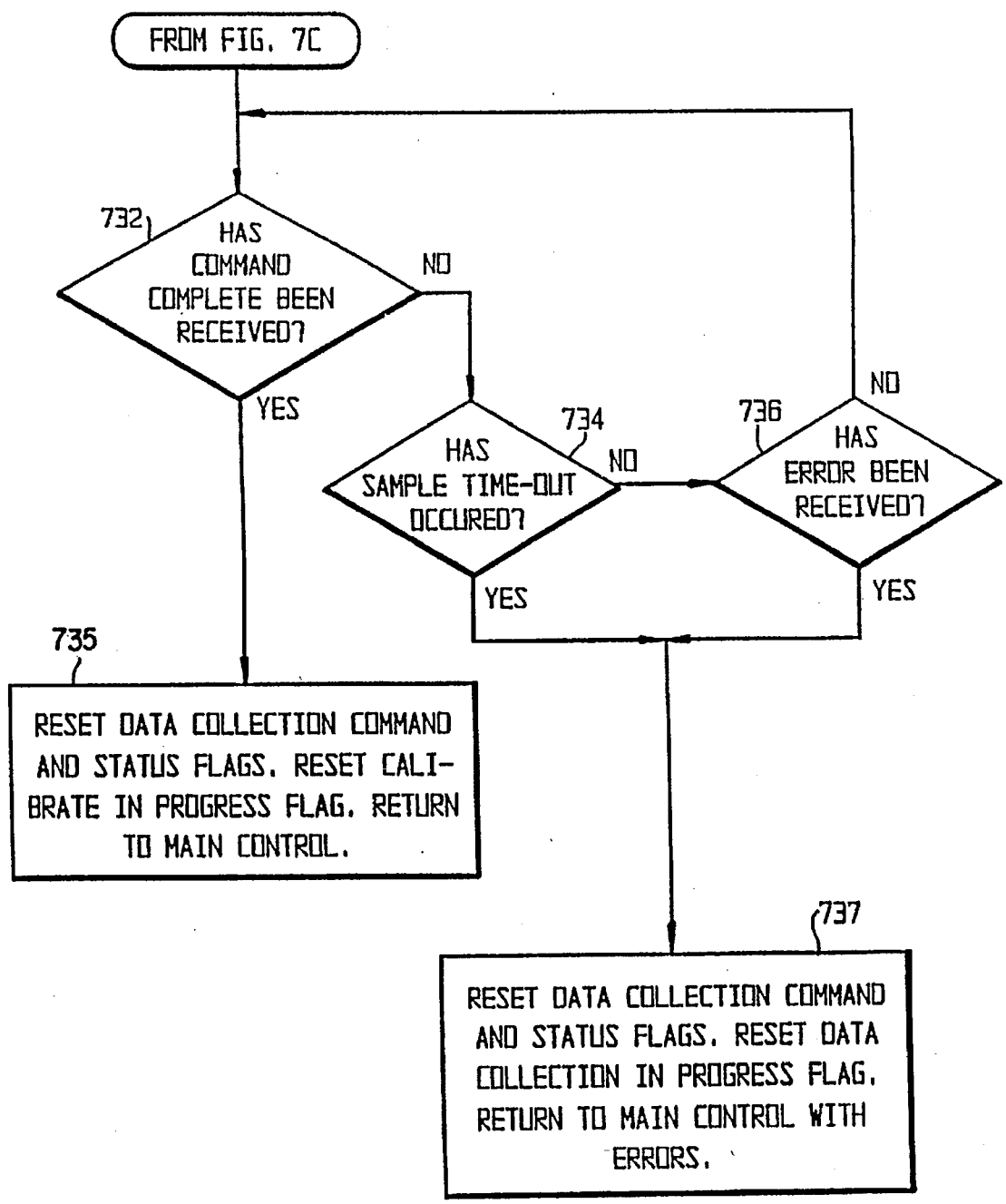

FIGS. 6A–6C illustrate a flow chart of the Sample Data Computations Routine called by the GC Sample Routine at step 600. When the Sample Data Computations Routine is called, it starts at step 600 and then records the data source and stream one, two, or calibration data at step 602. A determination is then made at step 604 of whether the data source is calibration data. If an affirmative determination is made at step 604, then the local display terminal data area is updated with the sample parts per million value (PPMV) data and the sample data computations routine returns to the GC Sample Routine, at step 606.

If a negative determination is made at step 604, indicating that the data source is an air stream to be sampled, then all of the individual components of the PPMV, at step 608 value are summed and stored as the value TOTAL_PPMV.

Next, at step 610, the methane PPMV is subtracted from the TOTAL_PPMV value and stored as the value VOC_PPMV. The methane is subtracted since it is not a regulated emission.

Then, at step 612, a determination is then made of whether the data source is the first stream to be measured. If an affirmative determination is made at step 612, then the value of VOC_PPMV, at step 614 is stored as STREAM 1_VOC_PPMV. If a negative determination is made as to step 612, then that same value is stored at STREAM 2_VOC_PPMV, at step 616.

After steps 614 and 616, the TOTAL_PPMV value is subtracted from one million and stored as the value PPMV_AIR, at step 618. Then, at step 620, the value PPMV_AIR is multiplied times 29 (the average molecular weight of air as defined by the EPA) and stored as the value MW_FRACTION_AIR. Next, at step 622, each component being measured is multiplied by its molecular weight and stored as MW_FRACTION_COMPONENT$. Then, at step 624, all of the MW_FRACTION_COMPONENT$ and all of the MW_FRACTION_AIR values are summed and the total stored as MW_TOTAL after step 624, at step 626, the mass fraction for each component is calculated by dividing each of the MW_FRACTION_COMPONENT$ values by the MW_FRACTION_AIR value and stored individually as the MASS_FRACTION_COMPONENT$ values.

Then, at step 630, all of the MASS_FRACTION_COMPONENT$ values except that for methane are summed and stored as the MASS_FRACTION_VOC_TOTAL. A determination is then made at step 632 of whether the data source is for stream one. If a negative determination is made at step 632, then the MASS_FRACTION_VOC_TOTAL is stored as STREAM 2_MASS_FRACTION_VOC_TOTAL, at step 634. If an affirmative determination is made at step 632, then that value is stored as STREAM 1_MASS_FRACTION_VOC_TOTAL, at step 636. Then, at step 638, each MASS_FRACTION_COMPONENT$ value is multiplied by one million and stored as PPMM_COMPONENT$ for display on the local CRT terminal 212. The local display terminal data area is then updated with the sample PPMV data at step 640 and then the sample data computations routine returns to the GC Sample Routine at step 642.

When the normal measure sequencing begins, the PLC 202 ensures that the first sample valve 130 has been open long enough to purge the sample lines and then writes a Measure Sample 1 command into its command buffer. The PC interface software module reads that command from the PLC and sends a Measure command to the GC control software module. The GC control software module then commands the GC 114 to execute a sample run. When the GC 114 acknowledges the command, the GC control software module sends the Acknowledge status to the PC interface software module which writes an Acknowledgement signal to the PLC 202 response buffer. The PLC 202 then closes the inlet air stream sample valve 130 and opens the discharge air stream sample valve 132 in preparation for the next sample.

When the GC 114 completes its measurements of the first sample, the GC control software module sends the results to the PC interface software module. The measured data is then logged to the historical database along with the appropriate sample line number, the real time clock and mass air flow data that was read at the time the measurement command was executed. The PC interface software module then writes a Command Complete command to the PLC 202 to inform it that it is acceptable to issue more commands.

Upon receiving the Command Complete command, the PLC 202 ensures that the discharge air stream sample valve 132 has been open long enough to purge the sample lines and then writes a Measure Sample 2 command into its command buffer. The PC interface software module reads that command from the PLC 202 and sends a Measure command to the GC control software module. The GC control software module then commands the GC 114 to execute a sample run. That command is then suitably acknowledged in the manner discussed above in connection with the first sample run.

After the PLC 202 determines that its response buffer has received an Acknowledgement signal, the PLC 202 then closes the discharge air stream sample valve 132 and then opens the input air stream sample valve 130 in preparation for the next sample. When the GC 114 completes its measurements of the discharge air stream sample, the GC control software module sends the results to the PC interface software module. The measured data is again logged to the historical database along with the sample line number, real time clock data and mass air flow data that was written at the time the Measure command was executed. The PC interface software module then writes a Command Complete command to the PLC 202 to inform it that it is acceptable to issue more commands.

The foregoing alternating sampling and measuring sequence is repeated until it is stopped by operator intervention or another scheduled calibration run occurs. The database maintained on the host computer 208 includes records of the GC 114 calibrations and measurements of sample streams, a record of all alarms and malfunctions pertinent to the operation of the absorber system 100 and a record of when the absorber system was in operation. All entries in the database have time and date information.

The database files that are generated from the data stored on the host computer 208 may be made available to the plant management information computer system (MICS) 218 (not shown) by way of a local area network interface or other suitable data/communication interconnection between the host computer 208 and the MICS 218. Obviously, such data may be displayed using the printer 210 or the CRT 212 connected to the host computer 208. The responsibility for database maintenance is given to the MICS computer 218, which reads the database files when scheduled and may function to purge data older than one month from the host computer 208. The MICS 218 is then responsible for long term archival of the data which is older than one month.

As will be recalled, the main GC control program also executes a Data Collection Routine at step 700, the flow chart of which is shown in FIGS. 7A–7D and will now be described. When called, the Data Collection Routine is started at 700 and a determination is then made of whether the data collection request flag is set at step 702. If an affirmative determination is made at step 702, a determination is then made at step 706 of whether the sample or calibrate in progress flags are set. If a negative determination is made at step 702 or an affirmative determination is made at step 706, then the Data Collection Routine returns to the main GC control program, at step 704.

If a negative determination is made at step 706, then a determination is made at step 708 of whether the data source is sample one, sample two or a daily summary. If a negative determination is made at step 708, then the Data Collection Routine returns to the main GC control program with an error message at step 710.

If an affirmative determination is made at step 708, then a determination is made at step 712 of whether the Data Collection command has been sent. If it is determined at step 712 that the Data Collection command has not been sent, then a determination is made at step 714 of whether the data source is sample stream one. If it is determined at step 714 that the data source is not the first sample stream, then a determination is made at step 716 of the whether the data source is the second sample stream. If it is determined at step 716 that the data source is not the second sample stream, then a determination is made at step 718 of whether the data source is the daily summary. If it is determined at step 718 that the data source is not the daily summary, then the Data Collection Routine returns to the main GC control program with an error message at step 710.

If an affirmative determination is made at steps 714 or 716, then the Sample Data Collection command for the respective sample (one or two) is sent and the data collection in progress flag is set, at steps 720 and 722 respectively. If an affirmative determination is made at step 718, then the totalizers are moved into the data collection area and then reset at step 724. The Daily Summary Data Collection command is then sent and the data collection in progress flag is set, also at step 724.

After steps 720–724 and after a determination at step 712 that the Data Collection command has been sent, a determination of whether a command echo has been received is then made at step 726. If a negative determination is made at step 726, then a determination is made at step 728 of whether the command timeout has occurred. If a determination is made at step 728 that the command timeout has not occurred, then a determination is made at step 730 of whether an error has been received. If no error has been determined to have been received at step 730, then step 732 is executed, as discussed below. Upon making an affirmative determination at steps 728 and 730, the Data Collection command, status and data collection in progress flags are reset and the Data Collection Routine returns to the main GC control program with error messages at step 737.

If a determination is made at step 726 that the command echo has been received, then a determination is made at step 732 of whether a Command Complete signal has been received. If an affirmative determination is made at step 732, then the Data Collection command, status and data collection in progress flags are reset and the Data Collection Routine then returns to the main GC control program at step 735.

If a negative determination is made at step 732, then a determination is made at step 734 of whether the command timeout has occurred. If it is determined at step 734 that the command timeout has not occurred, then a determination is made at step 736 of whether an error has been received. If a negative determination is made at step 736, then step 732 is repeated. If affirmative determinations are made at either of steps 734 and 736, then the Data Collection command, status and data collection in progress flags are reset and the Data Collection Routine returns to the main GC control program with errors at step 737.

The VOC peak reporting and the totalizer routines, executed at steps 320 and 322 from the main GC control program, will now be described. When the VOC peak recording routine is called, the STREAM 1_MASS_FRACTION_VOC_TOTAL value is multiplied by the AIR_FLOW_LBS/HR value and stored as the value STREAM 1_VOC_LBS/HR. The same calculation is performed on the STREAM 2_MASS_FRACTION_VOC_TOTAL value and the result stored as the value STREAM 2_VOC_LBS/HR. Also, the MASS_FRACTION_METHANE value is multiplied by the AIR_FLOW_LBS/HR value and stored as the METHANE_LBS/HR value. A determination is then made of whether the value of STREAM 1_VOC_LBS/HR is less than the STREAM 1_VOC_LBS/HR_PEAK value. If not, then the STREAM 1_VOC_LBS/HR value replaces the current STREAM 1_VOC_LBS/HR_PEAK value. After that, the same determination is made for the STREAM 2_VOC_LBS/HR and METHANE_LBS/HR value. Next, a determination is made of whether the STREAM 1_VOC_PPMV value is less than the STREAM 1_VOC_PPMV_PEAK value. If not, then the STREAM 1_VOC_PPM value replaces the STREAM 1_VOC_PPMV value. Again, a similar comparison is performed for the STREAM 2_VOC_PPMV and METHANE_PPMV values. Those computations comprise the VOC peak recording function. Those values are obtained from the sample data computations routine shown in FIGS. 6A–6.

The other function called from the main GC control is the totalizer function. When that function is called, a determination is first made of whether the value in the one second timer is true. If it is not, then the totalizer function returns to the main GC control program. If it is determined that the one second timer value is true, then that timer is first reset and then the STREAM 1_VOC_LBS/HR value is divided by 3600 and added to the STREAM 1_VOC_TOTALIZER value. The same division operation is applied to both the STREAM 2_VOC_LBS/HR and METHANE_LBS/HR values and the totalizer function then returns to the main GC control program. The emissions control system disclosed herein has been described in the context of measuring volatile organic compounds (VOC) which are emitted within the atmosphere of, for example, a printing plant. However, as will be obvious to those of ordinary skill in the art, the invention described herein can be utilized for the monitoring of other organic compounds emitted by different types of industrial users. Also, the software utilized with the emissions monitoring system disclosed herein can be resident on one or more computing devices, instead of the example described herein, which utilizes three separate, but interconnected, computing devices. As will also be obvious to those of ordinary skill in the art, the present invention can be readily modified to monitor more than two air streams.

As shown in FIGS. 9A–9B, the continuous emissions monitoring system (CEMS) of the present invention can be used to monitor/measure samples from a general process or from before and/or after a control device, such as the absorber system 100 shown in FIG. 1. The continuous emissions monitoring system of the present invention, the preferred embodiment of which is shown in FIGS. 9A–9B, can receive five or more samples by means of the five sample lines 912a–912e (only five sample lines are shown for purposes of simplicity) and can simultaneously monitor the air stream sample from any one of those sample lines 912a–912e by means of one or more of the gas chromatographic columns 114a–114n. Each of the gas chromatographic systems 114a–114n may preferably be the same gas chromatograph model as described in connection with the gas chromatograph 114.

As is well known to those of ordinary skill in the art, each of the chromatographic systems 114a–114n (and the gas chromatograph 114) represents a separation system composed generally of a sample introduction device/injector, an oven, a separation column and a detector. A plurality of different chromatographic systems 114a–114n may be used in place of the gas chromatograph 114 when it is desired to perform a multitude of different analyses on the same sample stream which cannot be accomplished on a single gas chromatograph. In that event, each of the separation columns and detectors which form a part of each of the chromatographic systems 114a–114n can be operated under the same or different conditions. For example, each chromatographic system 114a–114n can be operated at different temperatures, different linear flow velocities, etc.

In addition, since each of the chromatographic systems 114a–114n can be operated independently from the others, the nature of the separation column and the type of detector can be different for each of the multitude of chromatographic systems 114a–114n. For example, each of the chromatographic systems 114a–114n can utilize a different stationary phase film thickness, stationary phase chemical composition, separation column inner diameter and chemical composition. Also, the type of detector utilized with each of the chromatographic systems 114a–114n can be selected independently of the type of detector used in the other columns. For example, different types of detectors, such as a thermal conductivity detector (TAD), a flame ionization detector (FID) or a photo ionization detector (PID) can be utilized.

As is also well known to those of ordinary skill in the art, different chromatograms can be produced from the same sample mixture fed to one or more of the chromatographic systems 114a–114n. Different gas chromatograph columns can separate the same sample mixture differently, which results in the different chromatograms. It is also universally recognized that changing the operating parameters of a gas chromatographic column, such as the temperature and flow rate, can also affect the separation performed by that column. In addition, for any one set of chromatographic conditions (for example, column type, column length, stationary phase film thickness, temperature, column diameter and flow rates) the relative elution times of the components are constant and reproducible.

Therefore, the number and configuration of the chromatographic systems 114a–114n used with the continuous emission monitoring system of the present invention is dependent upon the compounds in the air stream that are to be measured. For example, for a certain plurality of compounds, only a single column, for example, column 114a, would perform the task for that separation since each of the components elute with unique elution times. Conversely, it may be necessary to operate more than one of the gas chromatographic systems (such as columns 114a and 114b) in order to obtain the desired results since some of the same components to be monitored might coelute on a single column.

Obviously, as the mix and number of compounds to be monitored change, the demand for using additional column configurations increases. In order to provide flexibility in operation, the continuous emissions monitoring system of the present invention can therefore be used with up to 50 sample streams and with up to 10 calibration streams.

Each of the air stream samples to be monitored is provided as an input to the continuous emissions monitoring system of the present invention, by means of each of the heated sample lines 912a–912e. It should be noted that the sample streams can also be drawn from ambient air and may contain volatile or semi-volatile organic or inorganic compounds. The sample streams may optionally be fed to a sample line integrity system 1000, which is shown and described in detail in connection with FIG. 10. Each of those heated sample lines 912a–912e then enters a heated valve enclosure 112a. Each of the sample lines 912a–912e is connected to a respective particulate filter such as a 4 micron filter 914a–914e contained within one portion of the heated valve enclosure 112a. The output from each of the filters 914a–914e is fed via respective heated sample lines 916 to a like number of pumps 910a–910e and from there, each sample is pumped by means of a like plurality of sample lines 918 as will be described hereafter.

The portion of the sample lines 918 which is outside of the heated enclosure is heated in a manner similar to the heated sample lines 916. In addition, each of the pumps 910a–910e, which may preferably be piston-type pressure pumps, deliver each of the samples into the sample lines 918 at a flow rate of preferably 2–4 liters per minute. In addition to heating the sample lines 912a–912e and 916 to 150 degrees C., the heads of each of the pumps 910a–910e are likewise heated to a temperature of 150 degrees C. The heated valve enclosure 112a is likewise heated to a temperature of 150 degrees C.

Most of the air stream samples in the gaseous phase which is moved through the system by each of the pumps 910a–910e is returned back to the process or stack from which the samples originated by a like plurality of sample return lines 144a–144e. Each of those sample lines, which are outside of the heated valve enclosure 112a, are heated to only 110 degrees C. since they receive the air stream after the analysis has taken place.

Each of the sample return lines 144a–144e includes a like plurality of needle valves or fixed flow restrictors 922a–922e which provide sufficient back pressure in the sample lines 918. By means of a two-position pneumatically-actuated solenoid microvalves 900a, 902a, 904a, 906a and 908a contained within the heated valve enclosure 112a and connected between the sample lines 918 and the sample return lines 144a–144e, a fixed portion of the sample in each of the lines is fed through a common manifold 920 and then to one or more of the gas chromatographic systems 114a–114n.

Each of the respective microvalves 900a–908a is operated by a respective pneumatic solenoid valve 900b–908b. The microvalves 900a–908a and the solenoid valves 900b–908b may preferably be the same parts as described in connection with the microvalve assemblies 128a, 134a, 136a and 138a and the pneumatic solenoid valves 128b, 134b, 136b and 138b described in connection with FIG. 8.

The sample diverted by each of the microvalve assemblies 900a–908a is fed to a common manifold 920. The manifold 920 is connected by means of a heated sample line 142 to the sample introduction system/injector of the gas chromatographic systems 114a–114n. Before reaching the heated sample line 142, the air stream sample exiting from the manifold 920 passes through a preferably 0.5 micron filter 924.

Although not shown in FIGS. 9A–B, each of the microvalve assemblies 900a–908a is fitted with a proximity sensor so that the identity of the open valve, and thus the sample stream feeding the common manifold 920, can be ascertained and verified using the software described later herein, by means of digital input/output signals. It should be noted that each of the filters 914a–914e and 924 is designed to be easily replaced.

After the sample exits from the filter 924, it passes through a 1/16 inch T coupling that couples each of the high calibrate 158, medium calibrate 159 and low calibrate 160 gas cylinders to the sample out line 126 from the heated valve enclosure 112a. The air stream sample then proceeds through the heated sample line 142 and into each of the gas chromatograph systems 114a–114n in parallel.

As discussed above, the gas chromatograph systems 114a–114n perform the separation and quantification operations of the continuous emission monitoring system of the present invention. A pressure sensor 926 is located in the sample line 142 in such a manner that the sample pressure entering the gas chromatographs is detected. Preferably, the detected sample pressure is typically about 5 pounds per square inch. The combination of the pressure sensor 926 and the proximity sensors verify both that there is a sample input into the gas chromatographic systems 114a–114n as well as identifying which sample is being input into those systems.

A small portion of the sample is introduced into each gas chromatographic injector, in a known manner. The remainder of the sample is returned to a common process stream through a vent return line 928 which is heated to only 110 degrees C., because the analysis of the sample contained within that line has already occurred.

While only three calibration gas cylinders and therefore different calibration gases 158–160 are shown, it is possible to utilize up to five or more calibration gas cylinders to calibrate the gas chromatographic systems 114a–114n. Each of the gas cylinders 158–160 is individually regulated and gauged to deliver the exact pressure as desired as detected in the sample stream by the pressure sensor 926. The pressure sensor 926 is utilized since pressure differences between the sample and calibration gases will result in quantification errors.

Each of the individual calibration gases 158–160 are introduced into the gas chromatographic systems 114a–114n by means of the two-position valve 930. When the valve 930 is open, all of the microvalve assemblies 900a–908a are closed and no process sample is allowed into the continuous emissions monitoring system. Under those conditions, any sample contained within the sample lines 912a–912e or, 916 or 918, is exhausted by means of the sample return lines 144a–144e. Obviously, as shown in FIG. 9A–B, and as described hereinafter, all of the valves utilized in the continuous emissions monitoring system of the present invention are electrically actuated under computer control.

The sample stream carried by the sample line 142 can be introduced into each of the separation systems 114a–114n by use of a single injector (not shown) for all of the columns or by individual injectors (not shown) used for each column. After the Sample stream enters each inlet port, the parallel processing, multi-column chromatographic system 192 is operated in the same manner as a single gas chromatographic system 114, with the major exception that a plurality of gas chromatographic systems 114a–114n are being controlled and monitored, instead of a single gas chromatograph 114. By introducing the sample stream into a plurality of gas chromatographic systems 114a–114n on a simultaneous basis, the sample stream can be rapidly analyzed as described above on a simultaneous basis.

The use of the parallel processing, multi-column chromatographic system 192 in place of the single gas chromatograph 114 used with the emissions monitoring system of FIG. 1, further provides the ability to analyze compounds of widely differing vapor pressures and chemical compositions contained in the sample streams on a simultaneous basis. As discussed above, chromatographic detectors of different selectivities can be used in each of the parallel chromatographic systems 114a–114n, which further enhances the ability of the parallel processing, multi-column chromatographic system 192 shown in FIGS. 9A–9B to rapidly analyze an input sample stream for a wide variety of different types of compounds that may be present in the sample stream. Also, the parallel processing system using the chromatographic columns 114a–114n shown in FIGS. 9A–9B provides the emissions monitoring system of the present invention with the ability to simultaneously measure a wide range of concentrations of individual compounds found in one or more sample streams.

Another benefit of the use of a number of parallel processing chromatographic systems 114a–114n shown in FIGS. 9A–9B as part of the continuous emissions monitoring system of the present invention is that both inorganic and organic compounds may be simultaneously analyzed by the use and selection of appropriate separation columns and conditions for operating those columns, together with the appropriate selection of the chromatographic detectors. The only limitation in the operation of such a system to measure and analyze the various compounds contained within a sample stream is that the compounds to be measured and analyzed must have an appropriate vapor pressure for gas chromatographic analysis.

As will be obvious to those having ordinary skill in the art, the parallel processing multi-column chromatographic system 192 using a number of chromatographic columns 114a–114n shown in FIGS. 9A–9B results in a continuous emissions monitoring system having the ability, using a stream selector module and the associated electronics and valves shown in conjunction with that stream selector module, to monitor up to 50 sample streams and 10 calibration streams.

A mass flow measurement device 108, such as that available from Kurz Instruments of Monterey, CA as Model No. 4500 Mass Flow System may be used in the process stream to determine the total flow of the sample stream prior to the processing of the sample stream by the chromatographic systems 114a–114n. The mass flow measurement system allows for the conversion of the concentration as measured by the parallel processing, multi-column chromatographic system 192 to weight, such as in units of pounds or pounds/unit time.

The emissions monitoring system shown in FIGS. 1 and 9A–9B may also be operated in such a manner to ensure that the process stream sample analyzed by the gas chromatograph 114 or the parallel processing, multi-column chromatographic system 192 is not chemically or physically altered by the measurement hardware. That is, a system is provided such that the integrity of the measurement system and sample lines is measured and maintained.

The apparatus for ensuring that the analyzed process stream samples are not chemically or physically altered is shown in FIG. 10 and is described in connection with the continuous emissions monitoring system shown in FIGS. 9A–9B. The process stream sample integrity system 110 is connected to each sample air stream line 912a–912e at the same point that a portion of the sample stream is diverted to the continuous emissions monitoring system. The sample stream outputs from the process stream integrity system 194 are connected to the respective sample filters 914a–914e. In addition, the process stream sample integrity system 194 provides data outputs to the emissions monitoring control system 200a shown in FIG. 2B.

As shown in FIG. 10, a compressed gas cylinder 188, which contains a gas or a mixture of gases that can be supplied to the hardware of the process stream sample integrity system 1000 and that can also be analyzed by the chromatographic system 192, such as 1000 PPM methane in air, is utilized for monitoring the integrity of the sample lines and the measurement system. A heated three-way valve 170 receives each respective process sample stream either before or after, for example, the absorber system 100. The output of the heated three-way valve 170 is connected to both the sample line and to the integrity measurement hardware. In its normal operating position, the three-way valve 170 allows airflow to pass from the process stream to the stream selector module, the hardware of which is shown and described in connection with FIGS. 9A–9B herein.

When a measurement system integrity test is to be conducted, the three-way valve 170 is placed in an alternate position, which causes the shut-off of the respective process stream flow through the valve 170 and allows the flow of the supply gas from the compressed gas cylinder 188 to be supplied to the stream selector module of the continuous emissions monitoring system of FIGS. 9A–9B.

In the measurement system integrity test position, the supply gas contained in the compressed gas cylinder 188 is supplied to the remaining components of the process stream sample integrity system 1000 as shown in FIG. 10 through a regulator and gauge 186. The gauge 186 is connected to a needle valve 184 which functions to regulate the flow of the supply gas. The output from the needle valve 184 is connected to a two-way multiport on-off valve 182. The supply gas is then directed to an open split interface 176, through the heated 3-way valve 170 and then into the respective one of the sample lines 912a–912e.

Sufficient flow without an increase in system pressure is assured by detection of a small, positive flow using the flow indicator 178 which is connected to the open split interface 176. The data output from the flow indicator 178 is supplied to the continuous emissions monitoring control system 200a. The pressure of the gas supply is maintained at or near atmospheric pressure as it proceeds to the heated 3-way valve 170.

The heated 3-way valve 170 may preferably be model no. A4C6WP, available from Valco Instrument Company, of Houston, Tex. The flow indicator 178 may preferably be a CO-25 PS1 pressure transmitter from Wika, of Hauppauge, N.Y.

By incorporating the process stream sample integrity system 1000 of FIG. 10 as part of the continuous emissions monitoring system of the present invention, the measurement of all flows within the continuous emission monitoring system, such as that of the calibration gases, sample gas, sample line integrity gas, flows into and out of the stream selector module and parallel processing, multi-column chromatographic system 192, can be measured and stored in the continuous emissions monitoring control system 200a used with the present invention. By performing this test periodically, the integrity of the system during the analyses performed by the system can be guaranteed.

As will be obvious to those of ordinary skill in the art, the process sample stream integrity system 1000 shown and described in the connection with FIG. 10 is controlled by the continuous emissions monitoring control system 200 and the components thereof shown and described in more detail in connection with FIG. 2B. In addition, the data measured by the continuous emission control system described herein, including the parallel processing, multi-column chromatographic system 192 and the process stream sample integrity system 1000, may be stored in a data base that records all flows, concentrations and other system conditions. Obviously, a number of the sample stream integrity systems 1000 is required for use with the continuous emissions monitoring system of the present invention, one for each of the sample lines 912a–912e, as shown in FIGS. 9A–9B.

The software for controlling the continuous emissions monitoring system of the present invention is shown in flow chart form in FIGS. 11A–11C, 12A–12C and 13A–13D. The CEMS control software shown in those figures is used on an 80486, 50 megahertz supervisor computer 250 which is connected to an EISA bus. The chromatography software discussed above, EZChrom, is used to run the chromatographic system 192. The chromatography software is used on an 80386, 33 megahertz computer 252a which resides on the same EISA bus as the supervisor computer and which communicates with the supervisor computer by means of Dynamic Data Exchange (DDE). A diagram of the continuous emissions monitoring control system 200a used to operate the continuous emissions monitoring system shown in diagrammatic form in FIGS. 9A–9B and 10 is shown in FIG. 2B.

Figure 12A:
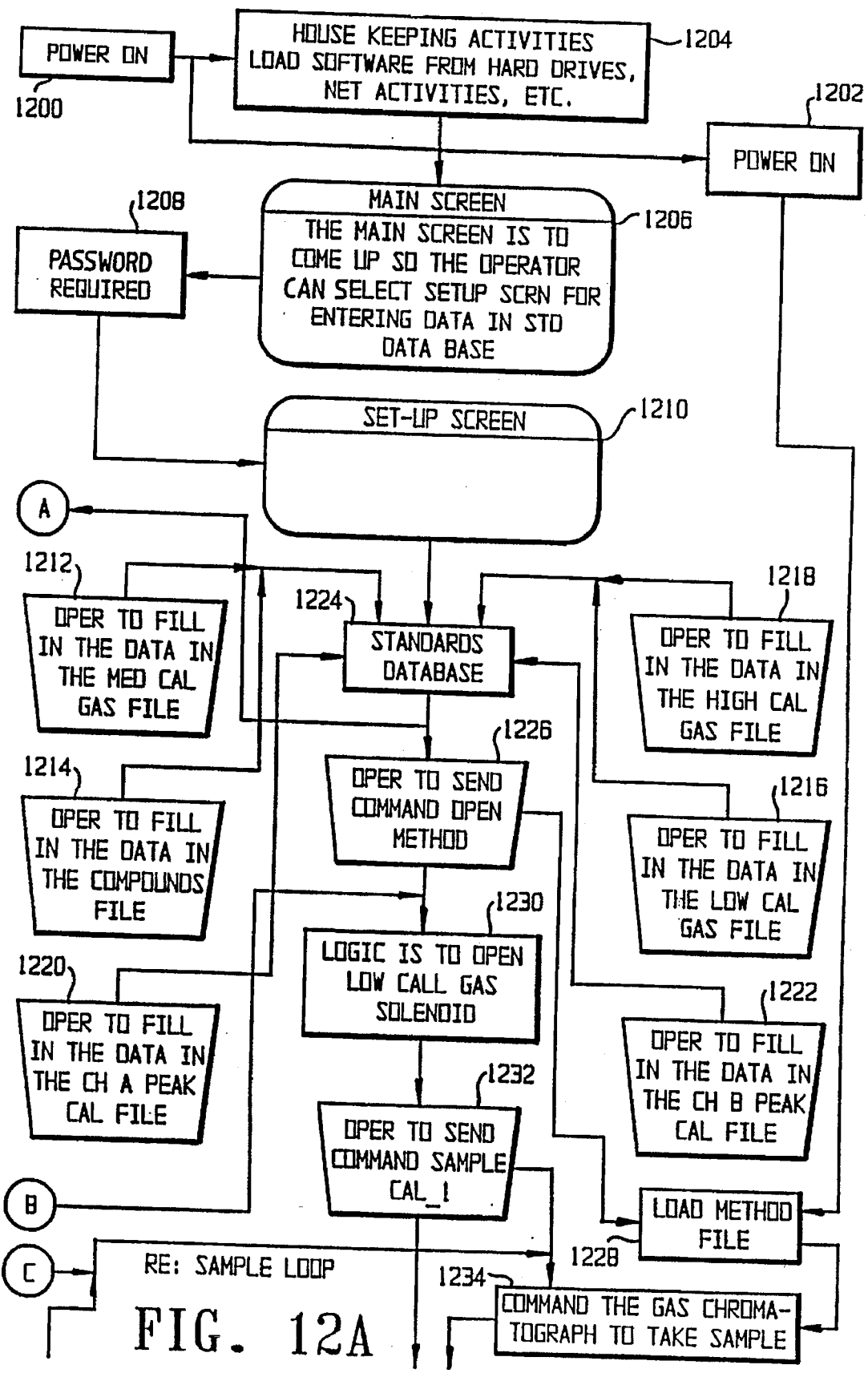
FIGS. 12A–12C are a flow chart illustrating the Main Sequence Calibration Routine used with the system of the present invention illustrated in FIGS. 2B, 9 and 10.
Figure 12B:
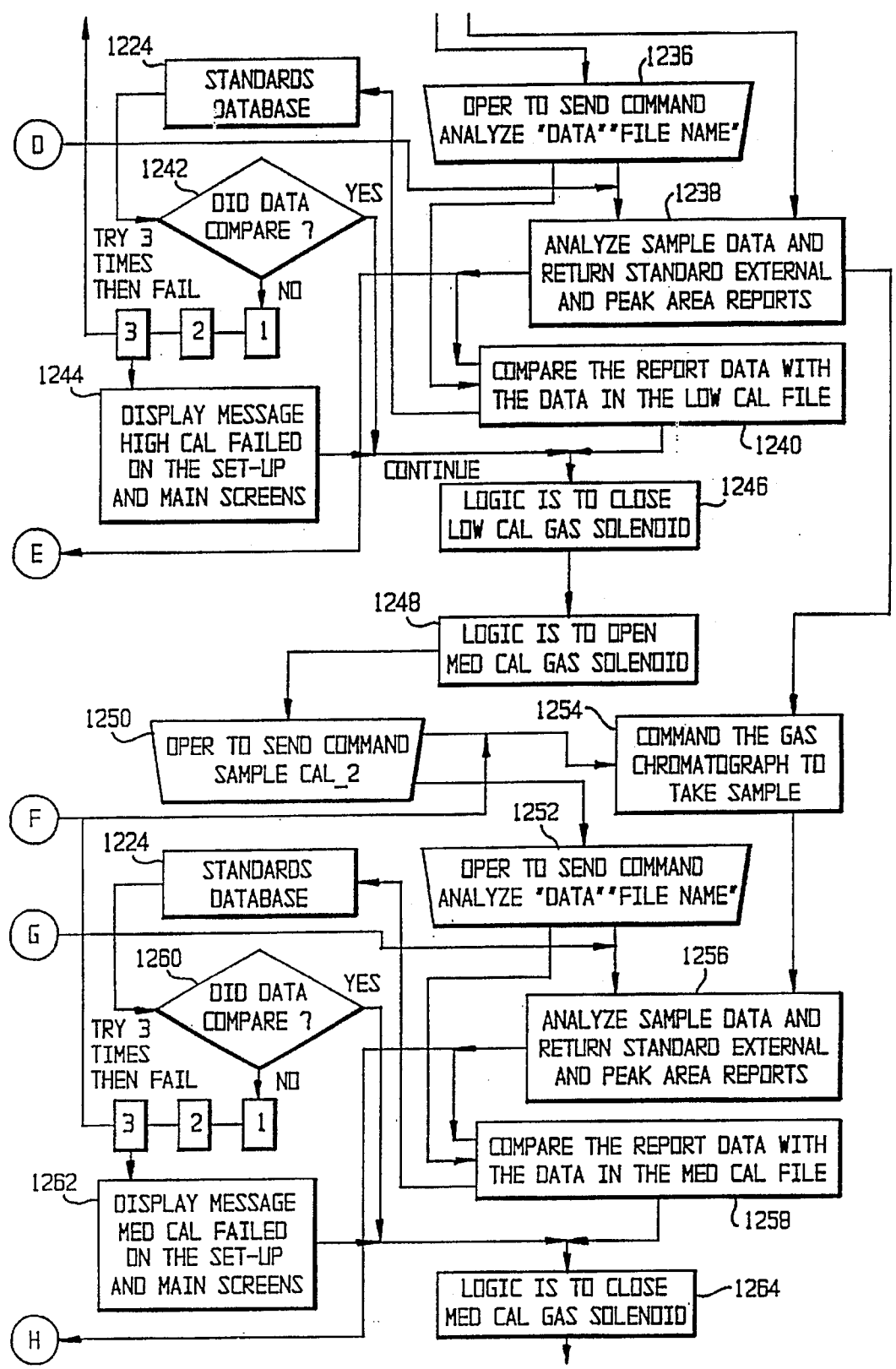
Figure 12C:
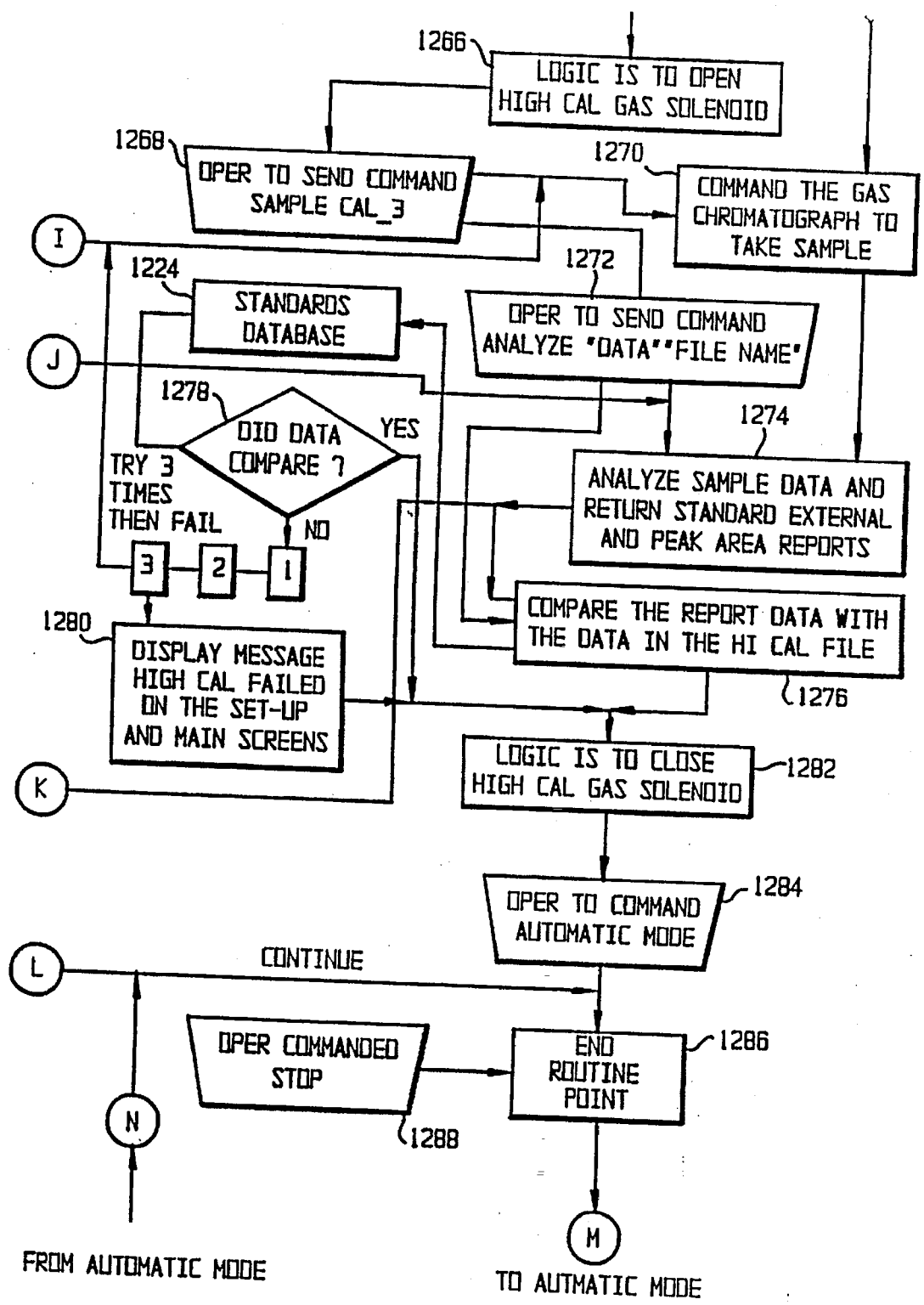

FIGS. 12A–12C show in flow chart form the Main Sequence Calibrate Routine of the continuous emissions monitoring system control software and its interaction with the EZChrom computer on which the EZChrom software operates. While only two computers to operate eight GC's 114a–114n are utilized in this embodiment, additional computers could be utilized in the event that more than eight GC's are used. Initially, the supervisor computer is powered on at step 1200 and then the GC or EZChrom computer is powered on at step 1202. At step 1204, various housekeeping activities occur on the supervisor computer, such as the loading of software from the computer hard drives into the computer memory, certain activities associated with the network, etc. The main screen is then shown to the operator at step 1206. The main screen comes up so that the operator can select an appropriate set up screen for entering the data to create the Standards Database which will be used later in the program.

Figure 11A:
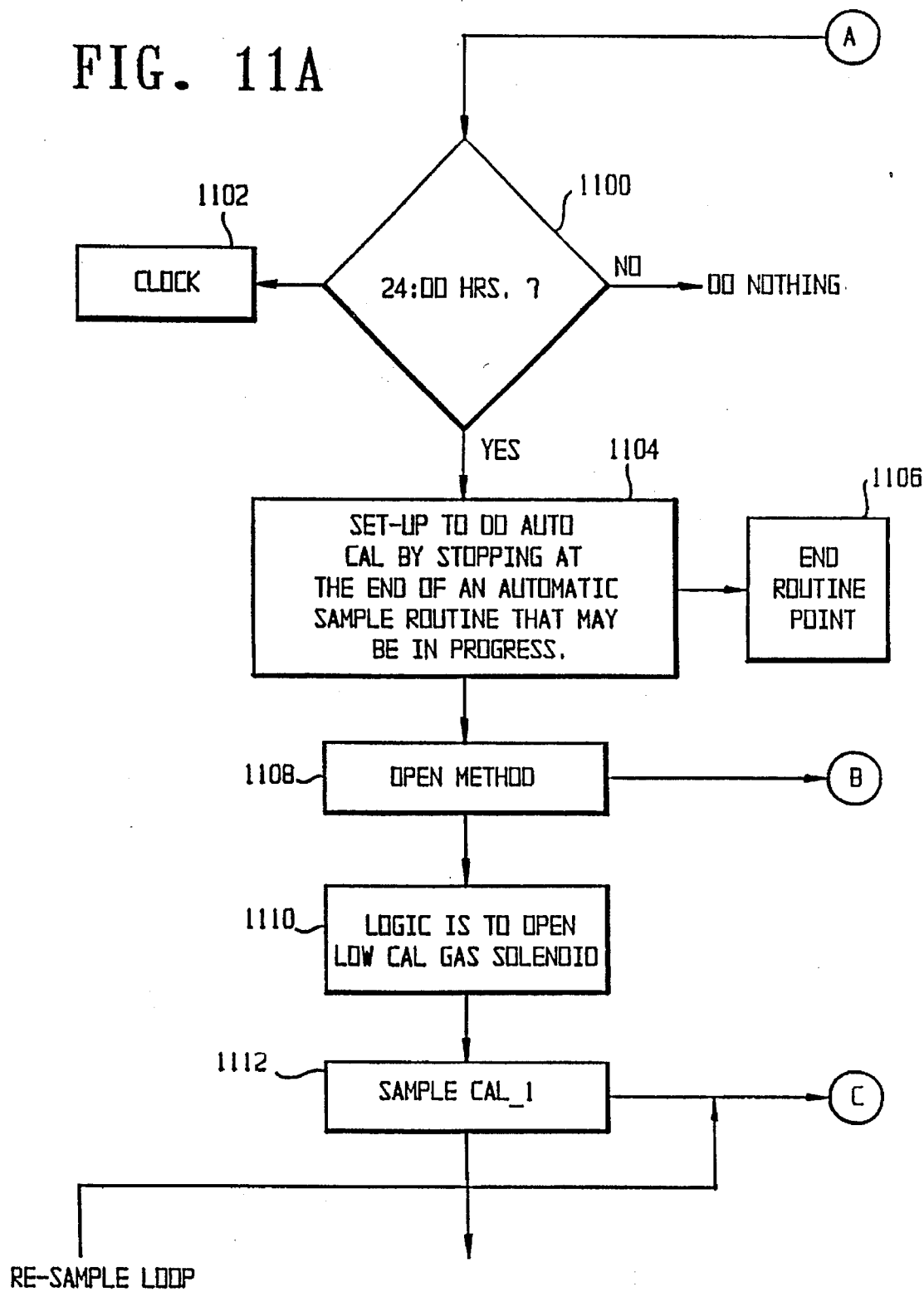
FIGS. 11A–11C are a flow chart illustrating the Automatic Calibration Routine used the system of the present invention illustrated in FIGS. 2B, 9 and 10.
Figure 11B:
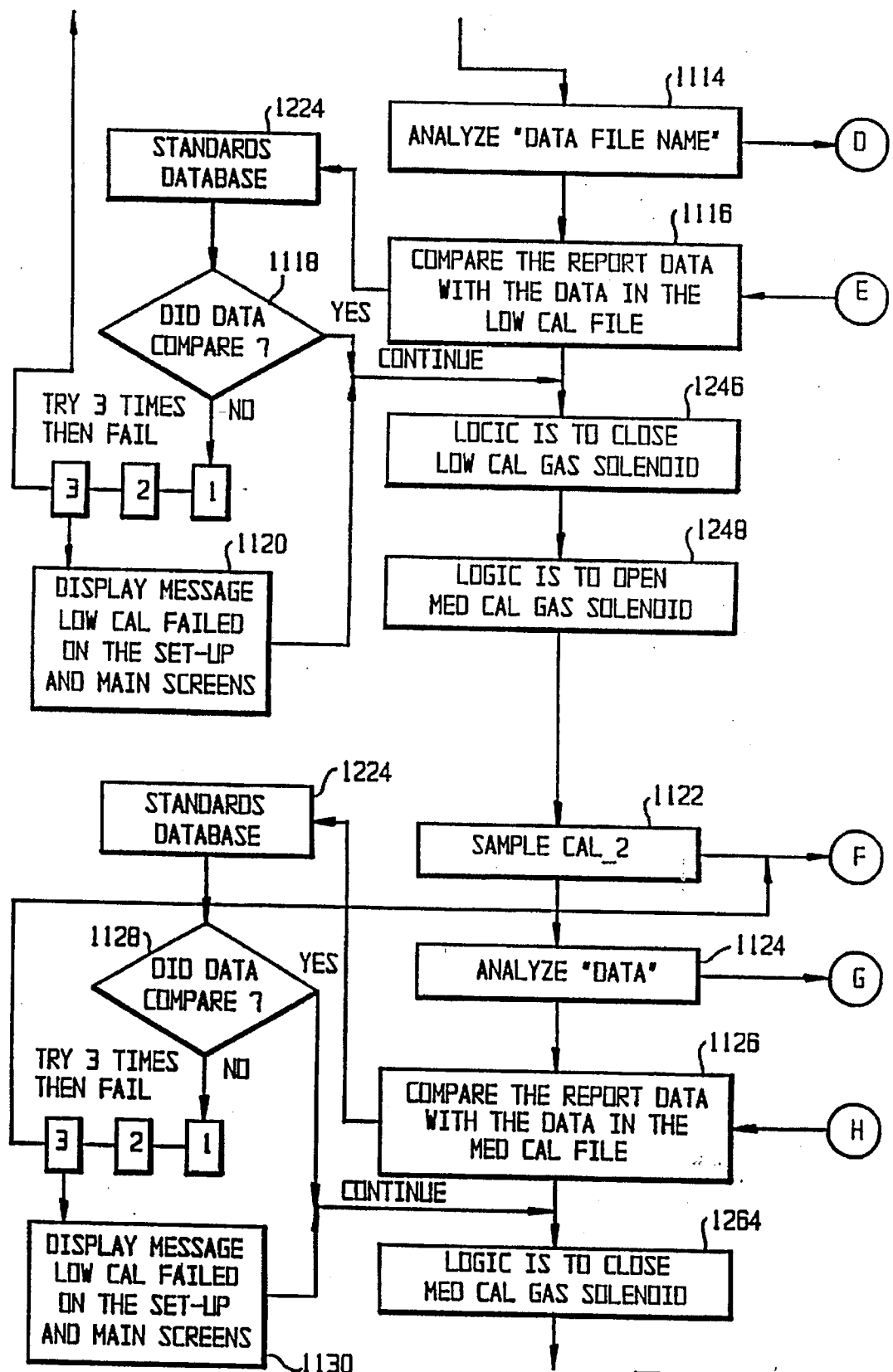
Figure 11C:
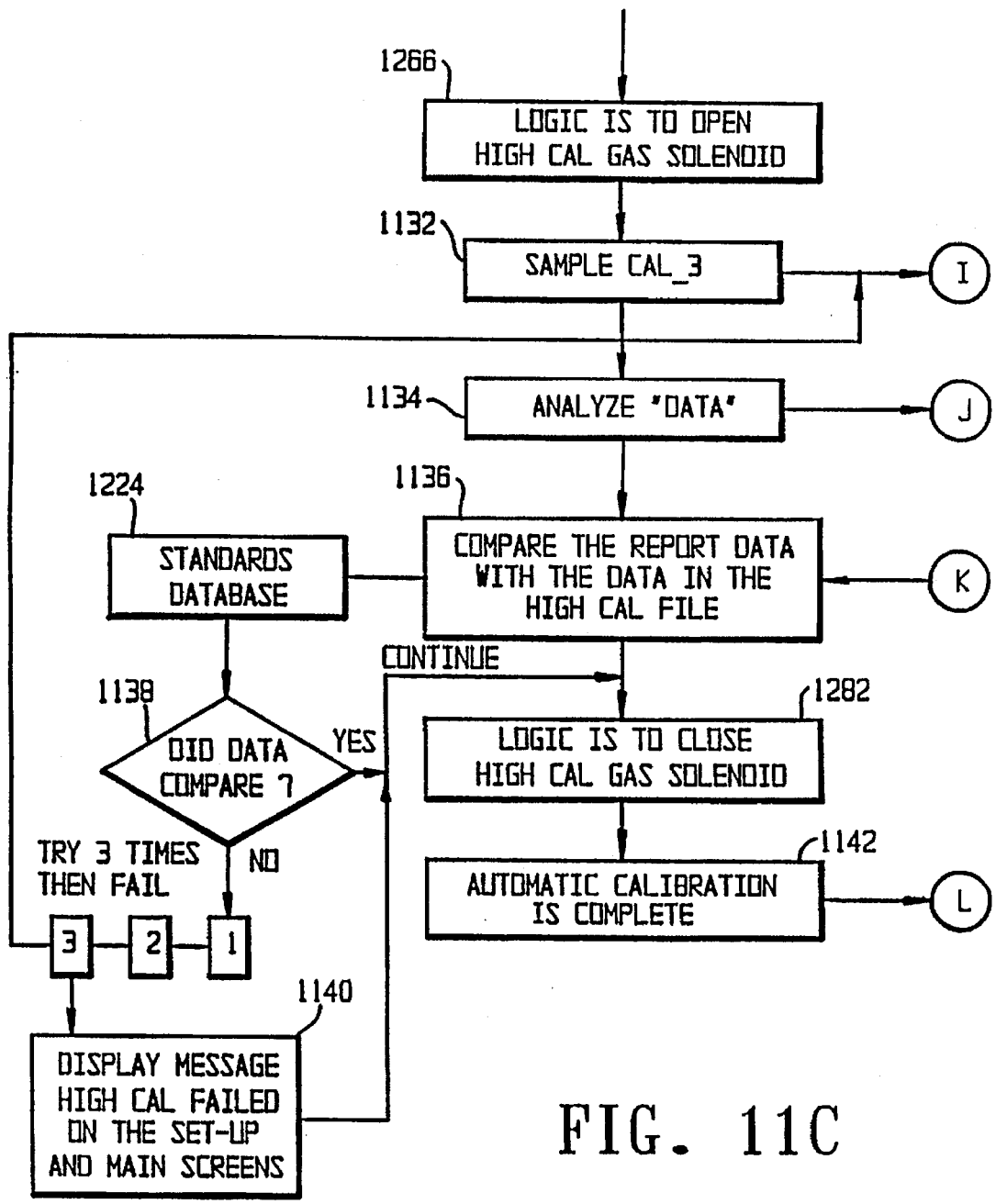

The main screen also allows the operator to enter various compounds and their associated calibration levels which will be used to calibrate the continuous emissions monitoring system of the present invention. A provision is also made at the main screen for the operator to print reports, to run the Automatic Calibration Routine, the flow chart of the software of which is shown in FIGS. 11A–11C, and to provide alarm messages to the operator.

At step 1208, the operator is required to enter a password before being allowed to utilize the software further. After the operator has entered an acceptable password at step 1208, the set up screen is shown to the operator at step 1210. The purpose of the set up screen is to allow the operator to enter the standards for various files and functions which will then form the Standards Database which is utilized at step 1224. The set up screen provides a mechanism by which the operator can enter the various compounds which the continuous emissions monitoring system of the present invention seeks to monitor, as well as the molecular weight of those compounds and the particular channel in which that compound is believed to be found. If no channel is indicated, then the system assumes that the compound is to be found in channel A.

Three tables are also provided for forming the calibration gas files for the low calibration gas, medium calibration gas and high calibration gas. The operator inputs the appropriate PPM of each calibration gas for the appropriate compound set forth in the compounds file.

Information is also solicited from the operator at the setup screen for the peak table channel calibration file. The operator again inputs the compounds to be monitored (or they may be input automatically based upon their input in the compounds file) and the values for the chromatographic peak retention time and the retention time window needed by the EZChrom software. The setup tables may also provide for easy access to a master compounds table, a peak area table, a table for each of the low, medium, and high calibration gases, a Set Sequence Time Subroutine and for printing a report of the information shown on the setup screen.

From the main screen, the operator can also move to a trends PPM volume screen, a trends in Lbs. screen or a trends in mass flow screen. Each of those screens shows a graph over a predetermined time period, such as fifteen minutes, in different trace colors if necessary, of the trends in the PPMv, Lbs, or mass flow of the continuous emission monitoring system of the present invention.

At steps 1216, 1212 and 1218, the operator fills in the data for the low calibration gas file, the medium calibration gas file and the high calibration gas file, respectively. This data is entered when the respective calibration gas bottle is changed and at the initial startup of the continuous emissions monitoring system of the present invention. Such data is typically furnished by the gas supplier. In order to enter this data, the operator will have to have already entered the required password at step 1208.

The gas chromatograph calibration data is compared against the data in each of the respective low calibration, medium calibration and high calibration gas files in order to confirm that the gas chromatograph 114 or gas chromatograph contained in the gas chromatographic system 192, as appropriate, is properly calibrated.

At step 1214, the operator fills in the data in the compounds file. The data is entered according to the specific monitoring requirements for the continuous emissions monitoring system, that is, the specific compounds which the continuous emissions monitoring system is monitoring. Again, the required password must have been entered at step 1208 before the operator can gain access to enter data in this file. The compounds file is used to select five or more compounds for displaying and trending on the main operator display screen described above in connection with step 1206.

At step 1220, the operator fills in the data in the channel A peak calibration file. At step 1222, the operator fills in the data in the channel B peak calibration file. The data entered into the peak table channel A and peak table channel B calibration files, which data was discussed above, is entered in accordance with the specific monitoring requirements of the continuous emissions monitoring system of the present invention. As with steps 1212–1218, the operator must have successfully entered the required password at step 1208 before data can be entered in either of these two files. The peak table channel A calibration file is used to compare the data from the "Channel A Area Report" sent from the EZChrom software while the peak channel B calibration is used to compare the data sent from the "Channel B Area Report" sent by the EZChrom software. Typically, all communications between the supervisor computer and the computer running the EZChrom software are made using Visual Basic commands and DDE.

Figure 13A:
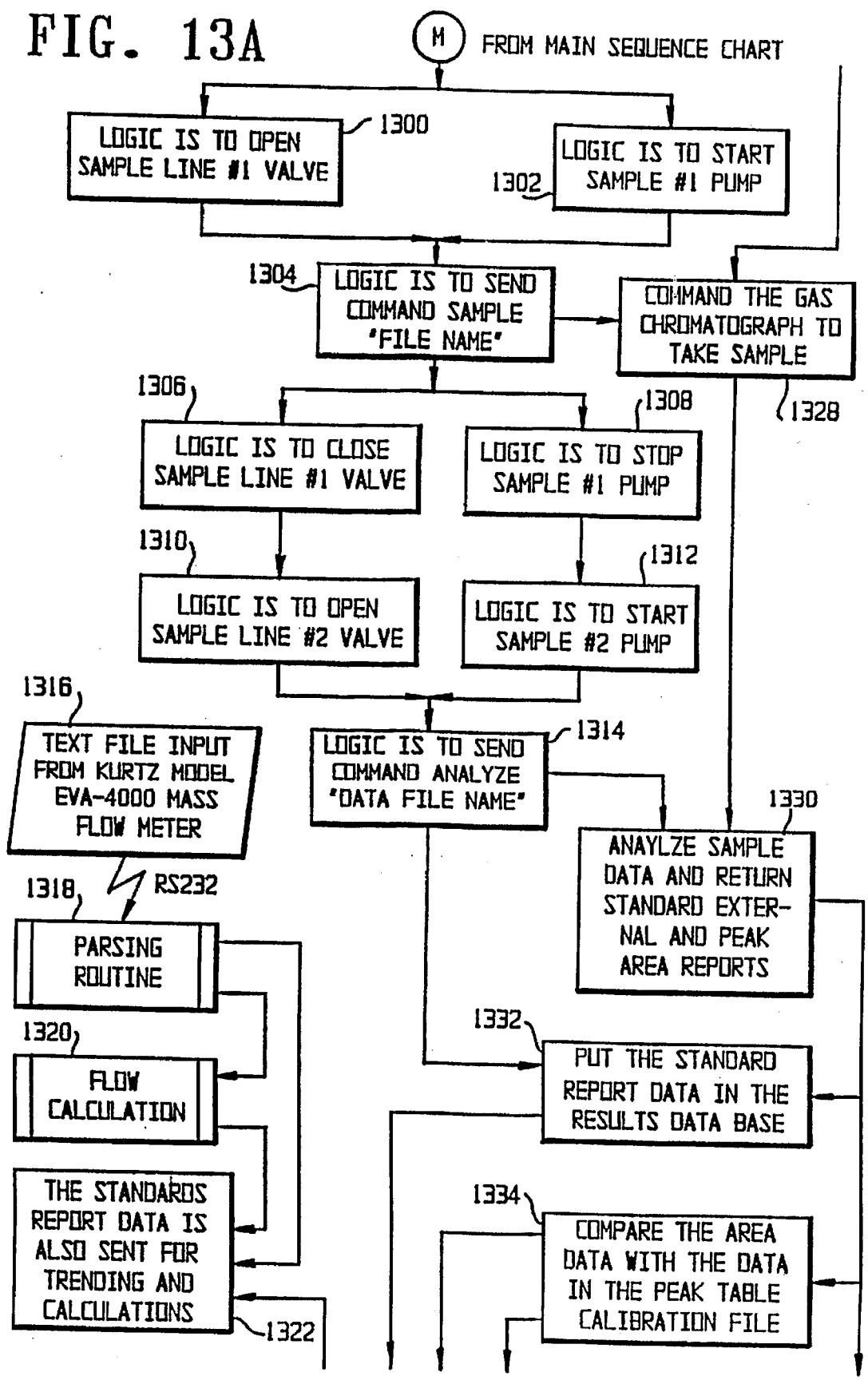
FIGS. 13A–13D are a flow chart illustrating the Automatic Sample Mode Logic Routine software used with the system of the present invention illustrated in FIGS. 2B, 9 and 10.
Figure 13B:
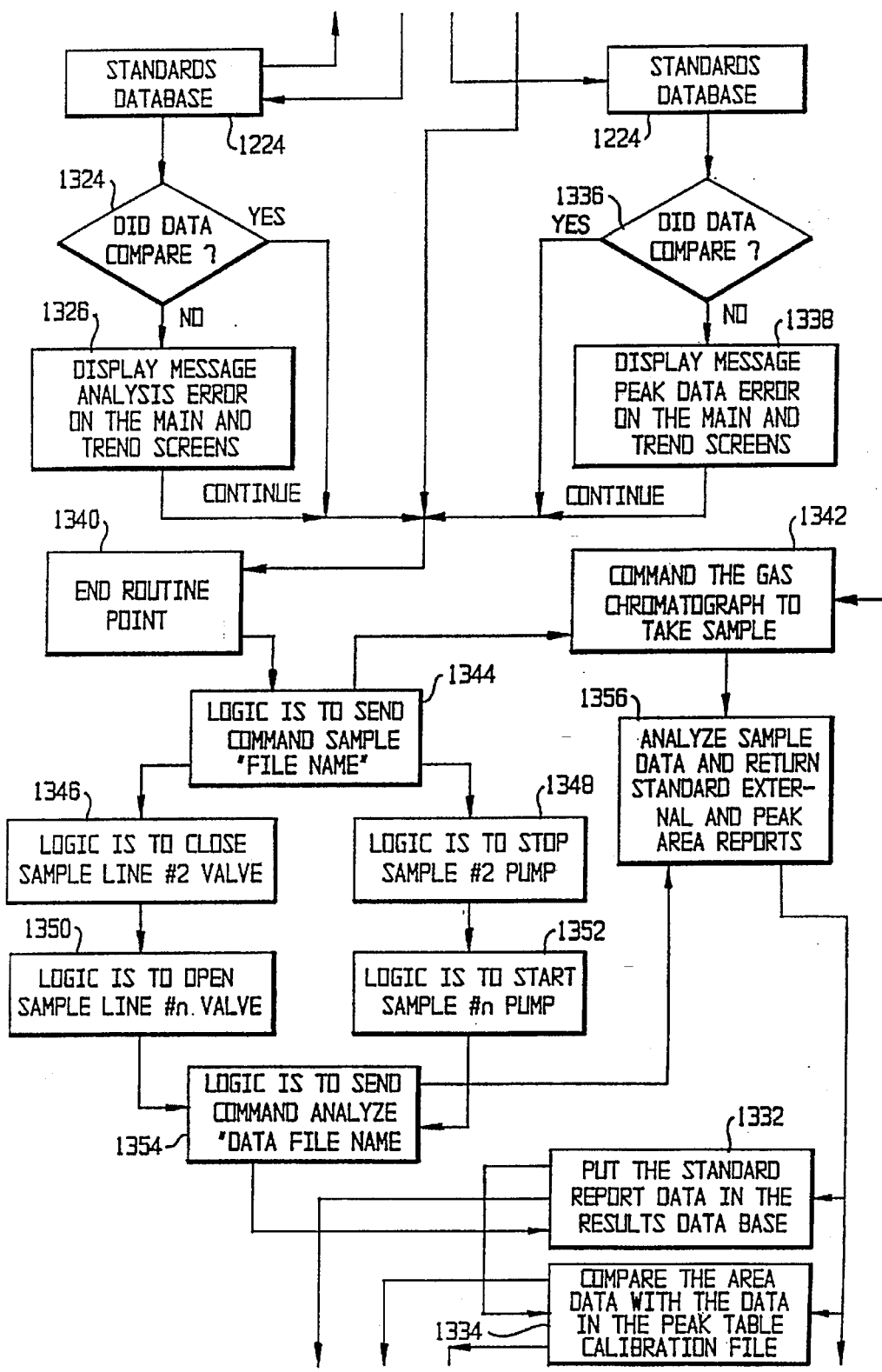
Figure 13C:
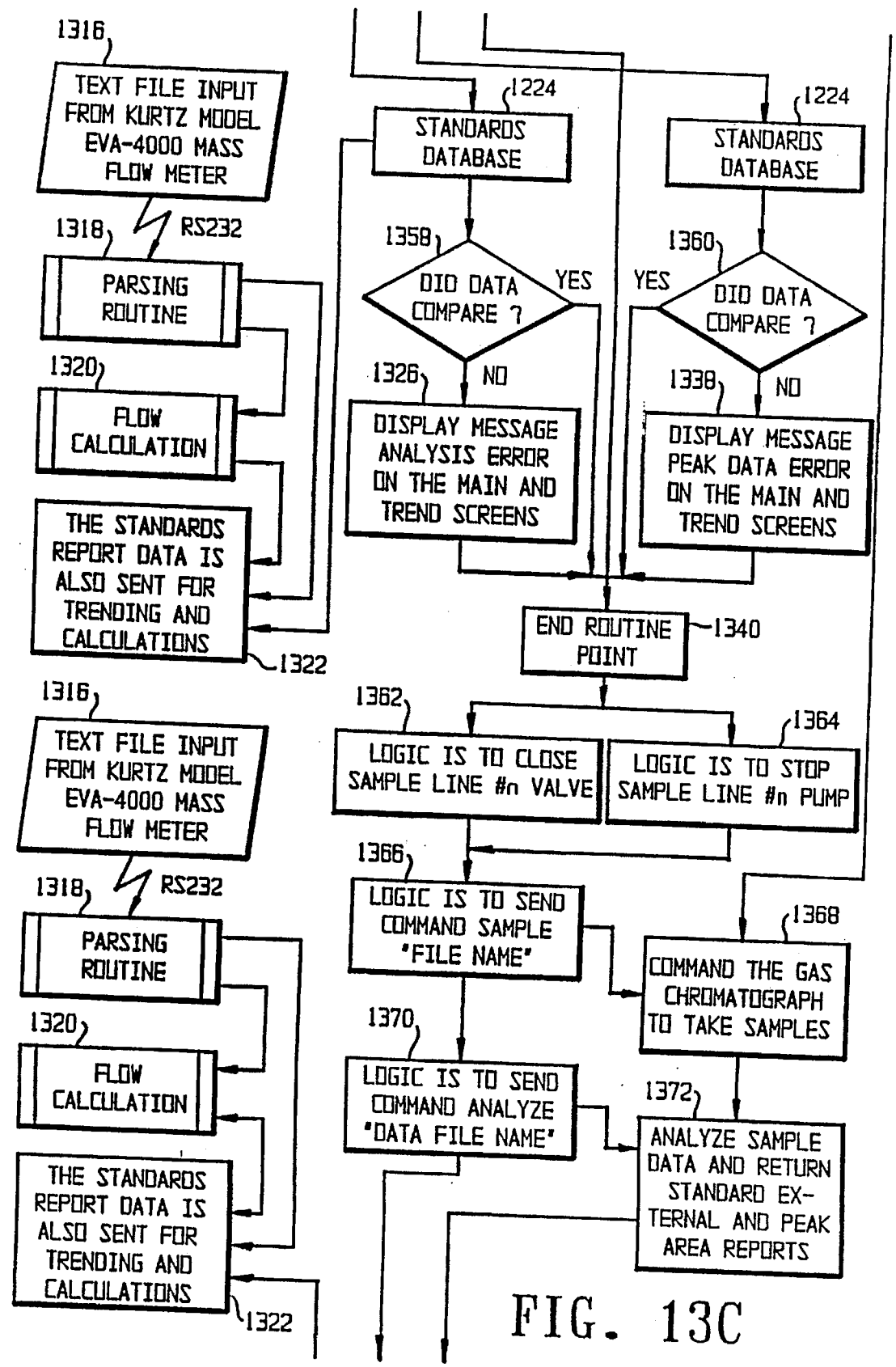
Figure 13D:
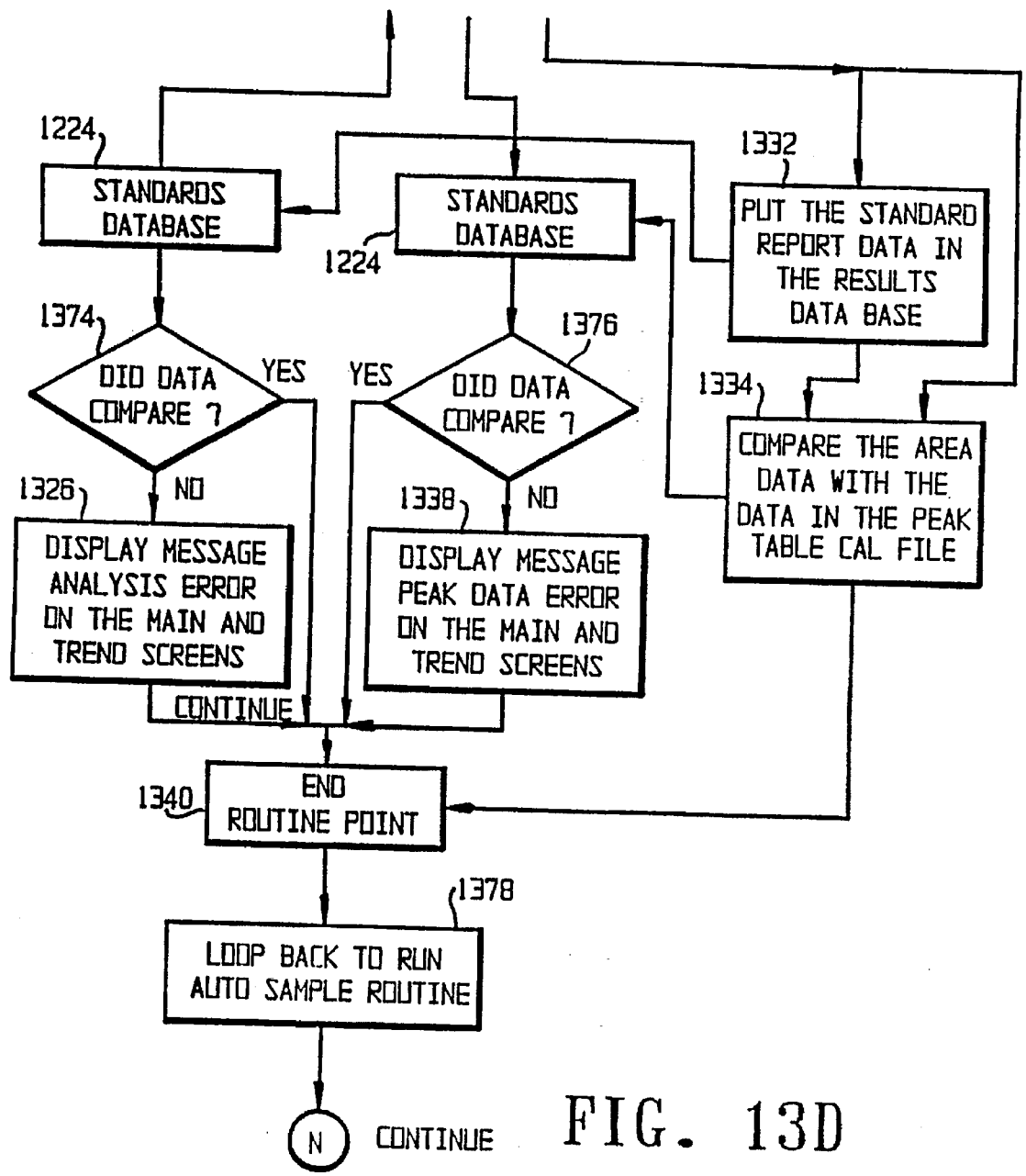

After the data has been entered at steps 1210–1222, the Standards Database 1224 has been created and then the operator sends a command to have the EZChrom software operate the appropriate GC according to the Open Method at step 1226. A command is then sent by the supervisor computer to the EZChrom computer to load the method file at step 1228. After the operator sends the command Open Method at step 1226, the Automatic Sample Mode Logic Routine shown in FIGS. 13A–13C is commanded to open the low calibrate gas solenoid at step. 1230. The operator then sends the command Sample Cal__1, at step 1232. That command is sent to the GC or EZChrom computer which commands the particular gas chromatograph selected to take a sample at step 1234.

At step 1236, the operator sends the command Analyze Data and File Name which sends an instruction to the EZChrom computer which is executed at step 1238. At step 1238, the EZChrom computer analyzes the sample data and returns the Standard External and Peak Area Reports. The Standard External Report contains, for up to fifty compounds, the name of the compound, the calculated amount of the compound and the units of that compound, as well as the retention time. That report is also sent to the trends files or routines so that the data contained therein can be graphically displayed for the operator.

After steps 1236 and 1238, the report data is compared with the data in the low gas calibrate file at step 1240. At step 1242, a determination is made of whether the data compared at step 1240 with the data in the Standards Database 1224 were the same. In the event that a negative determination is made at step 1242, then two more samples are taken by the gas chromatograph and steps 1236–1242 are repeated a second time. If a negative determination is again made, then a sample is taken for the third time and steps 1236–1242 are again executed. In the event of a third negative determination at step 1242, then a message is displayed on the setup and main screens for the operator that the low calibration has failed at step 1244.

After step 1244 or in the event of an affirmative determination at step 1242, then the Automatic Sample Mode Logic Routine is commanded to close the low calibrate gas solenoid at step 1246 and then to open the medium calibration gas solenoid at step 1248. At step 1250, the operator then sends the command Sample Cal_2. That command is transmitted to the EZChrom computer which commands the gas chromatograph under test to take a sample at step 1254.

The Main Sequence Calibrate Routine then performs the same functions at steps 1252, 1256, 1258, 1260 and 1262 with respect to the medium calibration gas file as discussed above in connection with steps 1236–1244 relating to the low calibration gas file.

After an affirmative determination at step 1260 or the execution of step 1262, the Automatic Sample Mode Logic Routine is instructed to close the medium calibrate gas solenoid at step 1264 and to open the high calibrate gas solenoid at step 1266. At step 1268, the operator sends to the EZChrom computer the command Sample Cal_3, which is received at step 1270 by the EZChrom software which commands the gas chromatograph being tested to take a sample. The Automatic Calibration Routine then executes steps 1272–1280, which perform the same function as steps 1236–1244, except with respect to the high calibration gas file in place of the low calibration gas file.

After an affirmative determination at step 1278 or after step 1280, the Automatic Sample Mode Logic Routine is instructed to close the high calibration gas solenoid at step 1282 and the operator then may select the Automatic Sample Mode Logic Routine, the flow chart of which is shown in FIGS. 13A–13D, at step 1284 to begin monitoring one or more air streams. The Main Sequence Calibrate Routine then ends at step 1286 and the supervisor computer then begins executing the Automatic Sample Mode Logic Routine unless the operator commands a stop at step 1288.

The flow chart of the Automatic Calibration Routine is shown in diagrammatic flow chart form in FIGS. 11A–11C. The Automatic Calibration Routine is used on the supervisory computer and is used for accomplishing unattended recalibration of the chromatographic system at user-specified time intervals such as every 24 hours. The Automatic Calibration Routine has access to the information from the Standards Database 1224 generated by the Main Sequence Calibrate Routine. A determination is then made at step 1100 of whether a predetermined time has been reached. A clock 1102 is used to compare the predetermined time at step 1100. If a negative determination is made at step 1100, meaning that the present time is not the predetermined time for executing the Automatic Calibration Routine, then the Automatic Calibration Routine ends at step 1106 and the control of the supervisory computer returns to the Main Sequence Calibrate Routine.

If an affirmative determination is made at step 1100, meaning that the predetermined time is equal to the present time, then the Automatic Calibration Routine sets up to perform automatic calibration by stopping any automatic sample routine that may be in progress at the end of the automatic sample routine at step 1104. At step 1106, the end of the routine point is reached and any ongoing automatic sample routine or other currently running routines are aborted when the system is placed in manual mode.

Then, at step 1108, the Open Method is selected and sent to step 1230 of the Main Sequence Calibrate Routine. The Automatic Sample Mode Logic Routine is then instructed to open the low calibration gas solenoid at step 1110 and a Sample Cal_1 instruction is sent at step 1112 to the EZChrom computer which causes the EZChrom computer to command the gas chromatograph being calibrated to take a sample at step 1234. The data file name is then analyzed at step 1114 and sent to the EZChrom computer which receives it as an input at step 1238 and then proceeds to analyze the sample data and returns the Standard External and Peak Air Reports to the Automatic Calibration Routine at step 1116.

At step 1116, the Automatic Calibration Routine compares the report data with the data in the low calibration gas file, using the Standards Database 1224. At steps 1118 and 1120, the Automatic Calibration Routine performs the comparison of the report data with the data in the low calibration gas file contained in the Standards Database, in a manner similar to that described above in connection with steps 1242 and 1244.

After completing that comparison, and either displaying a message that the low calibration failed at step 1120 or achieving an affirmative result at step 1118, the Automatic Calibration Routine commands the Automatic Sample Mode Logic Routine to close the low calibration gas solenoid at step 1246 and to open the medium calibration gas solenoid at step 1248. The Automatic Calibration Routine then proceeds to issue the Sample Cal_2 command at step 1122 as well as the Analyze Data command at step 1124 and to then compare the report data at step 1126 generated by the EZChrom computer at steps 1254 and 1256 with regard to the medium calibration gas file in the same manner as described above in connection with the low calibration gas file.

After displaying a message that the medium calibration failed at step 1130 or making an affirmative determination of the comparison of the medium calibration file data with the Standards Database at step 1128, the Automatic Sample Mode Logic Subroutine is instructed to close the medium calibration gas solenoid at step 1264 and to open the high calibration gas solenoid at step 1266.

The Automatic Calibration Routine then issues the Sample Cal_3 command at step 1132 which causes the EZChrom computer to command the gas chromatograph to take a sample at step 1270. The Analyze Data command is issued at step 1234 by the Automatic Calibration Routine, which causes the EZChrom computer to analyze the sample data and return the Standard External and Peak Air Reports at step 1274 to the Automatic Calibration Routine where they are compared at step 1136 with the data in the high calibration gas file contained in the Standards Database 1224.

After the comparison performed at step 1138, which is the same as the comparison performed at steps 1118 and 1128, either a message is displayed on the setup and main screens that the high calibration routine has failed at step 1140 or an affirmative determination is made at step 1138 that the report data corresponds to the data in the high calibration file in the Standards Database 1224. The Automatic Sample Mode Logic Routine is then instructed to close the high calibration gas solenoid at step 1282. At step 1142, the Automatic Calibration Routine is determined to be complete and then control of the supervisor computer returns to the Main Sequence Calibrate Routine, at step 1286.

FIGS. 13A–D are a diagram of a flow chart of the Automatic Sample Mode Logic Routine which is called from either the Main Sequence Calibrate Routine, the flow chart of which is shown in FIGS. 12A–12C, or the Automatic Calibration Routine, the flow chart of which is shown in FIGS. 11A–11C. After the end routine point of the Main Sequence Calibrate Routine is reached at step 1286, the Automatic Sample Mode Logic Routine is called. The purpose of the Automatic Sample Mode Logic Routine is to automatically obtain samples from each of the gas chromotragraphs currently being used, a predetermined time period apart, such as once every second.

Once the Automatic Sample Mode Logic Routine is called, it opens the sample line 1 valve 908a at step 1300 and then starts the sample number 1 pump 910a at step 1302. The Automatic Sample Mode Logic Routine then sends the command Sample File Name at step 1304 to the EZChrom computer which commands the gas chromatograph currently in use to take a sample at step 1328. While the sample is being taken by the selected gas chromatograph 114 or 192, the Automatic Sample Mode Logic Routine closes the sample line 1 valve 908a at step 1306 and stops the sample number 1 pump 910a at step 1308.

The Automatic Sample Mode Logic Routine then opens the sample line number 2 valve 906a at step 1310 and starts the sample number 2 pump 910b at step 1312. It then sends the command Analyze Data File Name at step 1314. That command is sent to the EZChrom computer which, at step 1330, analyzes the sample data and returns the Standard External and Peak Area Reports.

The Standards Report data received from the analysis at step 1330 by the EZChrom computer is then put into the Results Database at step 1332 and then compared at step 1324 to the Standards Database 1224. The Results Database logs, by date and time for each of the compounds being monitored, the concentration amount, the units in PPM, the RT, the mass flow, the number of units per hour, the mass flow total and the units of the mass flow total in pounds volume. In addition, any exception codes are also stored in the Results Database.

While the Automatic Sample Mode Logic Routine is operating, the text files input from the Kurtz mass flow meter 108 are sent by means of, for example, an RS 232 port to a custom Parsing Routine. The output from the Parsing Routine is fed to the flow calculation module at step 1320 which calculates such values as the standard cubic feet of air/per minute. The outputs from the Parsing Routine at step 1318 and flow calculations at step 1320 are fed to the Standards Report data at step 1322. The Standards Report data is also sent for use in determining the various trends described above as well as for other calculations. Obviously, values from the Standards Database 1224 are also received at step 1322 for creating the trending information and performing the calculations.

The analyzed sample data in the form of Standard External and Peak Area Reports is also fed to step 1334 where the peak area data is compared with the data in the peak table calibration file contained in the Standards Database 1224. The comparison of the Peak Area Report data with the peak table calibration file is performed at step 1336. If the data does not compare, meaning that more chromatographic peaks than those analyzed for are present, a negative determination is made at step 1336 and a peak data error message is displayed on the main and trend screens at step 1338 and reported to the database.

Similarly, if a negative determination is made at step 1324, meaning that more chromatographic peaks than those analyzed for are present, a message of an analysis error is displayed on the main and trend screens at step 1326. After steps 1326 and 1338 or in the event of an affirmative determination at steps 1324 and 1336, the end routine point is reached at step 1340, indicating that the sampling of the air stream contained in line 1 has been completed.

After step 1340, indicating the end of the sample routine point has been reached, the Automatic Sample Mode Logic Routine sends a new Sample File Name command at step 1344 to the EZChrom computer which then commands the gas chromatograph being utilized to take a sample of the air stream in the second sample line 912b at step 1342. The Automatic Sample Mode Logic Routine then closes the sample line number 2 valve 906a at step 1346 and stops the sample number 2 pump 910b at step 1348.

Next, the Automatic Sample Mode Logic Routine opens the sample valve for sample line number n (sample line number 5 (912e) as shown in FIG. 9B) at step 1350 and starts a sample number n pump (sample number 5 pump 910e in FIG. 9B) at step 1352. It should be noted that while 9A–9B shows the continuous emissions monitoring system of the present invention monitoring five different sample lines 912a–912e, the system can be expanded to monitor n number of sample lines. That is illustrated, for example, by steps 1350 and 1352 of the Automatic Sample Mode Logic Routine shown in FIGS. 13A–13D.

The Automatic Sample Mode Logic Routine then sends the command Analyze Data File Name to the EZChrom computer which analyzes the sample data received from the appropriate gas chromatograph 114 or chromatographic system 192 at step 1356 and returns the Standard External Report to the Automatic Sample Mode Logic Routine at step 1332. The EZChrom computer also returns the Peak Area Report to step 1334 of the Automatic Sample Mode Logic Routine.

At step 1332, the Standard Report Data is placed in the Results Database.

As discussed above, the text file information is input from the mass flow meter 108a at step 1316 and processed as described previously at steps 1318–1322. The report data contained in the Results Database is then compared to the data contained in the Standards Database 1224 at step 1358. In addition, the peak area data is compared with the data in the peak table calibration file contained in the Standards Database 1224 at step 1360. If a negative determination is made at steps 1358 or 1360 then a message is displayed on the main and trend screens indicating an analysis error at step 1326 or a message indicating a peak data error at step 1338, respectively.

After steps 1326 and 1338 or in the event of an affirmative determination at steps 1358 and 1360, the Automatic Sample Mode Logic Routine reaches an end routine point 1340. It is at this point that the control software of the continuous emissions monitoring system of the present invention will stop in the event that the operator has commanded a controlled stop.

After step 1340, the Automatic Sample Mode Logic Routine closes the sample line number n valve at step 1362 and then stops the sample number n pump at step 1364. The command Sample File Name is then sent to the EZChrom computer at step 1366. In response, the EZChrom software commands the gas chromatograph to take a sample from the number n line at step 1368.

The Automatic Sample Mode Logic Routine then sends the command Analyze Data File Name to the EZChrom computer at step 1370. In response, the EZChrom computer analyses the sample data at step 1372 and returns the Standard External Report to the Automatic Sample Mode Logic Routine at step 1332. It returns the Peak Area Report to the Automatic Sample Mode Logic Routine at step 1334.

After steps 1332 and 1334, the Automatic Sample Mode Logic Routine performs the comparisons of the data received at steps 1332 and 1334, as previously described. Those comparisons are generated at steps 1374 and 1376. In addition, the text file input from the mass flow meter 108a at step 1316 is parsed at step 1318, flow calculations are made at step 1320 and the Standards Report data is sent for trending and calculations at step 1322, all as described previously.

After the completion of steps 1326, 1338, 1374 and 1376, all of which have also been described previously, the Automatic Sample Mode Logic Routine then continues to the end routine point at step 1340. If the operator has not commanded a controlled stop then the control system software for the continuous emissions monitoring system of the present invention loops back to run the Automatic Sample Mode Logic Routine again at step 1378. When the Automatic Sample Mode Logic Routine is completed, control returns to the Main Sequence Calibrate Routine.

In addition to the Results Database discussed above, the control software maintains at least two other databases. The first of those databases is termed the Averaged Database. This Averaged Database includes entries which are made as a result of a query every 15 minutes of the Results Database. The number of samples reported in the Results Database during this 15 minute period is averaged and entered as a record in the Averaged Database.

The second additional database which is maintained by the control software of the continuous emissions monitoring system of the present invention is the 24 Hour Record Database. The 24 Hour Record Database is generated as a result of a query every 1 hour period of the Averaged Database. The number of samples reported in the Averaged Database during that 1 hour period are "moving averaged" and then entered as a record in the 24 Hour Record Database. In addition, every 24 hours, at a predetermined time, such as 24:00 hours, the data stored in the 24 Hour Record Database is archived onto a suitable medium.

It will be obvious to those of ordinary skill in the art that there are many different languages with which the control software for the continuous emissions monitoring system of the present invention can be implemented. For example, the control program can be written in C, C++ or Visual Basic. Also, control software platforms such as Factory Link™, available from U.S. Data of Richardson, Tex., IBM Genesis™, available from IBM Corporation, Armonk, N.Y., or other control software platforms, many of which already contain control tools and algorithms, can be used with an application written for use with such platforms. A preferable control software platform is U.S. Data's Factory Link™platform.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. Apparatus for determining the concentration of at least one of a plurality of compounds contained in air carrying said at least one of a plurality of compounds comprising:

at least one gas chromatograph;

a sample collection means connected between said air and said at least one gas chromatograph for providing at least one sample of said plurality of compounds to said at least one gas chromatograph, said sample collection means including a plurality of conduit means connected to receive a plurality of samples containing said at least one of a plurality of compounds;

a first, second and third calibrating gas means connected to said at least one gas chromatograph for calibrating said at least one gas chromatograph;

a digital data processor connected to operate and control said at least one gas chromatograph, said sample collection means and said first, second and third calibrating gas means for analyzing said at least one sample to determine the concentration of said at least one of a plurality of compounds in said air and thereby the presence of different types of emissions in said air; and wherein said sample collection means further comprises a plurality of valves connected between said first, second and third calibrating gas means and said plurality of conduit means and said at least one gas chromatograph in order to alternatingly provide said first, second and third calibrating gases and each one of said plurality of samples to said at least one gas chromatograph for one of calibration and analysis.

2. The apparatus of claim 1, wherein at least a portion of said plurality of valves are contained within a heated valve enclosure.

3. The apparatus of claim 2, wherein said heated valve enclosure is heated to a temperature of at least 110 degrees Celsius in order to prevent adsorption of said plurality of compounds by said valves.

4. A method for determining the presence of different types of emissions in air in an environment by monitoring the concentration of at least one volatile or semi-volatile compound contained in at least one air stream carrying said at least one volatile or semi-volatile compound, comprising the steps of:

a) calibrating at least one gas chromatograph using at least three calibration gases;

b) obtaining a sample of said at least one air stream containing said at least one compound;

c) providing said sample of said at least one air stream to said at least one gas chromatograph;

d) operating said at least one gas chromatograph under control of a digital data processor to analyze said sample of said at least one air stream to determine the concentration of said at least one compound in said sample and thereby the presence of different types of emissions in said air; and e) controlling steps a)–c) using said digital data processor.

5. A method for determining the presence of different types of emissions in air in an environment by monitoring at least one of a plurality of air streams for determining the concentration of at least one volatile or semi-volatile compound in at least one of said plurality of air streams carrying said at least one volatile or semi-volatile compound, comprising the steps of:

a) calibrating at least one gas chromatograph using at least three calibration gases;

b) selecting said at least one of said plurality of air streams to be sampled;

c) obtaining a sample of said selected one of said plurality of air streams carrying said at least one compound;

d) providing said sample of said selected air stream to said at least one calibrated gas chromatograph;

e) operating said at least one calibrated gas chromatograph under control of a digital data processor to analyze said sample of said selected air stream to determine the concentration of said at least one compound in said sample and thereby the presence of different types of emissions in said air; and f) controlling steps a)–d) using said digital data processor.

6. Apparatus for determining the presence of different types of emissions in air in an environment by determining the concentration of at least one of a plurality of compounds contained in air carrying said at least one of a plurality of compounds comprising:

at least one gas chromatograph;

a sample collection means connected between said air and said at least one gas chromatograph for providing at least one sample of said plurality of compounds to said at least one gas chromatograph;

at least a first calibrating gas means connected to said at least one gas chromatograph for calibrating said at least one gas chromatograph; and a digital data processor connected to operate and control said at least one gas chromatograph, said sample collection means and said at least first calibrating gas means for analyzing said at least one sample to determine the concentration of said at least one of a plurality of compounds in said air and thereby the presence of different types of emissions in said air.

7. The apparatus of claim 6, further including at least a second gas chromatograph and wherein said at least one sample is fed to said at least first and second gas chromatographs and is processed in parallel by said at least first and second gas chromatographs to determine the concentration of said at least one of a plurality of compounds.

8. The apparatus of claim 6, wherein said at least one gas chromatograph is a plurality of gas chromatographs and wherein said at least one sample is fed to at least two of said plurality of gas chromatographs and is processed in parallel by said at least two gas chromatographs to determine the concentration of said at least one of a plurality of compounds.

9. A method for monitoring the inlet and discharge air streams of a cleaning element, said inlet air stream containing at least one volatile or semi-volatile compound, in order to monitor the cleaning effect achieved by said cleaning element, comprising the steps of:

calibrating at least one gas chromatograph using at least one of a plurality of calibrating gases;

sampling said inlet air stream containing said at least one volatile or semi-volatile compound;

providing said sample of said inlet air stream to said at least one gas chromatograph;

operating said at least one gas chromatograph to analyze said sample of said inlet air stream to determine the presence of said at least one volatile or semi-volatile compound in said inlet air stream, as well as its concentration;

sampling said discharge air stream;

providing said sample of said discharge air stream to said at least one gas chromatograph to which said sample of said inlet air stream was provided and;

operating said at least one gas chromatograph to analyze said sample of said discharge air stream to determine the presence of said at least one volatile or semi-volatile compound in said discharge air stream, as well as its concentration.

10. The method of claim 9, wherein said calibrating, sampling, providing and analyzing steps are performed on a continuous basis under control of a digital data processor.

11. The method of claim 9, wherein said step of calibrating utilizes at least three different calibrating gases.

12. The method of claim 11, wherein said at least one gas chromatograph is alternatingly calibrated using each one of said at least three different calibrating gases.

13. A method for monitoring the inlet and discharge air streams of a cleaning element, said inlet air stream containing a plurality of volatile or semi-volatile compounds, in order to monitor the cleaning effect achieved by said cleaning element, comprising the steps of:

calibrating a plurality of gas chromatographs, each using at least one of a plurality of calibrating gases;

sampling said inlet air stream containing said plurality of volatile or semi-volatile compounds;

providing said sample of said inlet air stream to said plurality of gas chromatographs;

operating said plurality of gas chromatographs to analyze said sample of said inlet air stream to determine the presence of said plurality of volatile or semi-volatile compounds in said inlet air stream, as well as their concentrations;

sampling said discharge air stream;

providing said sample of said discharge air stream to said plurality of gas chromatographs to which said sample of said inlet air stream was provided; and operating said plurality of gas chromatographs to analyze said sample of said discharge air stream to determine the presence of said plurality of volatile or semi-volatile compounds in said discharge air stream as well as their concentrations.

14. The method of claim 13, wherein said calibrating, sampling, providing and analyzing steps are performed on a continuous basis under control of a digital data processor.

15. The method of claim 13, wherein each one of said plurality of gas chromatographs is operated to analyze its respective inlet and discharge air streams for the presence of a different one of said plurality of volatile or semi-volatile compounds.

16. The method of claim 13, wherein each of said plurality of gas chromatographs is operated on a simultaneous basis for monitoring for a respective one of said plurality of volatile or semi-volatile compounds, as well as its concentration.

17. The method of claim 13, wherein at least two of said plurality of gas chromatographs are operated to monitor for the same one of said plurality of volatile or semi-volatile compounds, but within different ranges of concentration.

18. The method of claim 13, wherein at least two of said gas chromatographs are operated to monitor for the same one of said plurality of volatile or semi-volatile compounds using different operating conditions.

19. The method of claim 13, wherein said step of calibrating utilizes at least three different calibrating gases.

20. The method of claim 19, wherein each of said plurality of gas chromatographs is alternatingly calibrated using each one of said at least three different calibrating gases.

21. A method for analyzing and measuring a plurality of inlet and discharge air streams for the presence of one or more of a plurality of volatile or semi-volatile compounds in said plurality of air streams, comprising the steps of:

calibrating a plurality of gas chromatographs, each using at least one of a plurality of calibrating gases;

sampling each of said plurality of inlet air streams containing one or more of said plurality of volatile or semi-volatile compounds;

providing each respective one of said plurality of inlet air stream samples to a different one of a plurality of gas chromatographs;

operating said plurality of gas chromatographs to analyze a respective inlet air stream sample to measure the presence and concentration of one of said one or more of said plurality of volatile or semi-volatile compounds in that respective inlet air stream sample;

sampling each of said plurality of discharge air streams;

providing each respective one of said plurality of discharge air stream samples to a different one of said plurality of gas chromatographs; and operating said plurality of gas chromatographs to analyze a respective discharge air stream sample to measure the presence and concentration of one of said one or more of said plurality of volatile or semi-volatile compounds in that respective discharge air stream sample.

22. The method of claim 21, wherein said calibrating, sampling, providing and analyzing steps are performed on continuous basis under control of a digital data processor.

23. The method of claim 21, wherein each of said plurality of gas chromatographs is operated to analyze its respective inlet and discharge air streams for the presence of a different one of said plurality of volatile or semi-volatile compounds.

24. The method of claim 21, wherein each of said plurality of gas chromatographs is operated on a simultaneous basis for monitoring for a respective one of said plurality of volatile or semi-volatile compounds, as well as its concentration.

25. The method of claim 21, wherein at least two of said plurality of gas chromatographs are operated to monitor for the same one of said plurality of volatile or semi-volatile compounds, but within different ranges of concentration.

26. The method of claim 21, wherein at least two of said gas chromatographs are operated to monitor for the same one of said plurality of volatile or semi-volatile compounds using different operating conditions.

27. The method of claim 21, wherein said step of calibrating utilizes at least three different calibrating gases.

28. The method of claim 27, wherein each of said plurality of gas chromatographs is alternatingly calibrated using each one of said at least three different calibrating gases.

* * * * *